(12) United States Patent
Cals et al.

(10) Patent No.: US 10,556,866 B2
(45) Date of Patent: Feb. 11, 2020

(54) ROR GAMMA (RORγ) MODULATORS

(71) Applicants: LEAD PHARMA HOLDING B.V., Nijmegen (NL); SANOFI, Paris (FR)

(72) Inventors: Joseph Maria Gerardus Barbara Cals, Oss (NL); Sander Bernardus Nabuurs, Oss (NL)

(73) Assignees: LEAD PHARMA HOLDING B.V., Nijmegen (NL); SANOFI, Paris (FR)

(*) Notice: Subject to any disclaimer, the term of this patent is extended or adjusted under 35 U.S.C. 154(b) by 0 days.

(21) Appl. No.: 15/579,164

(22) PCT Filed: Jun. 3, 2016

(86) PCT No.: PCT/EP2016/062701
§ 371 (c)(1),
(2) Date: Dec. 1, 2017

(87) PCT Pub. No.: WO2016/193461
PCT Pub. Date: Dec. 8, 2016

(65) Prior Publication Data
US 2018/0162815 A1  Jun. 14, 2018

(30) Foreign Application Priority Data
Jun. 5, 2015 (EP) .................... 15170765

(51) Int. Cl.
C07C 317/32 (2006.01)
C07D 213/81 (2006.01)
(Continued)

(52) U.S. Cl.
CPC ............ C07D 213/81 (2013.01); A61P 29/00 (2018.01); A61P 37/00 (2018.01); C07C 311/46 (2013.01);
(Continued)

(58) Field of Classification Search
CPC .......................... C07D 213/81; C07C 317/32
See application file for complete search history.

(56) References Cited

U.S. PATENT DOCUMENTS 10,118,895 B2  11/2018 Cals
10,196,350 B2   2/2019 Cals
(Continued)

FOREIGN PATENT DOCUMENTS

EP  2842939 A1   3/2015
RU  2470012 C2  12/2012
(Continued)

OTHER PUBLICATIONS

Jul. 13, 2016 International Search Report issued in International Patent Application No. PCT/EP2016/062701.
(Continued)

*Primary Examiner* — Bruck Kifle
(74) *Attorney, Agent, or Firm* — Morrison & Foerster LLP

(57) ABSTRACT

Novel compounds according to Formula I

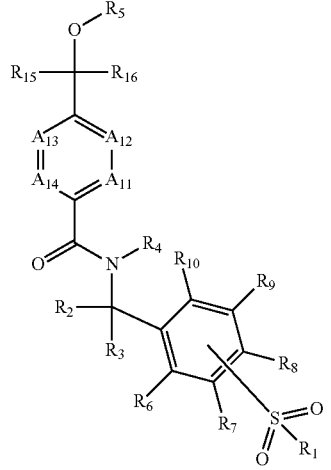

(Formula I)

or a pharmaceutically acceptable salt thereof wherein: $A_{11}$-$A_{14}$ are N or $CR_{11}$, $CR_{12}$, $CR_{13}$, $CR_{14}$, respectively, with the proviso that no more than two of the four positions A can be simultaneously N; $R_1$ is C(2-6)alkyl, C(3-6)cycloalkyl, C(3-6)cycloalkylC(1-3)alkyl, (di)C(3-6)cycloalkylamino or (di)(C(3-6)cycloalkylC(1-3)alkyl)amino; $R_5$ is H, hydroxyethyl, methoxyethyl, C(1-6)alkyl, C(6-10)aryl, C(6-10)arylC(1-3)alkyl, C(1-9)heteroaryl, C(1-9)heteroarylC(1-3)alkyl, C(3-6)cycloalkyl, (3-6)cycloalkylC(1-3)alkyl, C(2-5)heterocycloalkyl or C(2-5)heterocycloalkyl-C(1-3)alkyl; the sulfonyl group with $R_1$ is represented by one of $R_7$, $R_8$ or $R_9$; $R_{15}$ is H, C(1-6)alkyl, C(3-6)cycloalkyl, C(3-6)cycloalkylC(1-3)alkyl, C(6-10)aryl, C(6-10)arylC(1-3)alkyl, C(1-9)heteroaryl, C(1-9)heteroarylC(1-3)alkyl, C(2-5)heterocycloalkyl or C(2-5)heterocycloalkylC(1-3)alkyl; and $R_{16}$ is C(1-6)alkyl, C(3-6)cycloalkyl, C(3-6)cycloalkylC(1-3)alkyl, C(6-10)aryl, C(6-10)arylC(1-3)alkyl, C(1-9)heteroaryl, C(1-9)heteroarylC(1-3)alkyl, C(2-5)heterocycloalkyl or C(2-5)heterocycloalkylC(1-3)alkyl. The compounds can be used as inhibitors of RORγ and are useful for the treatment of RORγ mediated diseases.

6 Claims, No Drawings

(51) Int. Cl.
*C07C 311/46* (2006.01)
*A61P 37/00* (2006.01)
*A61P 29/00* (2006.01)

(52) U.S. Cl.
CPC ........ C07C 317/32 (2013.01); *C07C 2601/02* (2017.05)

(56) References Cited

U.S. PATENT DOCUMENTS

| | | |
|---|---|---|
| 10,259,782 B2 | 4/2019 | Cals |
| 2018/0162809 A1 | 6/2018 | Cals |
| 2018/0170877 A1 | 6/2018 | Cals |
| 2019/0040012 A1 | 2/2019 | Cals |
| 2019/0119204 A1 | 4/2019 | Cals |

FOREIGN PATENT DOCUMENTS

| | | |
|---|---|---|
| WO | WO2007120647 A2 | 10/2007 |
| WO | 2013/029338 A1 | 3/2013 |
| WO | WO2014125426 A1 | 8/2014 |

OTHER PUBLICATIONS

Jul. 13, 2016 Written Opinion of the International Searching Authority issued in International Patent Application No. PCT/EP2016/062701.

European Search Report (Extended) dated Aug. 19, 2015 for EP Application No. 15170765.0 filed on Jun. 5, 2015, 4 pages.

ROR GAMMA (RORγ) MODULATORS

The present invention relates to modulators of RORγ, to pharmaceutical compositions comprising the same and to the use of said compounds for the treatment of RORγ-mediated diseases or conditions, in particular autoimmune diseases and inflammatory diseases.

The retinoic-acid-receptor-related orphan receptor γt (RORγt) acts as a master regulator of the development of $T_H17$ cells, but also as a critical component in non-$T_H17$ IL-17 producing cells, such as for example γδ T-cells. The ROR gene family is part of the nuclear hormone receptor superfamily, and consists of three members (RORα, RORβ, and RORγ). Each gene is expressed in different isoforms, differing foremost in their N-terminal sequence. Two isoforms of RORγ have been identified: RORγ1 and RORγ2 (also known as RORγt). The term RORγ is used here to describe both RORγ1 and/or RORγ2.

The present invention relates to novel compounds according to Formula I

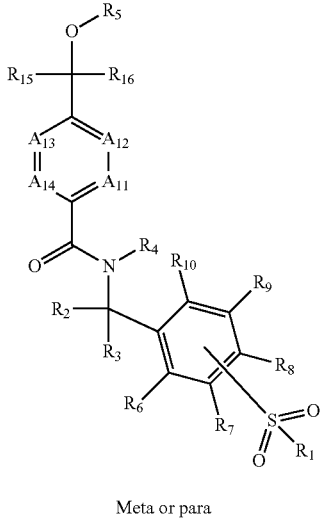

(Formula I)

Meta or para or a pharmaceutically acceptable salt thereof wherein:

$A_{11}$-$A_{14}$ are N or $CR_{11}$, $CR_{12}$, $CR_{13}$, $CR_{14}$, respectively, with the proviso that no more than two of the four positions A can be simultaneously N;

$R_1$ is C(2-6)alkyl, C(3-6)cycloalkyl, C(3-6)cycloalkylC(1-3)alkyl, (di)C(3-6)cycloalkylamino or (di)(C(3-6)cycloalkylC(1-3)alkyl)amino, with all carbon atoms of alkyl groups optionally substituted with one or more F and all carbon atoms of cycloalkyl groups optionally substituted with one or more F or methyl;

$R_2$ and $R_3$ are independently H, F, methyl, ethyl, hydroxy, methoxy or $R_2$ and $R_3$ together is carbonyl, all alkyl groups, if present, optionally being substituted with one or more F;

$R_4$ is H or C(1-6)alkyl;

$R_5$ is H, hydroxyethyl, methoxyethyl, C(1-6)alkyl, C(6-10)aryl, C(6-10)arylC(1-3)alkyl, C(1-9)heteroaryl, C(1-9)heteroarylC(1-3)alkyl, C(3-6)cycloalkyl, C(3-6)cycloalkylC(1-3)alkyl, C(2-5)heterocycloalkyl or C(2-5)heterocycloalkyl-C(1-3)alkyl, all groups optionally substituted with one or more F, Cl, C(1-2)alkyl, C(1-2)alkoxy or cyano;

the sulfonyl group with $R_1$ is represented by one of $R_7$, $R_8$ or $R_9$;

the remaining $R_6$-$R_{14}$ are independently H, halogen, amino, C(1-3)alkoxy, (di)C(1-3)alkylamino or C(1-6)alkyl, all of the alkyl groups optionally being substituted with one or more F;

$R_{15}$ is H, C(1-6)alkyl, C(3-6)cycloalkyl, C(3-6)cycloalkylC(1-3)alkyl, C(6-10)aryl, C(6-10)arylC(1-3)alkyl, C(1-9)heteroaryl, C(1-9)heteroarylC(1-3)alkyl, C(2-5)heterocycloalkyl or C(2-5)heterocycloalkylC(1-3)alkyl, all groups optionally substituted with one or more F, Cl, C(1-2)alkyl, C(1-2)alkoxy or cyano;

and $R_{16}$ is C(1-6)alkyl, C(3-6)cycloalkyl, C(3-6)cycloalkylC(1-3)alkyl, C(6-10)aryl, C(6-10)arylC(1-3)alkyl, C(1-9)heteroaryl, C(1-9)heteroarylC(1-3)alkyl, C(2-5)heterocycloalkyl or C(2-5)heterocycloalkylC(1-3)alkyl, all groups optionally substituted with one or more F, Cl, C(1-2)alkyl, C(1-2)alkoxy or cyano.

The term C(1-6)alkyl as used herein means a branched or unbranched alkyl group having 1-6 carbon atoms, for example methyl, ethyl, propyl, isopropyl, butyl, tert-butyl, n-pentyl and n-hexyl. All carbon atoms may optionally be substituted with one or more halogen.

The term C(2-6)alkyl as used herein means a branched or unbranched alkyl group having 2-6 carbon atoms, for example ethyl, propyl, isopropyl, butyl, tert-butyl, n-pentyl and n-hexyl. All carbon atoms may optionally be substituted with one or more halogen.

The term C(1-4)alkyl as used herein means an alkyl group having 1-4 carbon atoms, i.e. methyl, ethyl, propyl, isopropyl, butyl, isobutyl, sec-butyl, or tert-butyl. All carbon atoms may optionally be substituted with one or more halogen.

The term C(2-4)alkyl as used herein means an alkyl group having 2-4 carbon atoms, i.e. ethyl, propyl, isopropyl, butyl, isobutyl, sec-butyl, or tert-butyl. All carbon atoms may optionally be substituted with one or more halogen.

The term C(1-3)alkyl as used herein means an alkyl group having 1-3 carbon atoms, i.e. methyl, ethyl, propyl or isopropyl. All carbon atoms may optionally be substituted with one or more halogen.

The term C(1-2)alkyl as used herein means an alkyl group having 1-2 carbon atoms i.e. methyl or ethyl. All carbon atoms may optionally be substituted with one or more halogen.

The term C(6-10)aryl as used herein means an aromatic hydrocarbon group having 6-10 carbon atoms, for example phenyl or naphthyl. The preferred aromatic hydrocarbon group is phenyl. All carbon atoms may optionally be substituted with one or more halogen.

The term C(6)aryl as used herein means an aromatic hydrocarbon group having 6 carbon atoms, i.e. phenyl. All carbon atoms may optionally be substituted with one or more halogen.

The term C(6-10)arylC(1-3)alkyl as used herein means an C(6-10)aryl group attached to a C(1-3)alkyl group, both with the same meaning as previously defined.

The term C(6)arylC(1-3)alkyl as used herein means an C(6)aryl group attached to a C(1-3)alkyl group, both with the same meaning as previously defined.

The term heteroatom as used herein refers to a nitrogen, sulphur or oxygen atom.

The term C(1-9)heteroaryl as used herein means an aromatic group having 1-9 carbon atoms and 1-4 heteroatoms, which may be attached via a nitrogen atom if feasible, or a carbon atom. Examples include imidazolyl, thiadiazolyl, pyridinyl, pyrimidinyl, furyl, pyrazolyl, isoxazolyl, tetrazolyl and quinolyl. All carbon atoms may optionally be substituted with one or more halogen or methyl.

The term C(3)heteroaryl as used herein means an aromatic group having 3 carbon atoms and 2 heteroatoms, which may be attached via a nitrogen atom if feasible, or a carbon atom. Examples include imidazolyl, pyrazolyl, and isoxazolyl. All carbon atoms may optionally be substituted with one or more halogen or methyl.

The term C(1-9)heteroarylC(1-3)alkyl as used herein means an C(1-9)heteroaryl group attached to a C(1-3)alkyl group, both with the same meaning as previously defined.

The term C(3-6)cycloalkyl as used herein means a saturated cyclic hydrocarbon having 3-6 carbon atoms, i.e. cyclopropyl, cyclobutyl, cyclopentyl or cyclohexyl. All carbon atoms may optionally be substituted with one or more halogen or methyl.

The term C(3-5)cycloalkyl as used herein means a saturated cyclic hydrocarbon having 3-5 carbon atoms, i.e. cyclopropyl, cyclobutyl or cyclopentyl. All carbon atoms may optionally be substituted with one or more halogen or methyl.

The term C(3-4)cycloalkyl as used herein means a saturated cyclic hydrocarbon having 3-4 carbon atoms, i.e. cyclopropyl or cyclobutyl. All carbon atoms may optionally be substituted with one or more halogen or methyl.

The term C(3-6)cycloalkylC(1-3)alkyl as used herein means an C(3-6)cycloalkyl group attached to an C(1-3)alkyl group, both with the same meaning as previously defined. An example is cyclopropylmethyl.

The term C(3-5)cycloalkylC(1-3)alkyl as used herein means an C(3-5)cycloalkyl group attached to an C(1-3)alkyl group, both with the same meaning as previously defined.

The term cyclopropylmethyl as used herein means a methyl group substituted with cyclopropyl. All carbon atoms are optionally substituted with one or more halogen or methyl.

The term C(2-5)heterocycloalkyl as used herein means a saturated cyclic hydrocarbon having 2-5 carbon atoms and 1-3 heteroatoms, which may be attached via a nitrogen atom if feasible, or a carbon atom. Examples include piperazinyl, pyrazolidilyl, piperidinyl, morpholinyl and pyrrolidinyl. All carbon atoms may optionally be substituted with one or more halogen or methyl.

The term C(2-5)heterocycloalkylC(1-3)alkyl as used herein means an C(2-5)heterocycloalkyl group attached to an C(1-3)alkyl group, both with the same meaning as previously defined.

The term amino as used herein refers to an $NH_2$ group.

The term (di)C(1-6)alkylamino as used herein means an amino group, which is monosubstituted or disubstituted with a C(1-6)alkyl group, the latter having the same meaning as previously defined.

It is to be understood that in the (di)C(1-6)alkylamino groups containing two C(1-6)alkyl groups, one of the C(1-6)alkyl groups can be replaced by a C(3-6)cycloalkyl group as previously defined.

The term (di)C(1-3)alkylamino as used herein means an amino group, which is monosubstituted or disubstituted with a C(1-3)alkyl group, the latter having the same meaning as previously defined.

The term (di)C(1-2)alkylamino as used herein means an amino group, which is monosubstituted or disubstituted with a C(1-2)alkyl group, the latter having the same meaning as previously defined. An example is dimethylamino.

The term (di)C(3-6)cycloalkylamino as used herein means an amino group, which is monosubstituted or disubstituted with a C(3-6)cycloalkyl group, the latter having the same meaning as previously defined. An example is cyclopropylamino.

The term (di)C(3-4)cycloalkylamino as used herein means an amino group, which is monosubstituted or disubstituted with a C(3-4)cycloalkyl group, the latter having the same meaning as previously defined.

The term cyclopropylamino means an amino group substituted with cyclopropyl. All carbon atoms may optionally be substituted with one or more halogen or methyl.

The term (di)(C(3-6)cycloalkylC(1-3)alkyl)amino as used herein means an amino group, which is monosubstituted or disubstituted with a C(3-6)cycloalkylC(1-3)alkyl group as previously defined.

It is to be understood that in the (di)(C(3-6)cycloalkylC(1-3)alkyl)amino groups containing two C(3-6)cycloalkylC(1-3)alkyl groups, one of the C(3-6)cycloalkylC(1-3)alkyl groups can be replaced by a C(1-6)alkyl or a C(3-6)cycloalkyl group, both as previously defined.

The term C(1-3)alkoxy means an alkoxy group having 1-3 carbon atoms, the alkyl moiety being branched or unbranched. All carbon atoms are optionally substituted with one or more F.

The term C(1-2)alkoxy means an alkoxy group having 1-2 carbon atoms. Preferred is methoxy. All carbon atoms may optionally be substituted with one or more F.

The term halogen as used herein means Cl or F.

In the above definitions with multifunctional groups, the attachment point is at the last group.

When, in the definition of a substituent, is indicated that "all of the alkyl groups" of said substituent are optionally substituted, this also includes the alkyl moiety of an alkoxy group.

The term "substituted" means that one or more hydrogens on the designated atom/atoms is/are replaced with a selection from the indicated group, provided that the designated atom's normal valency under the existing circumstances is not exceeded, and that the substitution results in a stable compound. Combinations of substituents and/or variables are permissible only if such combinations result in stable compounds. "Stable compound" or "stable structure" is defined as a compound or structure that is sufficiently robust to survive isolation to a useful degree of purity from a reaction mixture, and formulation into an efficacious therapeutic agent.

The term "optionally substituted" means optional substitution with the specified groups, radicals or moieties.

The term pharmaceutically acceptable salt represents those salts which are, within the scope of medical judgment, suitable for use in contact for the tissues of humans and lower animals without undue toxicity, irritation, allergic response and the like, and are commensurate with a reasonable benefit/risk ratio. Pharmaceutically acceptable salts are well known in the art. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. The acid function can be reacted with an organic or a mineral base, like sodium hydroxide, potassium hydroxide or lithium hydroxide.

According to the present invention, distinguished compounds are those of Formula I in which:
- $A_{11}$-$A_{14}$ are N or $CR_{11}$, $CR_{12}$, $CR_{13}$, $CR_{14}$, respectively, with the proviso that no more than two of the four positions A can be simultaneously N;
- $R_1$ is C(2-6)alkyl, C(3-6)cycloalkylC(1-3)alkyl or (di)C(3-6)cycloalkylamino, with all carbon atoms of alkyl groups optionally substituted with one or more F and all carbon atoms of cycloalkyl groups optionally substituted with one or more F or methyl;
- $R_2$ and $R_3$ are independently H, methyl, or $R_2$ and $R_3$ together is carbonyl, all alkyl groups, if present, optionally being substituted with one or more F;
- $R_4$ is H;
- $R_5$ is H, hydroxyethyl, methoxyethyl, C(1-6)alkyl, C(6-10)arylC(1-3)alkyl, C(2-5)heterocycloalkyl or C(2-5)heterocycloalkyl-C(1-3)alkyl, all groups optionally substituted with one or more F, C(1-2)alkyl, C(1-2)alkoxy or cyano;
- the sulfonyl group with $R_1$ is represented by $R_8$;
- the remaining $R_6$-$R_{14}$ are independently H, halogen, C(1-3)alkoxy or C(1-6)alkyl, all of the alkyl groups optionally being substituted with one or more F;
- $R_{15}$ is C(1-6)alkyl optionally substituted with one or more F, or C(1-9)heteroaryl substituted with one C(1-2)alkyl;
- and $R_{16}$ is C(1-6)alkyl, C(3-6)cycloalkyl, C(3-6)cycloalkylC(1-3)alkyl, C(6-10)aryl, C(6-10)arylC(1-3)alkyl, C(2-5)heterocycloalkyl or C(2-5)heterocycloalkyl-C(1-3)alkyl, all groups optionally substituted with one or more F.

According to the present invention, distinguished compounds are those of Formula I in which:
- $A_{11}$-$A_{14}$ is $CR_{11}$, $CR_{12}$, $CR_{13}$, $CR_{14}$;
- $R_1$ is C(2-6)alkyl, C(3-6)cycloalkylC(1-3)alkyl or (di)C(3-6)cycloalkylamino, with all carbon atoms of alkyl groups optionally substituted with one or more F and all carbon atoms of cycloalkyl groups optionally substituted with one or more F or methyl;
- $R_2$ and $R_3$ are independently H, methyl, or $R_2$ and $R_3$ together is carbonyl, all alkyl groups, if present, optionally being substituted with one or more F;
- $R_4$ is H;
- $R_5$ is H, hydroxyethyl, methoxyethyl, C(1-6)alkyl, C(6-10)arylC(1-3)alkyl, C(2-5)heterocycloalkyl or C(2-5)heterocycloalkyl-C(1-3)alkyl, all groups optionally substituted with one or more F, C(1-2)alkyl, C(1-2)alkoxy or cyano;
- the sulfonyl group with $R_1$ is represented by $R_8$;
- the remaining $R_6$-$R_{14}$ are independently H, halogen, C(1-3)alkoxy or C(1-6)alkyl, all of the alkyl groups optionally being substituted with one or more F;
- $R_{15}$ is C(1-6)alkyl optionally substituted with one or more F, or C(1-9)heteroaryl substituted with one C(1-2)alkyl;
- and $R_{16}$ is C(1-6)alkyl, C(3-6)cycloalkyl, C(3-6)cycloalkylC(1-3)alkyl, C(6-10)aryl, C(6-10)arylC(1-3)alkyl, C(2-5)heterocycloalkyl or C(2-5)heterocycloalkyl-C(1-3)alkyl, all groups optionally substituted with one or more F.

According to the present invention, distinguished compounds are those of Formula I in which:
one or two positions A in $A_{11}$-$A_{14}$ are N, the remaining positions A in $A_{11}$-$A_{14}$ are $CR_{11}$, $CR_{12}$, $CR_{13}$ or $CR_{14}$, respectively;
- $R_1$ is C(2-6)alkyl, C(3-6)cycloalkylC(1-3)alkyl or (di)C(3-6)cycloalkylamino, with all carbon atoms of alkyl groups optionally substituted with one or more F and all carbon atoms of cycloalkyl groups optionally substituted with one or more F or methyl;
- $R_2$ and $R_3$ are independently H, methyl, or $R_2$ and $R_3$ together is carbonyl;
- $R_4$ is H;
- $R_5$ is H, hydroxyethyl, methoxyethyl, C(1-6)alkyl, C(6-10)arylC(1-3)alkyl, C(2-5)heterocycloalkyl or C(2-5)heterocycloalkyl-C(1-3)alkyl, all groups optionally substituted with one or more F, C(1-2)alkyl, C(1-2)alkoxy or cyano;
- the sulfonyl group with $R_1$ is represented by $R_8$;
- the remaining $R_6$-$R_{14}$ are independently H, halogen, C(1-3)alkoxy or C(1-6)alkyl, all of the alkyl groups optionally being substituted with one or more F;
- $R_{15}$ is C(1-6)alkyl, all alkyl groups optionally substituted with one or more F;
- and $R_{16}$ is C(1-6)alkyl, C(3-6)cycloalkyl, C(3-6)cycloalkylC(1-3)alkyl, C(6-10)aryl, C(6-10)arylC(1-3)alkyl, C(2-5)heterocycloalkyl or C(2-5)heterocycloalkyl-C(1-3)alkyl, all groups optionally substituted with one or more F.

According to the present invention, distinguished compounds are those of Formula I in which:
- $A_{11}$-$A_{14}$ is $CR_{11}$, $CR_{12}$, $CR_{13}$, $CR_{14}$;
- $R_1$ is C(2-6)alkyl, C(3-6)cycloalkylC(1-3)alkyl, (di)C(3-6)cycloalkylamino; $R_2$ and $R_3$ are independently H or methyl;
- $R_4$ is H;
- $R_5$ is H, C(1-6)alkyl or C(6-10)arylC(1-3)alkyl;
- the sulfonyl group with $R_1$ is represented by $R_8$;
- the remaining $R_6$-$R_{14}$ are independently H or C(1-6)alkyl;
- $R_{15}$ is C(1)alkyl optionally substituted with one or more F, or C(3)heteroaryl substituted with one methyl;
- and $R_{16}$ is C(1-6)alkyl, C(3-6)cycloalkyl, C(6-10)aryl or C(6-10)arylC(1-3)alkyl, all groups optionally substituted with one or more F.

According to the present invention, distinguished compounds are those of Formula I in which:
- $A_{11}$-$A_{14}$ is $CR_{11}$, $CR_{12}$, $CR_{13}$, $CR_{14}$;
- $R_1$ is ethyl, cyclopropylmethyl, cyclopropylamino;
- $R_2$ and $R_3$ are independently H or methyl;
- $R_4$ is H;
- $R_5$ is H, methyl, ethyl, propyl, isopropyl, butyl or benzyl;
- the sulfonyl group with $R_1$ is represented by $R_8$;
- the remaining $R_6$-$R_{14}$ are independently H or methyl;
- $R_{15}$ is methyl, $CF_3$ or 5-methyl-isoxazol-3-yl;
- and $R_{16}$ is methyl, $CHF_2$, $CF_3$, ethyl, 2,2-dimethylpropyl, propyl, isopropyl, butyl, isobutyl, tertbutyl, cyclopropyl, cyclopentyl, phenyl or benzyl.

According to the present invention, distinguished compounds are those of Formula I in which:
- $A_{11}$ or $A_{14}$ is N, the remaining position A being $CR_{11}$ or $CR_{14}$;
- $A_{12}$ and $A_{13}$ are respectively $CR_{12}$ and $CR_{13}$;
- $R_1$ is C(3-6)cycloalkylC(1-3)alkyl;
- $R_2$ and $R_3$ are independently H;
- $R_4$ is H;
- $R_5$ is H;
- the sulfonyl group with $R_1$ is represented by $R_8$;
- the remaining $R_6$-$R_{14}$ are H;
- $R_{15}$ and $R_{16}$ are C(1)alkyl, with all carbon atoms of alkyl groups optionally substituted with one or more F.

According to the present invention, distinguished compounds are those of Formula I in which:
- $A_{11}$ or $A_{14}$ is N, the remaining position A being $CR_{11}$ or $CR_{14}$;

$A_{12}$ and $A_{13}$ are respectively $CR_{12}$ and $CR_{13}$;
$R_1$ is cyclopropylmethyl; $R_2$ and $R_3$ are independently H;
$R_4$ is H;
$R_5$ is H;
the sulfonyl group with $R_1$ is represented by $R_8$;
the remaining $R_6$-$R_{14}$ are independently H or methyl;
$R_{15}$ and $R_{16}$ are $CF_3$.

The invention also relates to a compound according to Formula I wherein $R_1$ is C(2-4)alkyl, C(3-5)cycloalkylC(1-3)alkyl or (di)C(3-4)cycloalkylamino.

In one embodiment the invention also relates to a compound according to Formula I wherein $R_1$ is (di)C(3-4)cycloalkylamino.

In one embodiment the invention relates to a compound according to Formula I wherein $R_1$ is ethyl.

In one embodiment the invention relates to a compound according to Formula I wherein $R_1$ is cyclopropylamino.

In one embodiment the invention relates to a compound according to Formula I wherein $R_1$ is cyclopropylmethyl.

The invention also relates to a compound according to Formula I wherein $R_2$ and $R_3$ independently are H or methyl.

In one embodiment the invention relates to a compound according to Formula I wherein $R_2$ and $R_3$ independently are H.

The invention also relates to a compound according to Formula I wherein $R_4$ is H.

The invention also relates to a compound according to Formula I wherein $R_5$ is H, hydroxyethyl, methoxyethyl, C(1-6)alkyl, C(6-10)arylC(1-3)alkyl, C(2-5)heterocycloalkyl or C(2-5)heterocycloalkyl-C(1-3)alkyl, all groups optionally substituted with one or more F, C(1-2)alkyl, C(1-2)alkoxy or cyano; In one embodiment, $R_5$ in Formula I is H, C(1-6)alkyl or C(6-10)arylC(1-3)alkyl.

In one embodiment, $R_5$ in Formula I is H, methyl, ethyl, propyl, isopropyl, butyl or benzyl.

In one embodiment $R_5$ in Formula I is H.

In one embodiment, $R_5$ in Formula I is C(1-6)alkyl.

In one embodiment $R_5$ in Formula I is C(6-10)arylC(1-3)alkyl.

The invention also relates to a compound according to Formula I wherein one of the groups $R_7$, $R_8$, $R_9$ is the sulfonyl group with $R_1$ attached to it and the others including $R_6$ and $R_{10}$ are independently H or C(1-6)alkyl.

In one embodiment the sulfonyl group is represented by $R_8$, i.e. the sulfonyl group is attached at the para position of the aryl ring.

The invention also relates to a compound according to Formula I wherein $R_{11}$-$R_{14}$ are independently H, halogen, methyl or methoxy.

In one embodiment the invention relates to a compound according to Formula I wherein $R_{11}$-$R_{14}$ are independently H or methyl.

In one embodiment the invention relates to a compound according to Formula I wherein $A_{11}$-$A_{14}$ are carbon atoms.

In one embodiment the invention relates to a compound according to Formula I wherein $A_{11}$ or $A_{14}$ is nitrogen, the remaining position A is $CR_{11}$ or $CR_{14}$.

The invention also relates to a compound according to Formula I wherein
$R_{15}$ is C(1-6)alkyl optionally substituted with one or more F or C(1-9)heteroaryl substituted with one C(1-2)alkyl;
and $R_{16}$ is C(1-6)alkyl, C(3-6)cycloalkyl, C(3-6)cycloalkylC(1-3)alkyl, C(6-10)aryl, C(6-10)arylC(1-3)alkyl, C(2-5)heterocycloalkyl or C(2-5)heterocycloalkylC(1-3)alkyl, all groups optionally substituted with one or more F.

In one embodiment the invention relates to a compound according to Formula I wherein
$R_{15}$ is methyl optionally substituted with one or more F, or C(3)heteroaryl substituted with one methyl;
and $R_{16}$ is C(1-6)alkyl, C(3-6)cycloalkyl, C(6-10)aryl or C(6-10)arylC(1-3)alkyl, all groups optionally substituted with one or more F.

In one embodiment the invention relates to a compound according to Formula I wherein
$R_{15}$ is methyl, $CF_3$, or 5-methyl-isoxazol-3-yl.
and $R_{16}$ is methyl, $CHF_2$, $CF_3$, ethyl, 2,2-dimethylpropyl, propyl, isopropyl, butyl, isobutyl, tertbutyl, cyclopropyl, cyclopentyl, phenyl or benzyl.

In one embodiment the invention relates to a compound according to Formula I wherein both $R_{15}$ and $R_{16}$ is $CF_3$.

In one embodiment the invention relates to a compound according to Formula I wherein either $R_{15}$ or $R_6$ is $CF_3$.

In one embodiment the invention relates to a compound according to Formula I wherein $R_{15}$ is $CF_3$ and $R_{16}$ is C(1-6)alkyl, C(3-6)cycloalkyl, C(6-10)aryl or C(6-10)arylC(1-3)alkyl, all groups optionally substituted with one or more F.

In one embodiment the invention relates to a compound according to Formula I wherein $R_{15}$ is $CF_3$ and $R_{16}$ is methyl, $CHF_2$, $CF_3$, ethyl, 2,2-dimethylpropyl, propyl, isopropyl, butyl, isobutyl, cyclopropyl, cyclopentyl, phenyl or benzyl.

In one embodiment the invention relates to a compound according to Formula I wherein $R_{15}$ is $CF_3$ and $R_{16}$ is C(1-6)alkyl, with all carbon atoms of the alkyl group optionally substituted with one or more F.

In one embodiment the invention relates to a compound according to Formula I wherein $R_{15}$ is $CF_3$ and $R_{16}$ is methyl, $CHF_2$, $CF_3$, ethyl, 2,2-dimethylpropyl, propyl, isopropyl, butyl, isobutyl.

In one embodiment the invention relates to a compound according to Formula I wherein $R_{15}$ is $CF_3$ and $R_{16}$ is C(3-6)cycloalkyl.

In one embodiment the invention relates to a compound according to Formula I wherein $R_{15}$ is $CF_3$ and $R_{16}$ is cyclopropyl or cyclopentyl.

In one embodiment the invention relates to a compound according to Formula I wherein $R_{15}$ is $CF_3$ and $R_{16}$ is C(6-10)aryl.

In one embodiment the invention relates to a compound according to Formula I wherein $R_{15}$ is $CF_3$ and $R_{16}$ is phenyl.

In one embodiment the invention relates to a compound according to Formula I wherein $R_{15}$ is $CF_3$ and $R_{16}$ is or C(6-10)arylC(1-3)alkyl.

In one embodiment the invention relates to a compound according to Formula I wherein $R_{15}$ is $CF_3$ and $R_{16}$ is benzyl.

The invention also relates to a compound according to Formula I wherein $R_5$ is H and $R_{15}$ is $CF_3$ and $R_{16}$ is C(1-6)alkyl, C(3-6)cycloalkyl, C(6-10)aryl or C(6-10)arylC(1-3)alkyl.

In one embodiment the invention relates to a compound according to Formula I wherein $R_5$ is H, $R_{15}$ is $CF_3$ and $R_{16}$ is C(1-6)alkyl, with all carbon atoms of the alkyl group optionally substituted with one or more F.

In one embodiment the invention relates to a compound according to Formula I wherein $R_5$ is H, $R_{15}$ is $CF_3$ and $R_{16}$ is methyl, $CHF_2$, $CF_3$, ethyl, 2,2-dimethylpropyl, propyl, isopropyl, butyl, isobutyl.

In one embodiment the invention relates to a compound according to Formula I wherein $R_5$ is H and both $R_{15}$ and $R_{16}$ are $CF_3$.

In one embodiment the invention relates to a compound according to Formula I wherein $R_5$ is H, $R_{15}$ is $CF_3$ and $R_{16}$ is C(6-10)aryl.

In one embodiment the invention relates to a compound according to Formula I wherein $R_5$ is H, $R_{15}$ is $CF_3$ and $R_{16}$ is phenyl.

In one embodiment the invention relates to a compound according to Formula I wherein $R_5$ is H, $R_{15}$ is $CF_3$ and $R_{16}$ is C(3-6)cycloalkyl.

In one embodiment the invention relates to a compound according to Formula I wherein $R_5$ is H, $R_{15}$ is $CF_3$ and $R_{16}$ is cyclopropyl or cyclopentyl.

In one embodiment the invention relates to a compound according to Formula I wherein $R_5$ is H, $R_{15}$ is $CF_3$ and $R_{16}$ is C(6-10)arylC(1-3)alkyl.

In one embodiment the invention relates to a compound according to Formula I $R_5$ is H, $R_{15}$ is $CF_3$ and $R_{16}$ is benzyl.

The invention also relates to those compounds wherein all specific definitions for $A_{11}$ through $A_{14}$, $R_1$ through $R_{16}$, and all substituent groups in the various aspects of the inventions defined here above occur in any combination within the definition of the compound of Formula I.

In another aspect the invention relates to compounds of Formula I which have a pIC50 of 5 or higher. In yet another aspect the invention relates to compounds according to Formula I with a pIC50 of more than 6. In yet another aspect the invention relates to compounds according to Formula I with a pIC50 of more than 7.

In yet another aspect the invention resides in the compounds according to Formula I selected as described in examples 1-38.

Among the compounds according to the invention, mention may be made especially of the compounds below:

| N° | Structure | IUPAC name |
| --- | --- | --- |
| 1<br>(−)-1<br>(+)-1 | 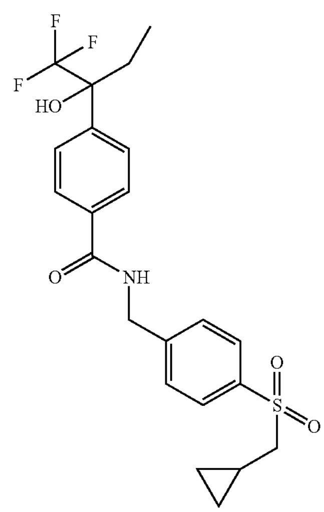 [SMILES: CCC(O)(c1ccc(C(=O)NCc2ccc(S(=O)(=O)CC3CC3)cc2)cc1)C(F)(F)F] | 1: N-[[4-(cyclopropylmethylsulfonyl)phenyl]methyl]-4-[1-hydroxy-1-(trifluoromethyl)propyl]benzamide (racemate)<br>(−)-1: (−)-N-[[4-(cyclopropylmethylsulfonyl)phenyl]methyl]-4-[1-hydroxy-1-(trifluoromethyl)propyl]benzamide<br>(+)-1: (+)-N-[[4-(cyclopropylmethylsulfonyl)phenyl]methyl]-4-[1-hydroxy-1-(trifluoromethyl)propyl]benzamide |
| 2 | 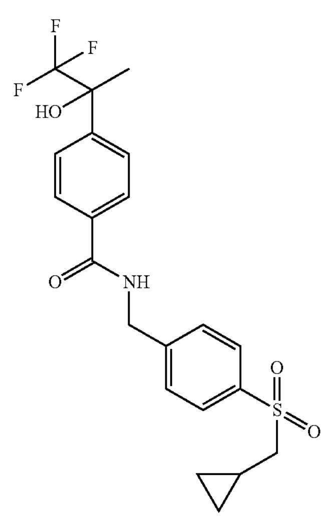 [SMILES: CC(O)(c1ccc(C(=O)NCc2ccc(S(=O)(=O)CC3CC3)cc2)cc1)C(F)(F)F] | N-[[4-(cyclopropylmethylsulfonyl)phenyl]methyl]-4-(2,2,2-trifluoro-1-hydroxy-1-methyl-ethyl)benzamide |

-continued

| N° | Structure | IUPAC name |
|---|---|---|
| 3 | 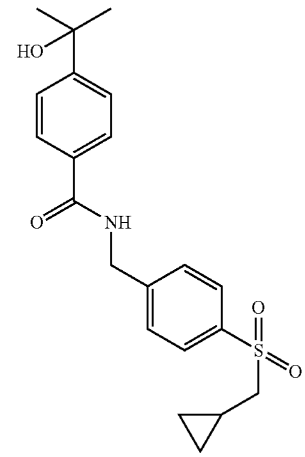 [SMILES: CC(C)(O)c1ccc(C(=O)NCc2ccc(S(=O)(=O)CC3CC3)cc2)cc1] | N-[[4-(cyclopropylmethylsulfonyl)phenyl]methyl]-4-(1-hydroxy-1-methyl-ethyl)benzamide |
| 4 | 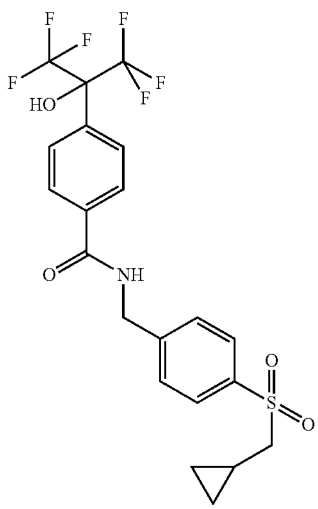 [SMILES: O=C(NCc1ccc(S(=O)(=O)CC2CC2)cc1)c1ccc(C(O)(C(F)(F)F)C(F)(F)F)cc1] | N-[[4-(cyclopropylmethylsulfonyl)phenyl]methyl]-4-[2,2,2-trifluoro-1-hydroxy-1-(trifluoromethyl)ethyl]benzamide |
| 5 | 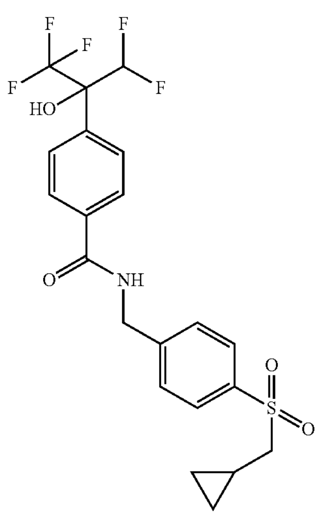 [SMILES: O=C(NCc1ccc(S(=O)(=O)CC2CC2)cc1)c1ccc(C(O)(C(F)F)C(F)(F)F)cc1] | N-[[4-(cyclopropylmethylsulfonyl)phenyl]methyl]-4-[1-(difluoromethyl)-2,2,2-trifluoro-1-hydroxy-ethyl]benzamide |

| N° | Structure | IUPAC name |
|---|---|---|
| 6 | 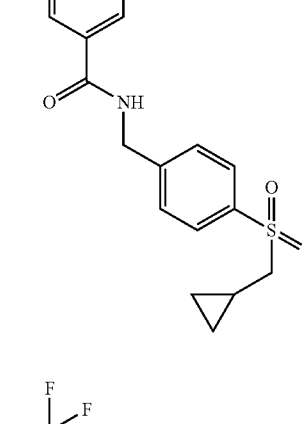 | N-[[4-(cyclopropylmethylsulfonyl)phenyl]methyl]-4-[1-hydroxy-1-(trifluoromethyl)butyl]benzamide |
| 7 | 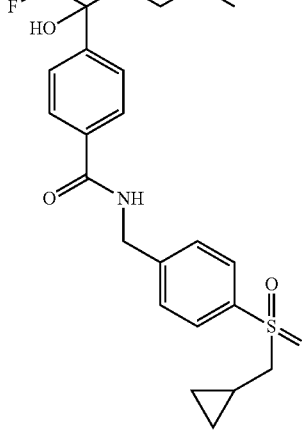 | N-[[4-(cyclopropylmethylsulfonyl)phenyl]methyl]-4-[1-hydroxy-1-(trifluoromethyl)pentyl]benzamide |
| 8 | 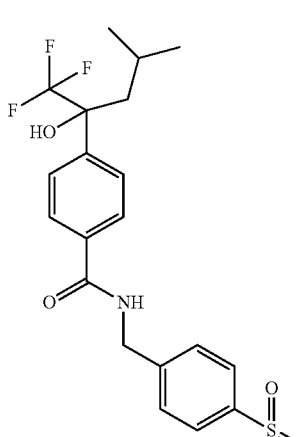 | N-[[4-(cyclopropylmethylsulfonyl)phenyl]methyl]-4-[1-hydroxy-3,3-dimethyl-1-(trifluoromethyl)butyl]benzamide |

| N° | Structure | IUPAC name |
|---|---|---|
| 9 | 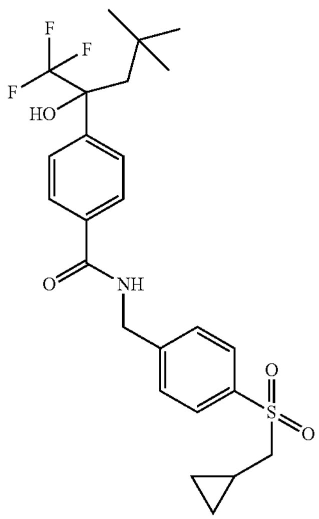 [SMILES: CC(C)(C)CC(O)(c1ccc(C(=O)NCc2ccc(S(=O)(=O)CC3CC3)cc2)cc1)C(F)(F)F] | N-[[4-(cyclopropylmethylsulfonyl)phenyl]methyl]-4-[1-hydroxy-3,3-dimethyl-1-(trifluoromethyl)butyl]benzamide |
| 10 | 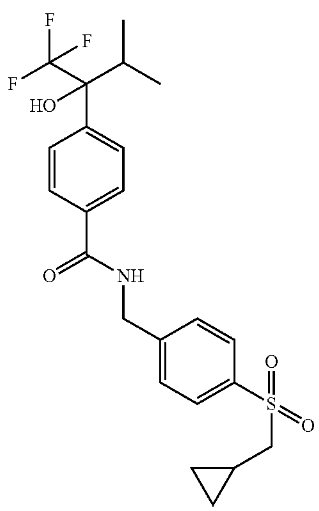 [SMILES: CC(C)C(O)(c1ccc(C(=O)NCc2ccc(S(=O)(=O)CC3CC3)cc2)cc1)C(F)(F)F] | N-[[4-(cyclopropylmethylsulfonyl)phenyl]methyl]-4-[1-hydroxy-2-methyl-1-(trifluoromethyl)propyl]benzamide |
| 11 | 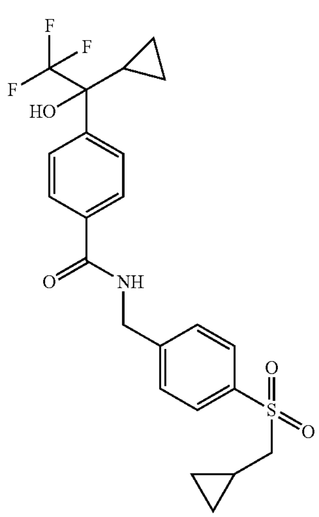 [SMILES: O=C(NCc1ccc(S(=O)(=O)CC2CC2)cc1)c1ccc(C(O)(C2CC2)C(F)(F)F)cc1] | N-[[4-(cyclopropylmethylsulfonyl)phenyl]methyl]-4-(1-cyclopropyl-2,2,2-trifluoro-1-hydroxy-ethyl)benzamide |

-continued
| N° | Structure | IUPAC name |
|---|---|---|
| 12 | 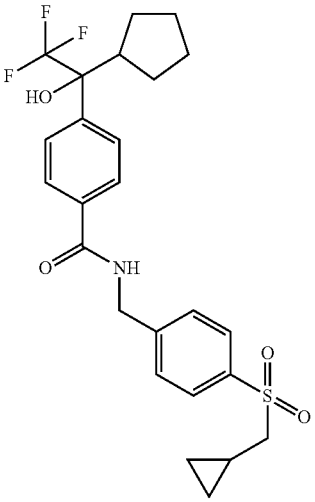 [SMILES: O=C(NCc1ccc(S(=O)(=O)CC2CC2)cc1)c1ccc(C(O)(C2CCCC2)C(F)(F)F)cc1] | 4-(1-cyclopentyl-2,2,2-trifluoro-1-hydroxy-ethyl)-N-[[4-(cyclopropylmethylsulfonyl)phenyl]methyl]benzamide |
| 13 | 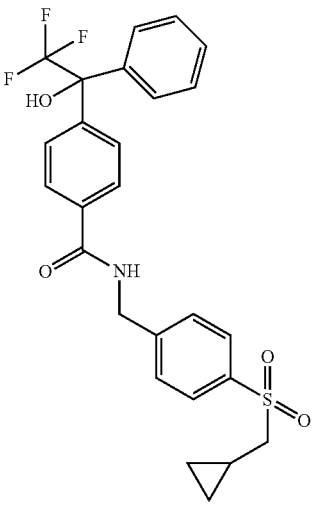 [SMILES: O=C(NCc1ccc(S(=O)(=O)CC2CC2)cc1)c1ccc(C(O)(c2ccccc2)C(F)(F)F)cc1] | N-[[4-(cyclopropylmethylsulfonyl)phenyl]methyl]-4-(2,2,2-trifluoro-1-hydroxy-1-phenyl-ethyl)benzamide |
| 14 | 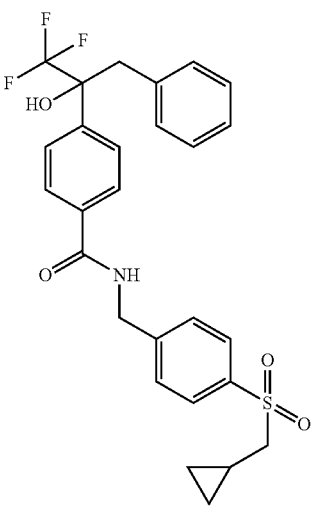 [SMILES: O=C(NCc1ccc(S(=O)(=O)CC2CC2)cc1)c1ccc(C(O)(Cc2ccccc2)C(F)(F)F)cc1] | 4-(1-benzyl-2,2,2-trifluoro-1-hydroxy-ethyl)-N-[[4-(cyclopropylmethylsulfonyl)phenyl]methyl]benzamide |

| N° | Structure | IUPAC name |
|---|---|---|
| 15 | 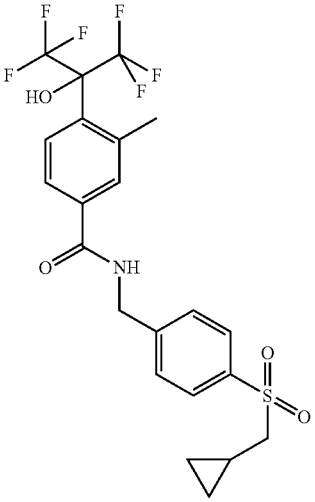 [SMILES: Cc1cc(C(=O)NCc2ccc(S(=O)(=O)CC3CC3)cc2)ccc1C(O)(C(F)(F)F)C(F)(F)F] | N-[[4-(cyclopropylmethylsulfonyl)phenyl]methyl]-3-methyl-4-[2,2,2-trifluoro-1-hydroxy-1-(trifluoromethyl)ethyl]benzamide |
| 16 | 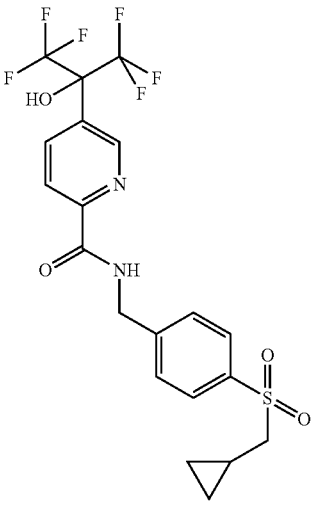 [SMILES: O=C(NCc1ccc(S(=O)(=O)CC2CC2)cc1)c1ccc(C(O)(C(F)(F)F)C(F)(F)F)cn1] | N-[[4-(cyclopropylmethylsulfonyl)phenyl]methyl]-5-[2,2,2-trifluoro-1-hydroxy-1-(trifluoromethyl)ethyl]pyridine-2-carboxamide |
| 17 | 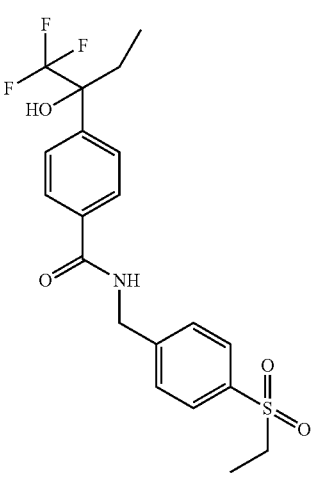 [SMILES: CCC(O)(c1ccc(C(=O)NCc2ccc(S(=O)(=O)CC)cc2)cc1)C(F)(F)F] | N-[(4-ethylsulfonylphenyl)methyl]-4-[1-hydroxy-1-(trifluoromethyl)propyl]benzamide |

| N° | Structure | IUPAC name |
|---|---|---|
| 18 | 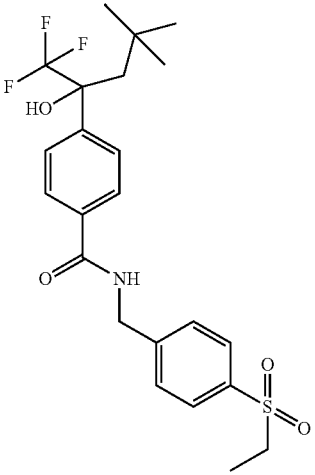 [SMILES: CCS(=O)(=O)c1ccc(CNC(=O)c2ccc(C(O)(CC(C)(C)C)C(F)(F)F)cc2)cc1] | N-[(4-ethylsulfonylphenyl)methyl]-4-[1-hydroxy-3,3-dimethyl-1-(trifluoromethyl)butyl]benzamide |
| 19 | 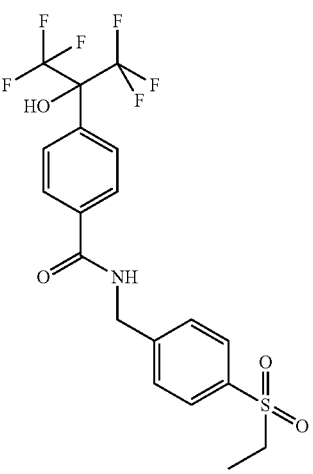 [SMILES: CCS(=O)(=O)c1ccc(CNC(=O)c2ccc(C(O)(C(F)(F)F)C(F)(F)F)cc2)cc1] | N-[(4-ethylsulfonylphenyl)methyl]-4-[2,2,2-trifluoro-1-hydroxy-1-(trifluoromethyl)ethyl]benzamide |
| 20 | 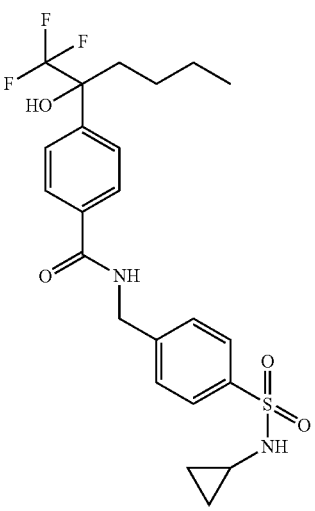 [SMILES: CCCCC(O)(c1ccc(C(=O)NCc2ccc(S(=O)(=O)NC3CC3)cc2)cc1)C(F)(F)F] | N-[[4-(cyclopropylsulfamoyl)phenyl]methyl]-4-[1-hydroxy-1-(trifluoromethyl)pentyl]benzamide |

-continued
| N° | Structure | IUPAC name |
|---|---|---|
| 21 | 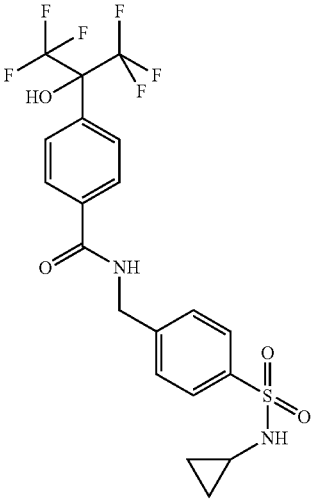 [SMILES: O=C(NCc1ccc(S(=O)(=O)NC2CC2)cc1)c1ccc(C(O)(C(F)(F)F)C(F)(F)F)cc1] | N-[[4-(cyclopropylsulfamoyl)phenyl]methyl]-4-[2,2,2-trifluoro-1-hydroxy-1-(trifluoromethyl)ethyl]benzamide |
| 22 | 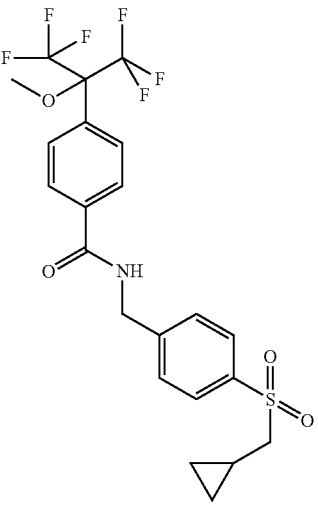 [SMILES: COC(c1ccc(C(=O)NCc2ccc(S(=O)(=O)CC3CC3)cc2)cc1)(C(F)(F)F)C(F)(F)F] | N-[[4-(cyclopropylmethylsulfonyl)phenyl]methyl]-4-[2,2,2-trifluoro-1-methoxy-1-(trifluoromethyl)ethyl]benzamide |
| 23 | 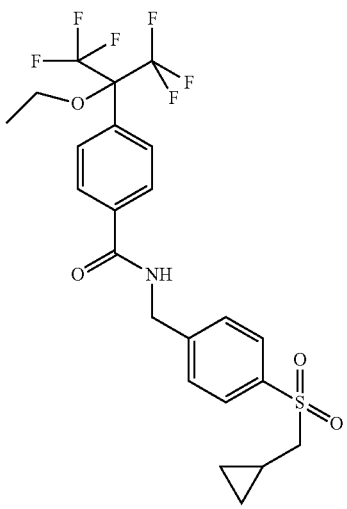 [SMILES: CCOC(c1ccc(C(=O)NCc2ccc(S(=O)(=O)CC3CC3)cc2)cc1)(C(F)(F)F)C(F)(F)F] | N-[[4-(cyclopropylmethylsulfonyl)phenyl]methyl]-4-[1-ethoxy-2,2,2-trifluoro-1-(trifluoromethyl)ethyl]benzamide |

-continued

| N° | Structure | IUPAC name |
|---|---|---|
| 24 | 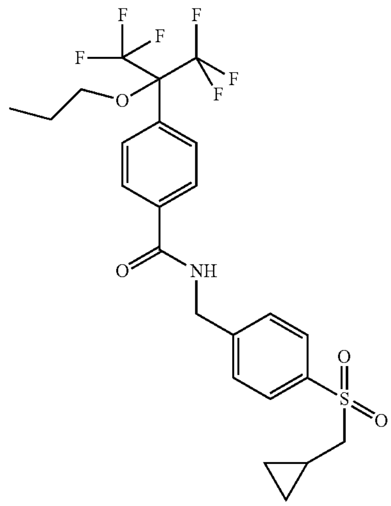 [SMILES: CCCOC(c1ccc(C(=O)NCc2ccc(S(=O)(=O)CC3CC3)cc2)cc1)(C(F)(F)F)C(F)(F)F] | N-[[4-(cyclopropylmethylsulfonyl)phenyl]methyl]-4-[2,2,2-trifluoro-1-propoxy-1-(trifluoromethyl)ethyl]benzamide |
| 25 | 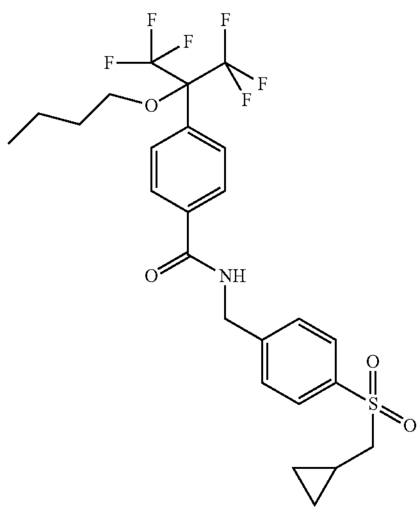 [SMILES: CCCCOC(c1ccc(C(=O)NCc2ccc(S(=O)(=O)CC3CC3)cc2)cc1)(C(F)(F)F)C(F)(F)F] | 4-[1-butoxy-2,2,2-trifluoro-1-(trifluoromethyl)ethyl]-N-[[4-(cyclopropylmethylsulfonyl)phenyl]methyl]benzamide |
| 26 | 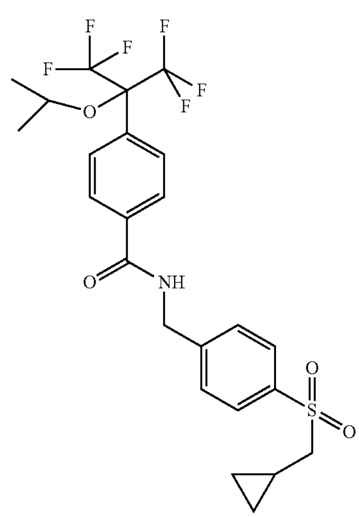 [SMILES: CC(C)OC(c1ccc(C(=O)NCc2ccc(S(=O)(=O)CC3CC3)cc2)cc1)(C(F)(F)F)C(F)(F)F] | N-[[4-(cyclopropylmethylsulfonyl)phenyl]methyl]-4-[2,2,2-trifluoro-1-isopropoxy-1-(trifluoromethyl)ethyl]benzamide |

-continued

| N° | Structure | IUPAC name |
|---|---|---|
| 27 | 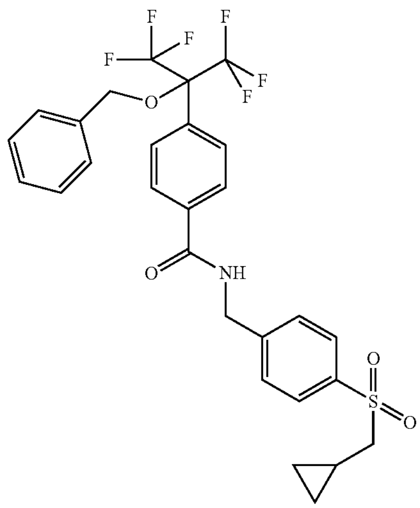 [SMILES: O=C(NCc1ccc(S(=O)(=O)CC2CC2)cc1)c1ccc(C(OCc2ccccc2)(C(F)(F)F)C(F)(F)F)cc1] | 4-[1-benzyloxy-2,2,2-trifluoro-1-(trifluoromethyl)ethyl]-N-[[4-(cyclopropylmethylsulfonyl)phenyl]methyl]benzamide |
| 28 | 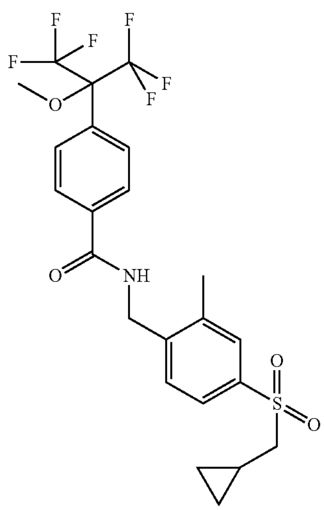 [SMILES: COC(c1ccc(C(=O)NCc2ccc(S(=O)(=O)CC3CC3)cc2C)cc1)(C(F)(F)F)C(F)(F)F] | N-[[4-(cyclopropylmethylsulfonyl)-2-methyl-phenyl]methyl]-4-[2,2,2-trifluoro-1-methoxy-1-(trifluoromethyl)ethyl]benzamide |
| 29 | 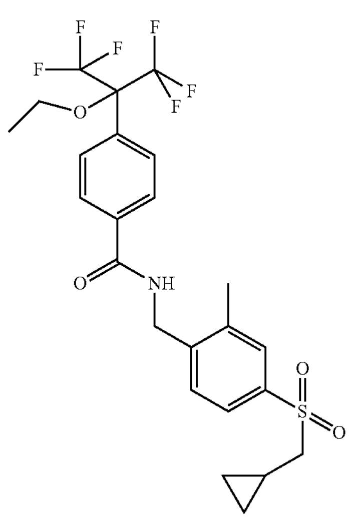 [SMILES: CCOC(c1ccc(C(=O)NCc2ccc(S(=O)(=O)CC3CC3)cc2C)cc1)(C(F)(F)F)C(F)(F)F] | N-[[4-(cyclopropylmethylsulfonyl)-2-methyl-phenyl]methyl]-4-[1-ethoxy-2,2,2-trifluoro-1-(trifluoromethyl)ethyl]benzamide |

-continued
| N° | Structure | IUPAC name |
|---|---|---|
| 30 | 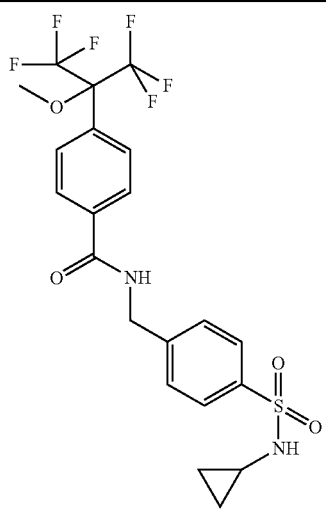 | N-[[4-(cyclopropylsulfamoyl)phenyl]methyl]-4-[2,2,2-trifluoro-1-methoxy-1-(trifluoromethyl)ethyl]benzamide |
| 31 | 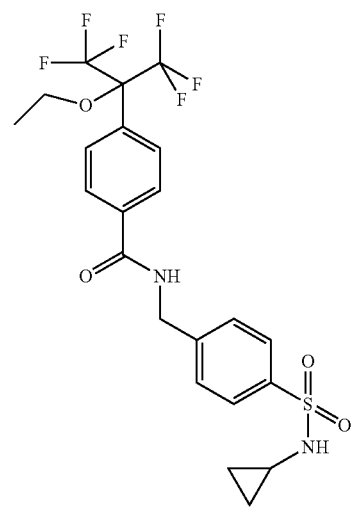 [SMILES: CCOC(c1ccc(C(=O)NCc2ccc(S(=O)(=O)NC3CC3)cc2)cc1)(C(F)(F)F)C(F)(F)F] | N-[[4-(cyclopropylsulfamoyl)phenyl]methyl]-4-[1-ethoxy-2,2,2-trifluoro-1-(trifluoromethyl)ethyl]benzamide |
| 32 | 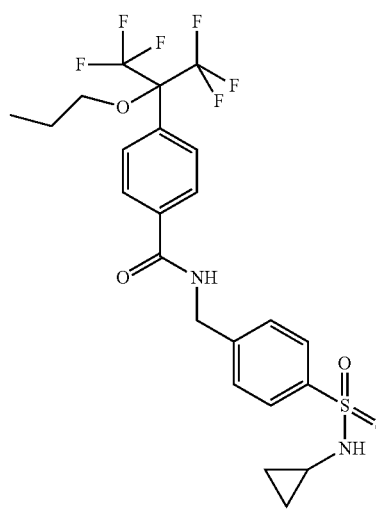 | N-[[4-(cyclopropylsulfamoyl)phenyl]methyl]-4-[2,2,2-trifluoro-1-propoxy-1-(trifluoromethyl)ethyl]benzamide |

| N° | Structure | IUPAC name |
| --- | --- | --- |
| 33 | 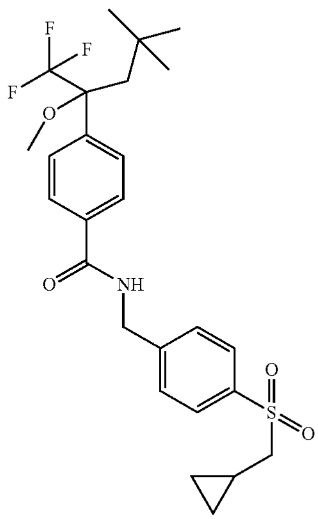 [SMILES: COC(CC(C)(C)C)(c1ccc(C(=O)NCc2ccc(S(=O)(=O)CC3CC3)cc2)cc1)C(F)(F)F] | N-[[4-(cyclopropylmethylsulfonyl)phenyl]methyl]-4-[1-methoxy-3,3-dimethyl-1-(trifluoromethyl)butyl]benzamide |
| 34 | 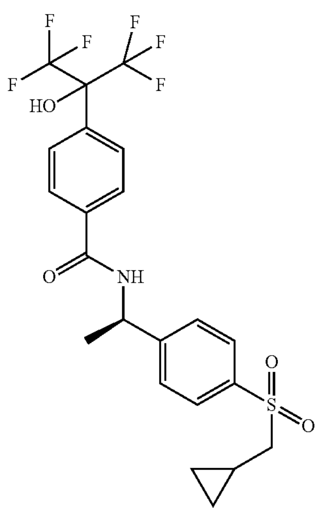 [SMILES: C[C@@H](NC(=O)c1ccc(C(O)(C(F)(F)F)C(F)(F)F)cc1)c1ccc(S(=O)(=O)CC2CC2)cc1] | N-[(1R)-1-[4-(cyclopropylmethylsulfonyl)phenyl]ethyl]-4-[2,2,2-trifluoro-1-hydroxy-1-(trifluoromethyl)ethyl]benzamide |
| 35 | 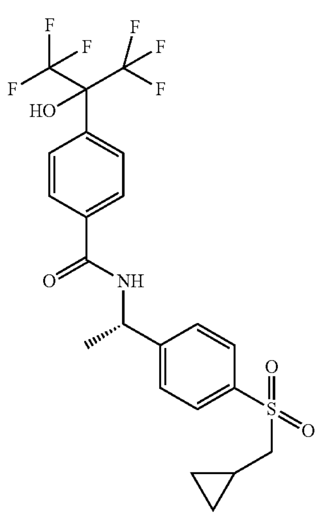 [SMILES: C[C@H](NC(=O)c1ccc(C(O)(C(F)(F)F)C(F)(F)F)cc1)c1ccc(S(=O)(=O)CC2CC2)cc1] | N-[(1S)-1-[4-(cyclopropylmethylsulfonyl)phenyl]ethyl]-4-[2,2,2-trifluoro-1-hydroxy-1-(trifluoromethyl)ethyl]benzamide |

-continued

| N° | Structure | IUPAC name |
|---|---|---|
| 36 | 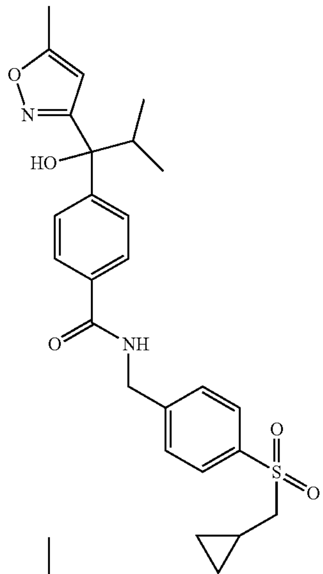 [SMILES: Cc1cc(C(O)(c2ccc(C(=O)NCc3ccc(S(=O)(=O)CC4CC4)cc3)cc2)C(C)C)no1] | N-[[4-(cyclopropylmethylsulfonyl)phenyl]methyl]-4-[1-hydroxy-2-methyl-1-(5-methylisoxazol-3-yl)propyl]benzamide |
| 37 | 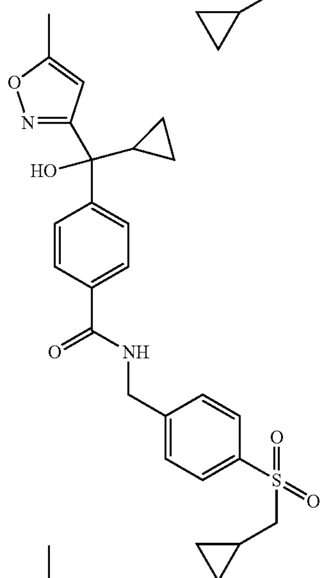 | 4-[cyclopropyl-hydroxy-(5-methylisoxazol-3-yl)methyl]-N-[[4-(cyclopropylmethylsulfonyl)phenyl]methyl]benzamide |
| 38 | 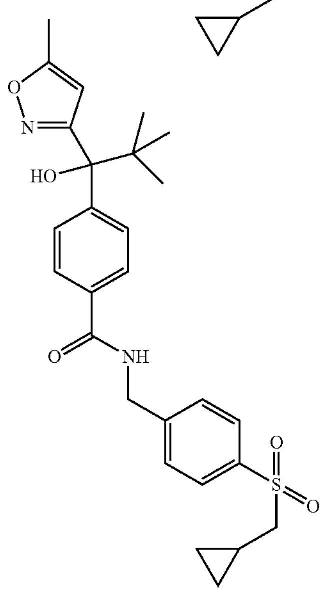 | N-[[4-(cyclopropylmethylsulfonyl)phenyl)methyl]-4-[1-hydroxy-2,2-dimethyl-1-(5-methylisoxazol-3-yl)propyl]benzamide |

The compounds of Formula I can form salts, which are also within the scope of this invention. Reference to a compound of Formula I herein is understood to include reference to salts thereof, unless otherwise indicated.

The compounds of Formula I may contain asymmetric or chiral centers and, therefore, exist in different stereoisomeric forms. It is intended that all stereoisomeric forms of the compounds of Formula I as well as mixtures thereof, including racemic mixtures, form part of the present invention.

Diastereomeric mixtures can be separated into their individual diastereomers on the basis of their physical chemical differences by methods well known to those skilled in the art, such as, for example, chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g. hydrolyzing) the individual diastereomers to the corresponding pure enantiomers. Enantiomers can also be separated by use of chiral HPLC column.

The skilled artisan will recognize that desirable IC50 values are dependent on the compound tested. For example, a compound with an IC50 value less than $10^{-5}$ M is generally considered a candidate for drug selection. Preferably, this value is lower than $10^{-6}$ M. However, a compound which has a higher IC50 value, but is selective for the particular receptor, may be even a better candidate.

The compounds of the invention inhibit RORγ activity. Modulation of RORγ activity can be measured using for example biophysical (natural) ligand displacement studies, biochemical AlphaScreen or FRET assays, cellular GAL4 reporter gene assays, cellular IL-17 promotor reporter assay or functional IL-17 ELISA assays using for example mouse splenocytes or human peripheral blood mononuclear cells (PBMCs) cultured under $T_H17$ polarizing conditions.

In such assays, the interaction of a ligand with RORγ can be determined by measuring, for example, the ligand modulated interaction of cofactor-derived peptides with the RORγ ligand binding domain, or measuring the gene products of ligand modulated RORγ mediated transcription using, for example, luciferase reporter assays or IL-17 ELISA assays.

The present invention also relates to a pharmaceutical composition comprising compounds or pharmaceutically acceptable salts thereof having the general Formula I in admixture with pharmaceutically acceptable excipients and optionally other therapeutic agents. The present invention also relates to a pharmaceutical composition comprising at least one therapeutically active agent. The excipients must be "acceptable" in the sense of being compatible with the other ingredients of the composition and not deleterious to the recipients thereof.

The invention further includes a compound of Formula I in combination with one or more other drug(s).

Compositions include e.g. those suitable for oral, sublingual, subcutaneous, intravenous, intramuscular, topical, nasal, local or rectal administration, and the like, all in unit dosage forms for administration.

For oral administration, the active ingredient may be presented as discrete units, such as tablets, capsules, powders, granulates, solutions, suspensions, and the like.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable excipients, the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described.

The exact dose and regimen of administration of the active ingredient, or a pharmaceutical composition thereof, may vary with the particular compound, the route of administration, and the age and condition of the individual subject to whom the medicament is to be administered.

In general parenteral administration requires lower dosages than other methods of administration which are more dependent upon absorption. However, a dosage for humans preferably contains 0.0001-100 mg per kg body weight. The desired dose may be presented as one dose or as multiple sub-doses administered at appropriate intervals throughout the day.

The compounds according to the invention can be used in therapy.

A further aspect of the invention resides in the use of compounds according to the invention or a pharmaceutically acceptable salt thereof for the treatment of RORγ-mediated diseases or RORγ mediated conditions.

The compounds according to the invention can be used in as medicament.

Another aspect of the invention resides in the use of compounds having the general Formula I or a pharmaceutically acceptable salt thereof for the treatment of autoimmune diseases, in particular those diseases in which Th17 cells and non-Th17 cells, which express Th17 hallmark cytokines play a prominent role. These include, but are not limited to, the treatment of rheumatoid arthritis, psoriasis, inflammatory bowel disease, Crohn's disease and multiple sclerosis.

In another aspect, compounds having the general Formula I or a pharmaceutically acceptable salt thereof can be used for treatment of inflammatory diseases in which Th17 cells and/or non-Th17 cells, which express Th17 hallmark cytokines play a prominent role such as, but not limited to respiratory diseases, osteoarthritis and asthma. Also, compounds or a pharmaceutically acceptable salt thereof having the general Formula I can be used for treatment of infectious diseases in which Th17 cells and/or non-Th17 cells, which express Th17 hallmark cytokines play a prominent role such as, but not limited to mucosal leishmaniasis.

Compounds having the general Formula I or a pharmaceutically acceptable salt thereof can also be used for treatment of other diseases in which Th17 cells and/or non-Th17 cells, which express Th17 hallmark cytokines play a prominent role such as, but not limited to Kawaski disease and Hashimoto's thyroiditis.

In yet another aspect the invention resides in the use of compounds having the general Formula I for the treatment of multiple sclerosis, inflammatory bowel disease, Crohn's disease, psoriasis, rheumatoid arthritis, asthma, osteoarthritis, Kawaski disease, Hashimoto's thyroiditis, cancer and mucosal leishmaniasis.

In another aspect, the compounds according to the invention can be used in therapies to treat or prevent multiple sclerosis, inflammatory bowel disease, Crohn's disease, psoriasis and rheumatoid arthritis, asthma, osteoarthritis, Kawasaki disease, Hashimoto's thyroiditis, cancer and mucosal leishmaniasis.

In another aspect the compounds according to the invention can be used to treat or prevent psoriasis.

In yet another aspect the compounds according to the invention can be used to treat inflammatory bowel disease.

The invention is illustrated by the following examples.

EXEMPLIFICATION

As depicted in the Examples below, in certain exemplary embodiments, compounds are prepared according to the following general procedures. It will be appreciated that, although the general methods depict the synthesis of certain compounds of the invention, the following general methods, and other methods known to one skilled in the art, can be applied to all compounds and subclasses and species of each of these compounds, as described herein.

General Methods of Preparation.

The compounds described herein, including compounds of general Formula I, building blocks II, III, IV and V can be readily prepared according to the following reaction schemes and examples, or modifications thereof, using readily available starting materials, reagents and conventional synthesis procedures. Many of the reactions can also be carried out under microwave conditions or using conventional heating or utilizing other technologies such as solid phase reagents/scavengers or flow chemistry. For example, hydrogenation reactions can be performed using a continuous flow chemistry apparatus such as the H-Cube Pro® from ThalesNano Nanotechnology company in Budapest, Hungary. In these reactions, it is also possible to make use of variants which are themselves known to those skilled in the art, but are not mentioned in greater detail. For example, where specific acids, bases, reagents, coupling agents, solvents, etc. are mentioned, it is understood that other suitable acids, bases, reagents, coupling agents, solvents etc. may be used and are included within the scope of the present invention. Furthermore, other methods for preparing compounds of the invention will be readily apparent to a person of ordinary skill in the art in light of the following reaction schemes and examples. In cases where synthetic intermediates and final products contain potentially reactive functional groups, for example amino, hydroxyl, thiol and carboxylic acid groups that may interfere with the desired reaction, it may be advantageous to employ protected forms of the intermediate. Methods for the selection, introduction and subsequent removal of protecting groups are well known to those skilled in the art. The compounds obtained by using the general reaction sequences may be of insufficient purity. The compounds can be purified by using any of the methods of purification of organic compounds, for example, crystallization or silica gel or alumina column chromatography, using different solvents in suitable ratios. All possible stereoisomers are envisioned within the scope of the invention. In the discussion below variables have the meaning indicated above unless otherwise indicated.

The abbreviations used in these experimental details are listed below and additional ones should be considered known to a person skilled in the art of synthetic chemistry.

Abbreviations used herein are as follow: HATU: 2-(7-Aza-1H-benzotriazole-1-yl)-1,1,3,3-tetramethyluronium hexafluorophosphate; DMF: Dimethylformamide; DiPEA: Diisopropylethylamine; DMAP: 4-(dimethylamino)pyridine; $CH_2Cl_2$, DCM: dichloromethane; DCC: N,N'-Dicyclohexylcarbodiimide; mCPBA: 3-chloroperoxybenzoic acid; TFA: Trifluoroacetic acid; TFAA: Trifluoroacetic anhydride; THF: Tetrahydrofuran; cont.: continuous; DMSO: Dimethylsulfoxide; PTSA: p-Toluenesulfonic acid; PyBOP: (Benzotriazol-1-yloxy)tripyrrolidinophosphonium hexafluorophosphate; EtOH: Ethanol; DIAD: Diisopropyl azodicarboxylate; TLC: Thin Layer Chromatography; $Pd(dba)_2$: Bis(dibenzylideneacetone)palladium(0); $PPh_3$: Triphenyl phosphine; NMP: N-Methyl-2-pyrrolidinone; EDCI: 1-Ethyl-3-(3-dimethylaminopropyl)carbodiimide hydrochloride; BuLi: n-Butyl lithium; TBAF: Tetra-N-butylammonium fluoride; TMS: Trimethylsilyl; EtOAc: ethyl acetate; ACN, $CH_3CN$: acetonitrile; RT: room temperature; MeOH: methanol; $Et_3N$, TEA: triethylamine, $K_2CO_3$: potassium carbonate, $MgSO_4$: magnesium sulfate; NaOH: sodium hydroxide, $NaHCO_3$: sodium bicarbonate; $Na_2SO_3$: sodium sulfite; $TMSCF_3$: Trifluoromethyltrimethylsilane; $H_2O$: water; HCl: hydrochloric acid; LiOH: lithium hydroxide; HBTU: N,N,N',N'-Tetramethyl-O-(1H-benzotriazol-1-yl) uronium hexafluorophosphateChemical names are preferred IUPAC names, generated using Accelrys Draw 4.1.

If a chemical compound is referred to using both a chemical structure and a chemical name, and an ambiguity exists between the structure and the name, the structure predominates.

General Procedures

Scheme 1:

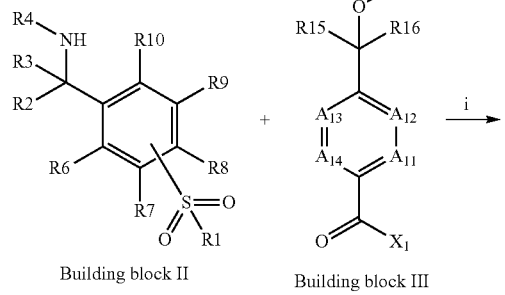

Building block II        Building block III

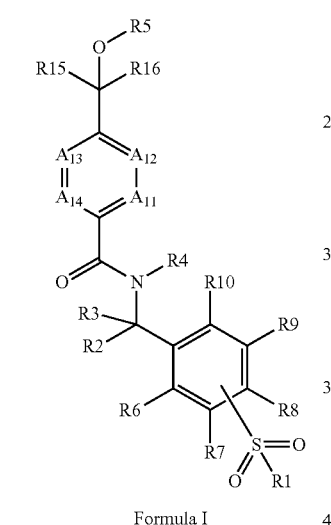

Formula I

Conditions: i) EDCl, DMAP, CH$_2$Cl$_2$.

Scheme 2:

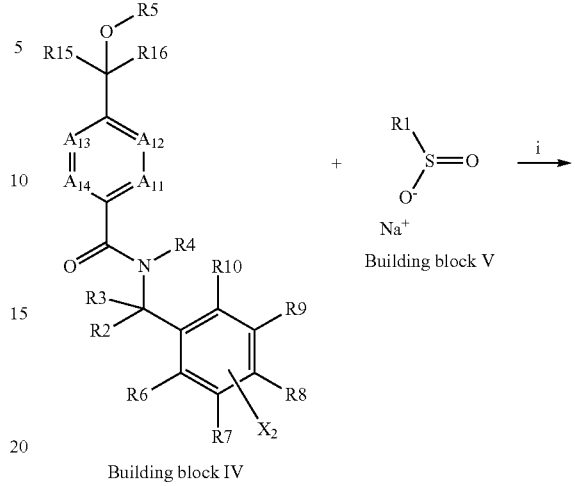

Building block IV                    Building block V

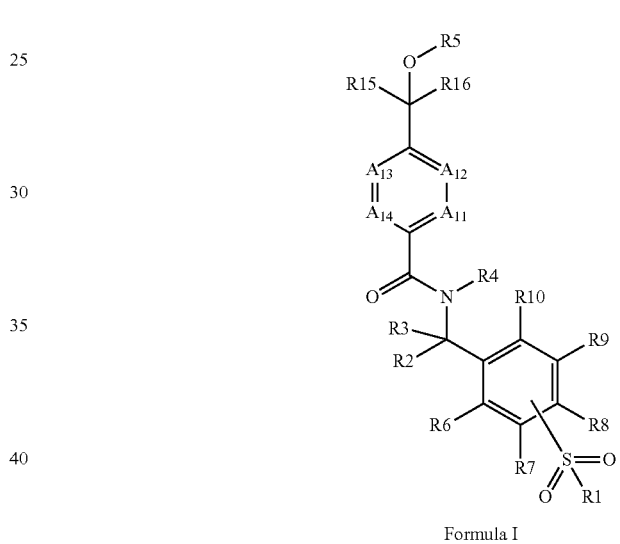

Formula I

Conditions: i) CuOSO$_2$CF$_3$, 1,2-diaminocyclohexane, DMSO, 125° C.

As depicted in scheme 1, the derivatives of the invention having Formula I can be prepared by methods known in the art of organic chemistry. Compounds of the invention can for example be obtained by an amide coupling reaction between an amine derivative of building block II, wherein $R_1$, $R_2$, $R_3$, $R_4$, $R_6$, $R_7$, $R_8$, $R_9$ and $R_{10}$ are as defined for compound Formula I and a carboxylic acid derivative of building block III ($X_1$ is OH), wherein $R_5$, $R_{15}$, $R_{16}$, $A_{11}$, $A_{12}$, $A_{13}$ and $A_{14}$ are as defined for compound of Formula I, using a coupling reagent such as EDCI, HATU, DCC, or PyBOP or the like, in the presence of a suitable base such as DiPEA or DMAP.

Alternatively, the carboxylic acid derivative of building block III ($X_1$=OH) can be converted into an acyl chloride derivative of building block III ($X_1$=Cl), using for example SOCl$_2$ or oxalyl chloride. The obtained acyl chloride derivative of building block III ($X_1$=Cl), wherein $R_5$, $R_{15}$, $R_{16}$, $A_{11}$, $A_{12}$, $A_{13}$ and $A_{14}$ are as defined for compounds of Formula I, can be coupled with an amine derivative of building block II, wherein $R_1$, $R_2$, $R_3$, $R_4$, $R_6$, $R_7$, $R_8$, $R_9$ and $R_{10}$ have the meaning as previously described in the presence of a suitable base such as Et$_3$N or the like.

Scheme 2 demonstrates an alternative route for the preparation of derivatives of Formula I wherein $R_1$, $R_2$, $R_3$, $R_4$, $R_5$, $R_6$, $R_7$, $R_8$, $R_9$, $R_{10}$, $R_{15}$, $R_{16}$, $A_{11}$, $A_{12}$, $A_{13}$ and $A_{14}$ are as defined for compounds of Formula I.

Compounds of the invention can be obtained for example by a coupling of an aryl bromide ($X_2$=Br) or iodide ($X_2$=I) derivative of building block IV and a sulfinic acid salt derivative of building block V such as a sodium sulfinate, using a copper(I) catalyst such as copper(I) trifluoromethanesulfonate benzene complex, copper(I) iodide or the like, in the presence of a suitable ligand such as trans-1,2-diaminocyclohexane, phenanthroline, dimethylimidazolidinone, or the like. The reaction is performed by heating the mixture in a polar solvent such as DMSO, DMF or the like at temperature between 80 and 140° C. using microwave or conventional heating conditions.

Scheme 3:

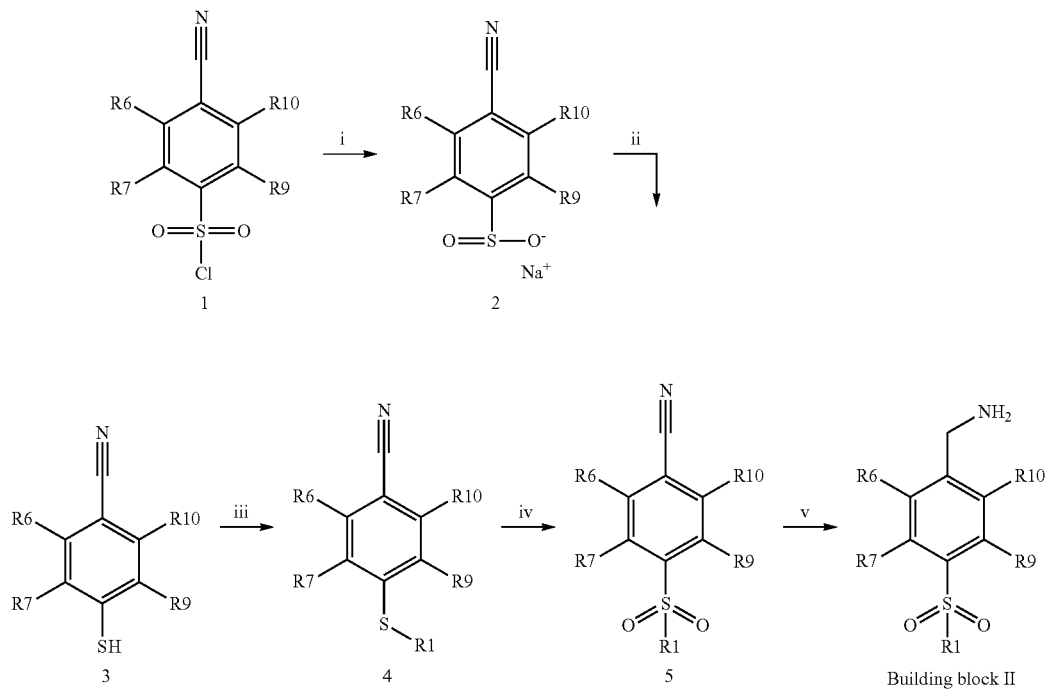

Conditions: i) Na₂SO₃, NaHCO₃, water, 70° C.; ii) alkylhalide, anhydrous DMSO, 100° C.; iii) K₂CO₃, alkylhalide, CH₃CN, RT; iv) mCPBA, DCM, 0° C. → RT; v) H₂, Raney Ni, NH₃/MeOH, 70° C.

Scheme 3 illustrates general methods for the preparation of building blocks II wherein $R_1$, $R_6$, $R_7$, $R_9$ and $R_{10}$ are as defined for compounds of Formula I.

4-Cyanobenzenesulfonyl chloride derivatives 1 on reaction with sodium sulfite in the presence of a suitable base such as sodium bicarbonate give the corresponding sulfinate derivatives 2, which can be alkylated with an appropriate alkylhalide to give alkylsulfonylbenzonitrile derivatives 5.

Alternatively, 4-mercapto-2-methylbenzonitrile derivatives 3 can be alkylated in the presence of a suitable base such as potassium carbonate to give the corresponding thioether derivatives 4. Oxidation, using e. g. mCPBA, gives alkylsulfonylbenzonitrile derivatives 5, which after hydrogenation of the nitrile moiety using a suitable catalyst such as Raney nickel gives benzylamines of Formula II.

Scheme 4:

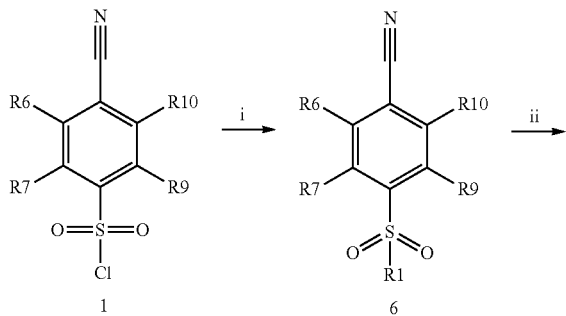

-continued

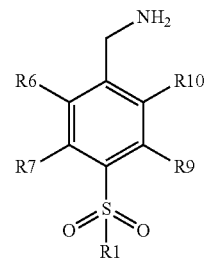

Building block II

Conditions: i) a suitable primary or secondary amine, Et₃N, DCM, RT; ii) H₂, Raney Ni, NH₃/MeOH, cont. flow, 70° C.

Scheme 4 illustrates a general reaction scheme for the preparation of building blocks II wherein $R_1$ is (di)C(3-6)cycloalkylamino or (di)(C(3-6)cycloalkylC(1-3)alkyl)amino as previously described and $R_6$, $R_7$, $R_9$ and $R_{10}$ are as defined for compounds of Formula I.

4-Cyanobenzenesulfonyl chloride derivatives 1 on reaction with primary or secondary amines in the presence of a suitable base such as TEA give the corresponding sulfonamide derivatives 6, which can be hydrogenated using a suitable catalyst such as Raney nickel to obtain benzylamines of Formula II wherein $R_1$ is (di)C(3-6)cycloalkylamino or (di)(C(3-6)cycloalkylC(1-3)alkyl)amino as previously described.

Some of the building blocks II used in the examples of general Formula I are commercially available, known or prepared according to methods known to those skilled in the art.

Scheme 5:

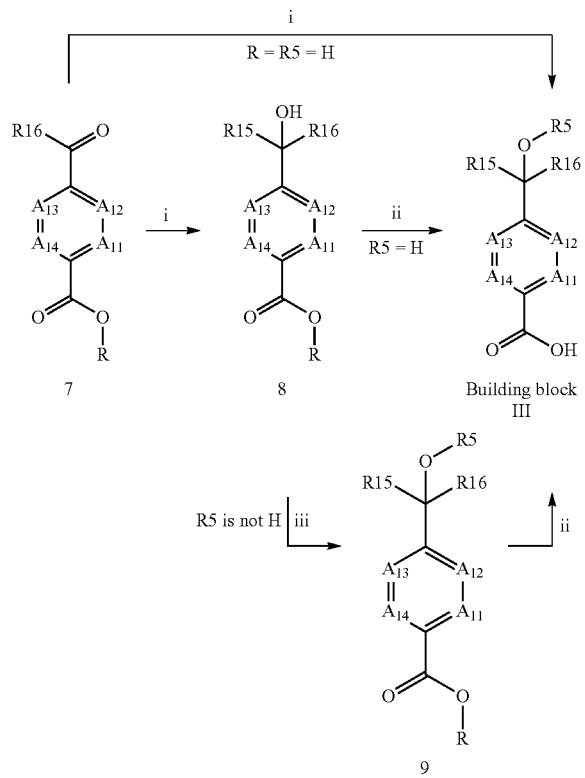

Conditions: ($R_{15}$ = $CF_3$) i) $TMSCF_3$, TBAF, THF; ii) NaOH, THF, EtOH; iii) suitable alkyl halide, base, solvent.

Scheme 6

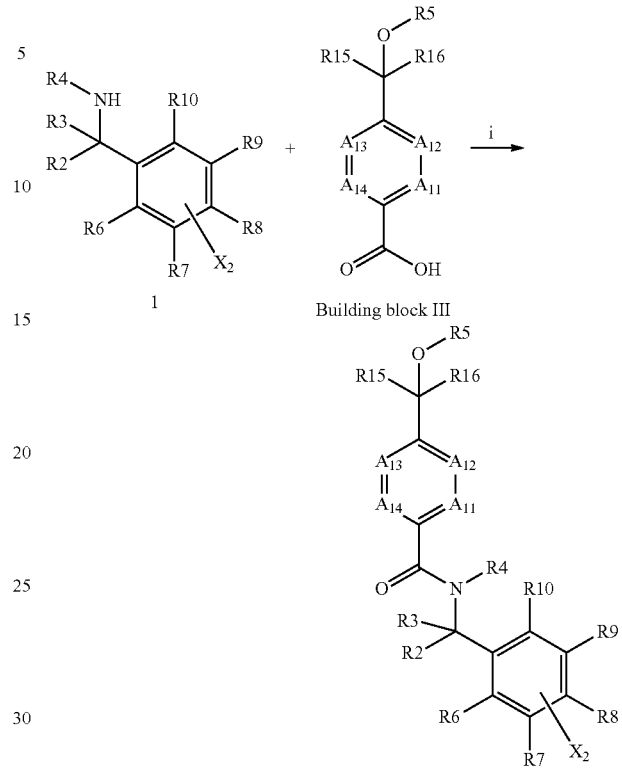

Conditions: i) EDCl, DMAP, $CH_2Cl_2$.

Scheme 5 illustrates a general reaction scheme for the preparation of building blocks III wherein $R_{15}$ is $CF_3$ and $R_5$, $R_{16}$, $A_{11}$, $A_{12}$, $A_{13}$ and $A_{14}$ are as defined for compounds of Formula I.

Ketone derivatives 7 wherein R is H or lower alkyl such as methyl or ethyl can be treated with $TMSCF_3$ and TBAF to give the corresponding alcohol derivatives 8, which can be hydrolyzed by a hydroxide source such as NaOH to obtain building blocks III wherein $R_{15}$ is $CF_3$, $R_5$ is H and $R_{16}$, $A_{11}$, $A_{12}$, $A_{13}$ and $A_{14}$ are as previously described. In the case where R is H, the hydrolysis step is not needed since the alcohol derivatives 8 wherein R is H correspond to building blocks III wherein $R_{15}$ is $CF_3$ and $R_5$ is H.

Alcohol derivatives 8 can be alkylated with a suitable alkyl halide in presence of a base such as potassium carbonate, sodium hydride or the like to give ether derivatives 9 which can then be hydrolyzed to building blocks III wherein $R_{15}$ is $CF_3$ and $R_5$, $R_{16}$, $A_{11}$, $A_{12}$, $A_{13}$ and $A_{14}$ with the proviso that $R_5$ is not H. In certain cases, when commercially available, alcohol derivatives 8 wherein R is H can be dialkylated with 2 equivalents of a suitable alkyl halide in presence of a base to give ether derivatives 9 wherein R=$R_5$ which can then be hydrolyzed to building blocks III wherein $R_{15}$ is $CF_3$ and $R_5$ is not H.

Some of the building blocks III used in the examples of general Formula I are commercially available, known or prepared according to methods known to those skilled in the art.

As depicted in scheme 6, the building blocks IV can be prepared by an amide coupling reaction between an amine derivative 10, wherein $R_2$, $R_3$, $R_4$, $R_6$, $R_7$, $R_8$, $R_9$, $R_{10}$ are as previously described and $X_2$ is Br or I and a carboxylic acid derivative of building block III, wherein $R_5$, $R_{15}$, $R_{16}$, $A_{11}$, $A_{12}$, $A_{13}$ and $A_{14}$ are as defined for compounds of Formula I, using a coupling reagent such as EDCl, HATU, DCC, or PyBOP or the like, in the presence of a suitable base such as DiPEA or DMAP.

Scheme 7:

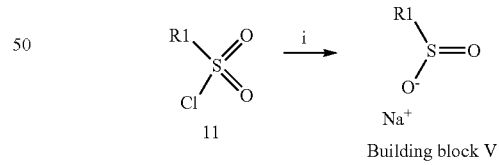

Conditions: i) $Na_2SO_3$, $NaHCO_3$, $H_2O$, 50° C.

Scheme 7 shows a general reaction scheme for the preparation of building blocks V wherein $R_1$ has the meaning as previously described.

Sulfonyl chlorides 11 can be converted to sodium sulfinate derivatives of building block V by treatment with sodium sulfite in water in the presence of a suitable base such as sodium bicarbonate.

Some of the building blocks V are commercially available, known or prepared according to methods known to those skilled in the art.

Scheme 8:

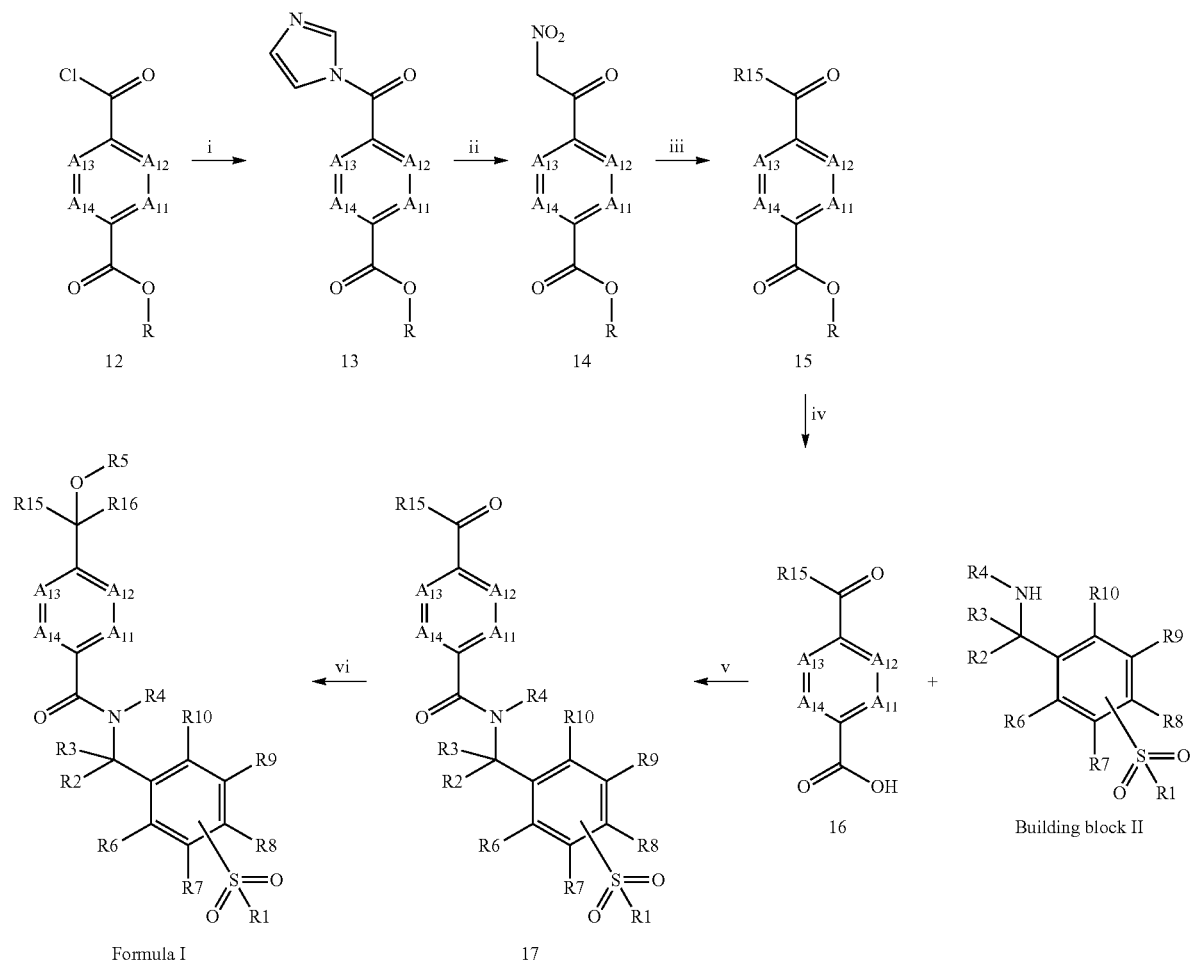

Formula I            17

Conditions: i) 1H-imidazole, CH₃CN, RT; ii) tBuOK, THF, nitromethane, reflux iii) PTSA, isopropenyl acetate, reflux iv) LiOH, H₂O, THF, RT; v) HBTU, TEA, DMF, RT; vi) R₁₆MgX, THF, 0° C. then RT.

Scheme 8 illustrates a method for the preparation of derivatives of Formula I, wherein $R_5$ is H, $R_{15}$ is 5-methyl-isoxazol-3-yl, $R_{16}$ is C(1-6)alkyl or C(3-6)cycloalkyl as previously described and $R_1$, $R_2$, $R_3$, $R_4$, $R_6$, $R_7$, $R_8$, $R_9$, $R_{10}$, $A_{11}$, $A_{12}$, $A_{13}$ and $A_{14}$ are as defined for compounds of Formula I.

The acid chloride derivatives 12, wherein R is lower alkyl such as methyl or ethyl on reaction with 1H-imidazole give the corresponding N-acyl imidazole derivatives 13, which can be converted to the α-nitroketone derivatives 14 by using nitromethane in the presence of a suitable base such as tBuOK. Reaction of derivatives 14 with isopropenyl acetate under acid-catalyzed conditions produced the derivatives 15, which can be hydrolyzed by a hydroxide source such as LiOH to obtain derivatives 16. Derivatives 17, can be prepared by an amide coupling reaction between an amine derivative of building block II, and a carboxylic acid derivative 16, using a coupling reagent such as HBTU, in the presence of a suitable base such as TEA or the like. Reaction of derivatives 17 with an appropriate alkyl magnesium halide ($R_{16}$MgX), wherein $R_{16}$ is C(1-6)alkyl or C(3-6) cycloalkyl and X is Cl or Br, gives derivatives of Formula I, wherein $R_5$ is H, $R_{15}$ is 5-methyl-isoxazole-3-yl, $R_{16}$ is C(1-6)alkyl or C(3-6)cycloalkyl as previously described and $R_1$, $R_2$, $R_3$, $R_4$, $R_6$, $R_7$, $R_8$, $R_9$, $R_{10}$, $A_{11}$, $A_{12}$, $A_{13}$ and $A_{14}$ are as defined for compounds of Formula I.

Intermediates

Building Blocks II-1-II-3

II-1: [4-(cyclopropylmethylsulfonyl)phenyl]methanamine

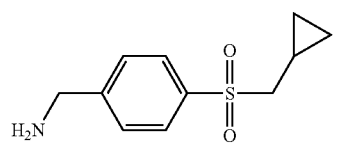 [SMILES: NCc1ccc(S(=O)(=O)CC2CC2)cc1]

i) To a solution of 4-cyanobenzenesulfonyl chloride (75 g) in water (281 mL) was added portionwise NaHCO₃ (62.5 g) followed by sodium sulfite (93.8 g). The reaction mixture was stirred for 3 hours at 70° C., then cooled to RT and concentrated under reduced pressure. MeOH (500 mL) was added and the mixture was concentrated to a small volume, then filtered. The solid was taken into MeOH (500 mL), mechanically stirred then filtered. The combined filtrates were taken into EtOAc and concentrated under high vacuum to obtain 71 g of sodium 4-cyanobenzenesulfinate. MS(ES⁻) m/z 166 [M−H]⁻.

ii) A solution of the compound obtained in the preceding step (5 g) in anhydrous dimethyl sulfoxide (50 mL) and bromomethylcyclopropane (2.6 mL) was stirred for 1 hour and 45 minutes at 100° C. in an autoclave. Bromomethylcyclopropane (2.6 mL) was then added and the mixture was stirred another hour at 100° C. After being cooled to RT, the reaction mixture was poured into water (150 mL) and extracted with EtOAc (3×50 mL). The combined extracts were washed with brine (4×100 mL), dried over MgSO₄ and concentrated under reduced pressure to obtain 3.8 g of 4-(cyclopropylmethylsulfonyl)benzonitrile. MS(ES⁺) m/z 222 [M+H]⁺.

iii) A solution of the compound obtained in the preceding step (1.7 g) in 2N ammonia in MeOH (250 mL) was passed through the continuous flow hydrogenation apparatus H-Cube Pro® equipped with a fresh Raney Nickel cartridge (70×4 mm i.d.) using the to settings: flow rate 1 mL/min, H₂ pressure 50 bars and cartridge temperature (70° C.). The reaction mixture was then evaporated and purified by column chromatography on silica gel, using 0% to 18% MeOH in EtOAc as the eluent to obtain 1.6 g of expected product. MS(ES⁺) m/z 226.0 [M+H]⁺.

II-2: [4-(cyclopropylmethylsulfonyl)-2-methyl-phenyl]methanamine

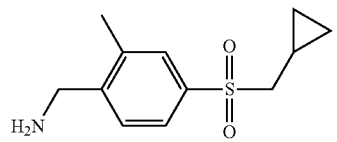 [SMILES: Cc1cc(S(=O)(=O)CC2CC2)ccc1CN]

i. To a solution of 2-methyl-4-sulfanyl-benzonitrile (3.0 g) in ACN (55 mL) under argon were added K₂CO₃ (7.0 g) followed by bromomethylcyclopropane (2.3 mL). The reaction mixture was stirred at RT overnight, filtered and then concentrated under reduced pressure to obtain 4.06 g of 4-(cyclopropylmethylsulfanyl)-2-methyl-benzonitrile. MS(ES⁺) m/z 204 [M+H]⁺.

ii) To a solution of the compound obtained in the preceding step (4.06 g) in DCM (180 mL) precooled to 0° C. was added portionwise mCPBA (13.4 g). The reaction mixture was then stirred at RT for one hour, washed with an aqueous solution saturated with NaHCO₃, then with water and finally with brine. The extract was dried over MgSO₄, filtered and concentrated under reduced pressure. The residue was purified by column chromatography on silica gel, using 0% to 20% EtOAc in heptane as the eluent to obtain 3.93 g of 4-(cyclopropylmethylsulfonyl)-2-methyl-benzonitrile. MS(ES⁺) m/z 236 [M+H]⁺.

iii) A solution of 1.0 g of the compound obtained in the preceding step in 2N ammonia in MeOH (80 mL) and Raney Nickel (24.9 mg) was stirred under a stream of H₂ (50 bars) in an autoclave during 4 hours at 70° C. After being cooled to RT, the reaction mixture was filtered over celite and concentrated under reduced pressure to obtain 1.03 g of the expected product. MS(ES⁺) m/z 240.1 [M+H]⁺.

II-3: 4-(aminomethyl)-N-cyclopropyl-benzenesulfonamide

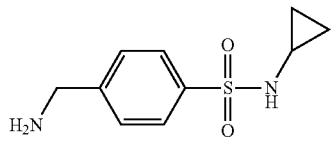

i) Cyclopropanamine (0.4 mL) and then TEA (1.5 mL) were added to a solution of 4-cyanobenzenesulfonyl chloride (1.0 g) in DCM (10 mL). The reaction was exothermic, and temperature was kept below 35° C. After stirring overnight at RT, the reaction mixture was poured into water (15 mL) and extracted with DCM (2×20 mL). The combined organic layers were washed with brine (10 mL), dried over MgSO₄, filtered and concentrated under reduced pressure. The crude product was purified by column chromatography on silica gel, using DCM as the eluent to obtain 449 mg of 4-cyano-N-cyclopropyl-benzenesulfonamide. MS(ES⁻) m/z 221 [M−H]⁻.

ii) A solution of the compound obtained in the preceding step (449 mg) in 2N ammonia in MeOH (250 mL) was passed through the continuous flow hydrogenation apparatus H-Cube Pro® equipped with a fresh Raney Nickel cartridge (70×4 mm i.d.) using the settings: flow rate 1 mL/min, H₂ pressure 50 bars and cartridge temperature (70° C.). The reaction mixture was then evaporated and purified by column chromatography on silica gel, using 0% to 18% MeOH in EtOAc as the eluent to obtain 367 mg of expected product. MS(ES⁺) m/z 226.0 [M+H]⁺.

Building Blocks III-1-III-14

III-1: 4-(2,2,2-trifluoro-1-hydroxy-1-methyl-ethyl)benzoic Acid

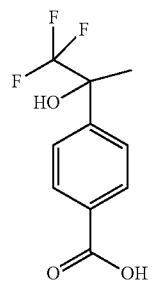

i) To a solution of methyl 4-acetylbenzoate (1 g) in anhydrous THF (10 mL) was added TMSCF₃ (2.5 mL) followed by dropwise addition of a 1M solution of TBAF in THF (15.7 mL). The reaction mixture was stirred for 18 hours at RT then taken into ether (50 mL), washed with water (50 mL) and brine (50 mL), dried over MgSO₄ and concentrated under reduced pressure. The crude product was purified by column chromatography on silica gel, using 0% to 30% EtOAc in cyclohexane as the eluent to obtain 750 mg of methyl 4-(2,2,2-trifluoro-1-hydroxy-1-methyl-ethyl)benzoate. MS(ES⁺) m/z 249.0 [M+H]⁺.

ii) To a solution of the compound obtained in the preceding step (600 mg) in THF (10 mL) was added a 1N aqueous solution of NaOH (3.6 mL). After stirring for 18 hours at RT, the reaction was not complete. Additional 1N aqueous solution of NaOH (1.2 mL) was added. The reaction mixture was stirred for an additional 5 hours at RT then taken into ether (40 mL) and water (20 mL). The aqueous layer was separated, acidified with a 1N aqueous solution of HCl (2 equivalents), extracted twice with ether (50 mL), dried over MgSO$_4$ and concentrated under reduced pressure to obtain 550 mg of the expected compound. MS(ES$^-$) m/z 233.0 [M–H]$^-$.

Following a procedure analogous to that described for compound III-1, the following compounds were prepared.

III-2: 4-[1-(difluoromethyl)-2,2,2-trifluoro-1-hydroxy-ethyl]benzoic Acid

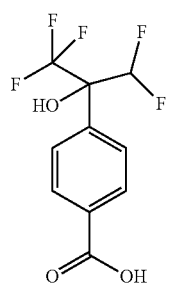 [SMILES: O=C(O)c1ccc(C(O)(C(F)F)C(F)(F)F)cc1]

MS(ES$^-$) m/z 269.0 [M–H]$^-$.

III-3: 4-[1-hydroxy-1-(trifluoromethyl)propyl]benzoic Acid

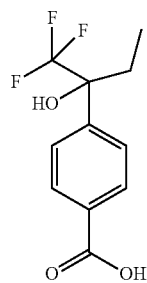

MS(ES$^-$) m/z 247.0 [M–H]$^-$.

III-4: 4-[1-hydroxy-1-(trifluoromethyl)butyl]benzoic Acid

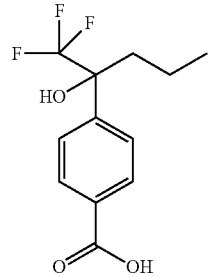 [SMILES: CCCC(O)(c1ccc(C(=O)O)cc1)C(F)(F)F]

MS(ES$^-$) m/z 261.0 [M–H]$^-$.

III-5: 4-[1-hydroxy-1-(trifluoromethyl)pentyl]benzoic Acid

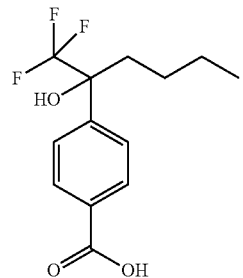 [SMILES: CCCCC(O)(c1ccc(C(=O)O)cc1)C(F)(F)F]

MS(ES$^-$) m/z 275.1 [M–H]$^-$.

III-6: 4-[1-hydroxy-3-methyl-1-(trifluoromethyl)butyl]benzoic Acid

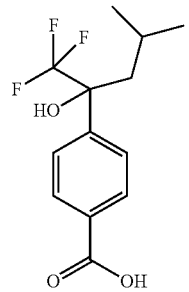 [SMILES: CC(C)CC(O)(c1ccc(C(=O)O)cc1)C(F)(F)F]

MS(ES$^-$) m/z 275.0 [M–H]$^-$.

III-7: 4-[1-hydroxy-3,3-dimethyl-1-(trifluoromethyl)butyl]benzoic Acid

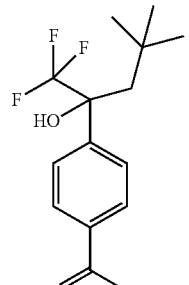

MS(ES$^-$) m/z 289.0 [M–H]$^-$.

III-8: 4-[1-hydroxy-2-methyl-1-(trifluoromethyl)propyl]benzoic Acid

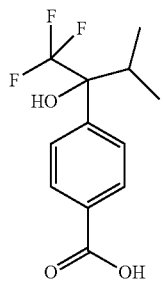

MS(ES⁻) m/z 261.0 [M−H]⁻.

III-9: 4-(1-cyclopropyl-2,2,2-trifluoro-1-hydroxy-ethyl)benzoic Acid

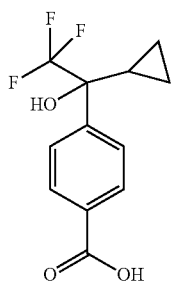 [SMILES: O=C(O)c1ccc(C(O)(C2CC2)C(F)(F)F)cc1]

MS(ES⁻) m/z 259.0 [M−H]⁻.

III-10: 4-(1-cyclopentyl-2,2,2-trifluoro-1-hydroxy-ethyl)benzoic Acid

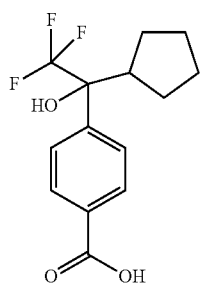 [SMILES: O=C(O)c1ccc(C(O)(C2CCCC2)C(F)(F)F)cc1]

MS(ES⁻) m/z 287.0 [M−H]⁻.

III-11: 4-(2,2,2-trifluoro-1-hydroxy-1-phenyl-ethyl)benzoic Acid

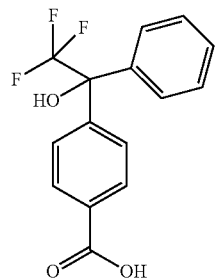 [SMILES: O=C(O)c1ccc(C(O)(c2ccccc2)C(F)(F)F)cc1]

MS(ES⁻) m/z 295.0 [M−H]⁻.

III-12: 4-(1-benzyl-2,2,2-trifluoro-1-hydroxy-ethyl)benzoic Acid

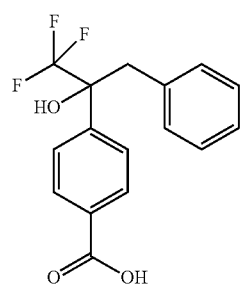 [SMILES: O=C(O)c1ccc(C(O)(Cc2ccccc2)C(F)(F)F)cc1]

MS(ES⁺) m/z 311.0 [M+H]⁺.

III-13: 3-methyl-4-[2,2,2-trifluoro-1-hydroxy-1-(trifluoromethyl)ethyl]benzoic Acid

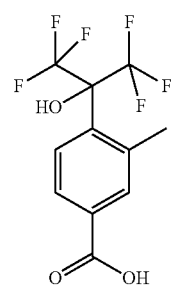 [SMILES: Cc1cc(C(=O)O)ccc1C(O)(C(F)(F)F)C(F)(F)F]

MS(ES⁻) m/z 301.1 [M−H]⁻.

III-14: 5-[2,2,2-trifluoro-1-hydroxy-1-(trifluoromethyl)ethyl]pyridine-2-carboxylic Acid

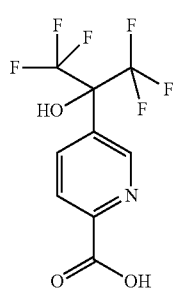

MS(ES⁻) m/z 287.9 [M−H]⁻.

Building Blocks III-15-III-21

III-15: 4-[1-ethoxy-2,2,2-trifluoro-1-(trifluoromethyl)ethyl]benzoic Acid

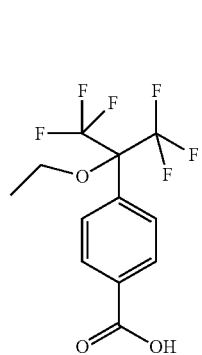 [SMILES: CCOC(c1ccc(C(=O)O)cc1)(C(F)(F)F)C(F)(F)F]

i) To a solution of 4-[2,2,2-trifluoro-1-hydroxy-1-(trifluoromethyl)ethyl]benzoic acid (500 mg) in acetone (10 mL) were added K$_2$CO$_3$ (959.27 mg) followed by iodoethane (1.08 g). The reaction mixture was stirred overnight at RT, then heated to 6000 for 5 hours, concentrated under reduced pressure and taken into DCM/water. The extract was separated and concentrated under reduced pressure to obtain 510 mg of ethyl 4-[1-ethoxy-2,2,2-trifluoro-1-(trifluoromethyl)ethyl]benzoate. MS(ES⁺) m/z 345 [M+H]⁺.

ii) To a solution of the compound obtained in the preceding step (510 mg) in THF (3 mL) and ethanol (3 mL) was added a 2M aqueous solution of NaOH (1.48 mL). The reaction mixture was stirred for 1 hour at RT then poured into a 2M aqueous solution of HCl (3.1 mL) and extracted with EtOAc. The extract was washed with brine and concentrated under reduced pressure to obtain 430 mg of the expected compound. MS(ES⁻) m/z 315.0 [M−H]⁻.

Following a procedure analogous to that described for compound III-15, the following compounds were prepared.

III-16: 4-[2,2,2-trifluoro-1-methoxy-1-(trifluoromethyl)ethyl]benzoic Acid

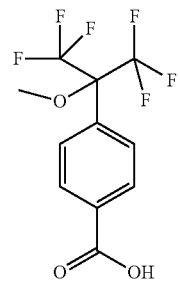

MS(ES⁻) m/z 300.9 [M−H]⁻.

III-17: 4-[2,2,2-trifluoro-1-propoxy-1-(trifluoromethyl)ethyl]benzoic Acid

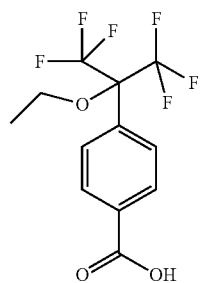

MS(ES⁻) m/z 329.0 [M−H]⁻.

III-18: 4-[1-butoxy-2,2,2-trifluoro-1-(trifluoromethyl)ethyl]benzoic Acid

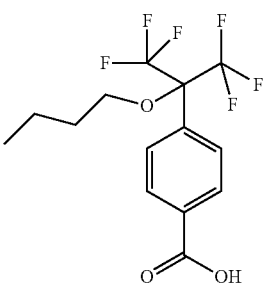 [SMILES: CCCCOC(c1ccc(C(=O)O)cc1)(C(F)(F)F)C(F)(F)F]

MS(ES) m/z 343.0 [M−H].

III-19: 4-[2,2,2-trifluoro-1-isopropoxy-1-(trifluoromethyl)ethyl]benzoic Acid

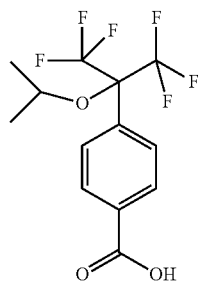 [SMILES: CC(C)OC(c1ccc(C(=O)O)cc1)(C(F)(F)F)C(F)(F)F]

MS(ES⁻) m/z 329.0 [M−H]⁻.

III-20: 4-[1-benzyloxy-2,2,2-trifluoro-1-(trifluoromethyl)ethyl]benzoic Acid

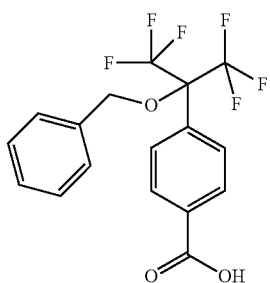 [SMILES: O=C(O)c1ccc(C(OCc2ccccc2)(C(F)(F)F)C(F)(F)F)cc1]

MS(ES⁻) m/z 377.0 [M−H]⁻.

III-21: 4-[1-methoxy-3,3-dimethyl-1-(trifluoromethyl)butyl]benzoic Acid

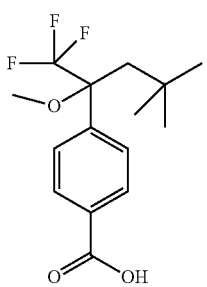 [SMILES: COC(CC(C)(C)C)(c1ccc(C(=O)O)cc1)C(F)(F)F]

MS(ES⁺) m/z 305.2 [M+H]⁺.

Building Blocks IV-1-IV-2

IV-1: N-[(1R)-1-(4-bromophenyl)ethyl]-4-[2,2,2-trifluoro-1-hydroxy-1-(trifluoromethyl)ethyl]benzamide

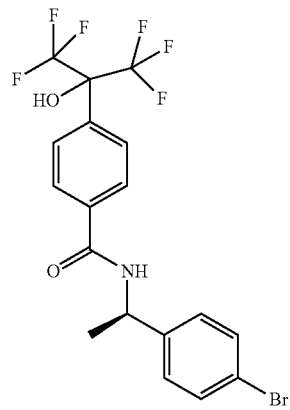 [SMILES: C[C@@H](NC(=O)c1ccc(C(O)(C(F)(F)F)C(F)(F)F)cc1)c1ccc(Br)cc1]

i) To a solution of (1R)-1-(4-bromophenyl)ethanamine (694 mg) in DCM (25 mL) was added 4-[2,2,2-trifluoro-1-hydroxy-1-(trifluoromethyl)ethyl]benzoic acid (1 g), EDCI (679 mg) and DMAP (85 mg). The reaction mixture was stirred at RT for 30 minutes. DCM and water were added. The mixture was filtered on water repellent filter cartridge and concentrated under reduced pressure. The residue was purified by column chromatography on silica gel, using 20% EtOAc in heptane as the eluent, to obtain 950 mg of the expected compound. MS(ES⁺) m/z 470 [M+H]⁺.

Following a procedure analogous to that described for compound IV-1, the following compound was prepared.

IV-2: N-[(1S)-1-(4-bromophenyl)ethyl]-4-[2,2,2-trifluoro-1-hydroxy-1-(trifluoromethyl)ethyl]benzamide

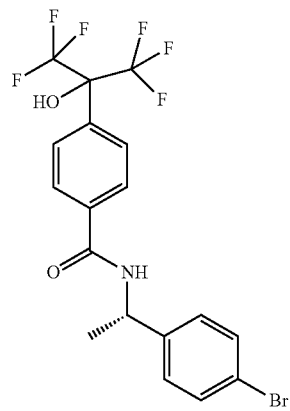 [SMILES: C[C@H](NC(=O)c1ccc(C(O)(C(F)(F)F)C(F)(F)F)cc1)c1ccc(Br)cc1]

MS(ES⁺) m/z 469.9 [M+H]⁺.

Building Blocks V-1

V-1: Sodium Cyclopropylmethanesulfinate

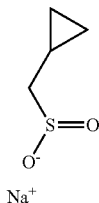

i) A solution of $Na_2SO_3$ (414 mg) in water (1.3 mL) was stirred for 10 minutes at RT. To the resulting mixture was added $NaHCO_3$ (547 mg). After stirring for 1 hour at 50° C., cyclopropylmethanesulfonyl chloride (430 mg) was added dropwise. The reaction mixture was stirred at 50° C. for 4 hours. Water was evaporated by flushing argon. The residue was dried under high vacuum. The residue was taken into MeOH (1.3 mL), filtered and concentrated under reduced pressure to obtain 380 mg of expected product. $MS(ES^+)$ m/z 120.9 $[M+H]^+$.

Examples 1-35

1: N-[[4-(cyclopropylmethylsulfonyl)phenyl]methyl]-4-[1-hydroxy-1-(trifluoromethyl)propyl]benzamide

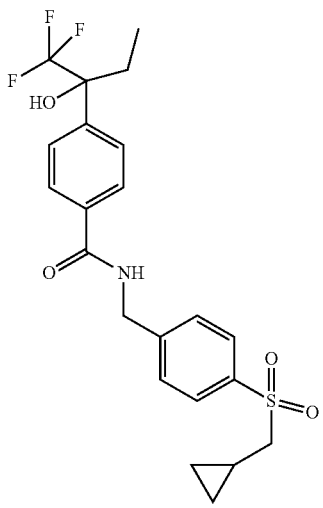 [SMILES: CCC(O)(c1ccc(C(=O)NCc2ccc(S(=O)(=O)CC3CC3)cc2)cc1)C(F)(F)F]

i) To a solution of an amine II-1 (100 mg) in DCM (3 ml) were sequentially added acid III-2 (121 mg), EDCI (107.5 mg) and DMAP (11 mg). The mixture was stirred at RT for 2 hours. EtOAc (50 mL) and water (50 mL) were added. The aqueous layer was separated and extracted twice with EtOAc. The combined extracts were washed with water, brine, dried over $MgSO_4$ and concentrated under reduced pressure. The residue was purified by column chromatography on silica gel, using 0% to 60% EtOAc in cyclohexane as the eluent, to obtain 130 mg of expected product. $MS(ES^+)$ m/z 456.0 $[M+H]^+$.

1H NMR (400 MHz, DMSO-d6) δ ppm 9.17 (t, J=6.02 Hz, 1H) 7.83-7.94 (m, 4H) 7.65 (d, J=8.28 Hz, 2H) 7.58 (d, J=8.28 Hz, 2H) 6.49 (br s, 1H) 4.59 (d, J=6.02 Hz, 2H) 3.20-3.28 (m, 2H) 2.23 (dq, J=14.21, 7.31 Hz, 1H) 1.97-2.07 (m, 1H) 0.77-0.87 (m, 1H) 0.67 (t, J=7.40 Hz, 3H) 0.41-0.47 (m, 2H) 0.09-0.14 (m, 2H)

The 2 enantiomers of example 1 were separated by chiral supercritical fluid chromatography using a column Chiralcel OJ 20 µm, 50×350 mm at 35° C. and a mobile phase, $CO_2$ 75% MeOH 25% TEA 0.1% followed by MeOH 35%, 300 ml/min, 100 bars with UV detection at 230 nm.

Starting from 115 mg of racemate, after concentration, 48 mg of (−)-N-[[4-(cyclopropylmethylsulfonyl)phenyl]methyl]-4-[1-hydroxy-1-(trifluoromethyl)propyl]benzamide (first isomer to be eluted) and 48 mg of (+)-N-[[4-(cyclopropylmethylsulfonyl)phenyl]methyl]-4-[1-hydroxy-1-(trifluoromethyl)propyl]benzamide were obtained.

(−)-1: (−)-N-[[4-(cyclopropylmethylsulfonyl)phenyl]methyl]-4-[1-hydroxy-1-(trifluoromethyl)propyl]benzamide Optical rotation: $[\alpha]_D^{20}=-16.9°$ (c=0.4352, DMSO).

(+)-1: (+)-N-[[4-(cyclopropylmethylsulfonyl)phenyl]methyl]-4-[1-hydroxy-1-(trifluoromethyl)propy)propyl]benzamide Optical rotation: $[\alpha]_D^{20}=+16.0°$ (c=0.4554, DMSO).

Following a procedure analogous to that described for Example 1, using the appropriate building blocks II and III or any commercially available ones, the following compounds were prepared.

2: N-[[4-(cyclopropylmethylsulfonyl)phenyl]methyl]-4-(2,2,2-trifluoro-1-hydroxy-1-methyl-ethyl)benzamide

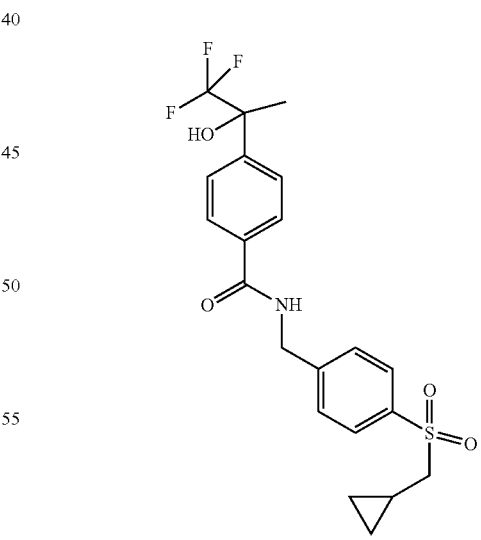

$MS(ES^+)$ m/z 442.0 $[M+H]^+$.

1H NMR (400 MHz, DMSO-d6) δ ppm 9.17 (t, J=6.02 Hz, 1H) 7.83-7.94 (m, 4H) 7.70 (d, J=8.28 Hz, 2H) 7.57 (d, J=8.28 Hz, 2H) 6.70 (s, 1H) 4.60 (d, J=5.77 Hz, 2H) 3.19-3.25 (m, 2H) 1.71 (s, 3H) 0.77-0.87 (m, 1H) 0.41-0.47 (m, 2H) 0.08-0.14 (m, 2H).

3: N-[[4-(cyclopropylmethylsulfonyl)phenyl]methyl]-4-(1-hydroxy-1-methyl-ethyl)benzamide

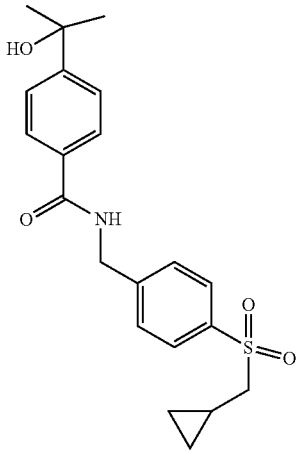 [SMILES: CC(C)(O)c1ccc(C(=O)NCc2ccc(S(=O)(=O)CC3CC3)cc2)cc1]

MS(ES+) m/z 388.2 [M+H]+.

1H NMR (400 MHz, DMSO-d6) δ ppm 9.06 (t, J=5.90 Hz, 1H) 7.82-7.88 (m, 4H) 7.56 (d, J=8.28 Hz, 4H) 5.10 (s, 1H) 4.58 (d, J=6.02 Hz, 2H) 3.22 (d, J=7.03 Hz, 2H) 1.44 (s, 6H) 0.77-0.87 (m, 1H) 0.41-0.47 (m, 2H) 0.09-0.14 (m, 2H).

4: N-[[4-(cyclopropylmethylsulfonyl)phenyl]methyl]-4-[2,2,2-trifluoro-1-hydroxy-1-(trifluoromethyl)ethyl]benzamide

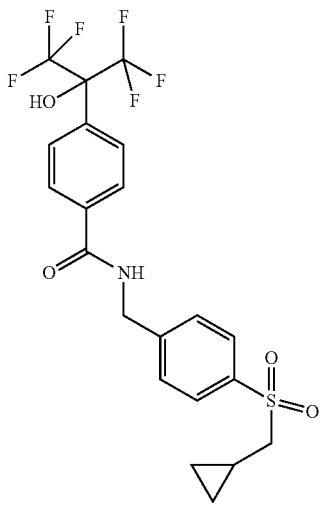 [SMILES: O=C(NCc1ccc(S(=O)(=O)CC2CC2)cc1)c1ccc(C(O)(C(F)(F)F)C(F)(F)F)cc1]

MS(ES+) m/z 496.2 [M+H]+.

1H NMR (400 MHz, DMSO-d6) δ ppm 9.2 (m, 1H) 8.8 (s, 1H) 7.9 (m, 2H) 7.7 (m, 2H) 7.6 (m, 2H) 7.5 (m, 2H) 4.5 (m, 2H) 3.1 (m, 2H) 0.7 (m, 1H) 0.3 (m, 2H) 0.0 (m, 2H).

5: N-[[4-(cyclopropylmethylsulfonyl)phenyl]methyl]-4-[1-(difluoromethyl)-2,2,2-trifluoro-1-hydroxy-ethyl]benzamide

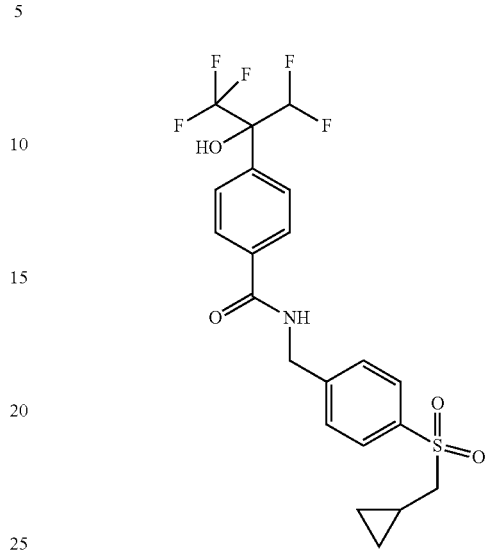

MS(ES+) m/z 478.1 [M+H]+.

1H NMR (400 MHz, DMSO-d6) δ ppm 9.23 (t, J=5.90 Hz, 1H) 7.98 (d, J=8.53 Hz, 2H) 7.93 (br s, 1H) 7.83-7.89 (m, 2H) 7.77 (d, J=8.53 Hz, 2H) 7.58 (d, J=8.53 Hz, 2H) 6.58-6.97 (m, 1H) 4.60 (d, J=6.02 Hz, 2H) 3.20-3.28 (m, 2H) 0.77-0.88 (m, 1H) 0.38-0.48 (m, 2H) 0.09-0.17 (m, 2H).

6: N-[[4-(cyclopropylmethylsulfonyl)phenyl]methyl]-4-[1-hydroxy-1-(trifluoromethyl)butyl]benzamide

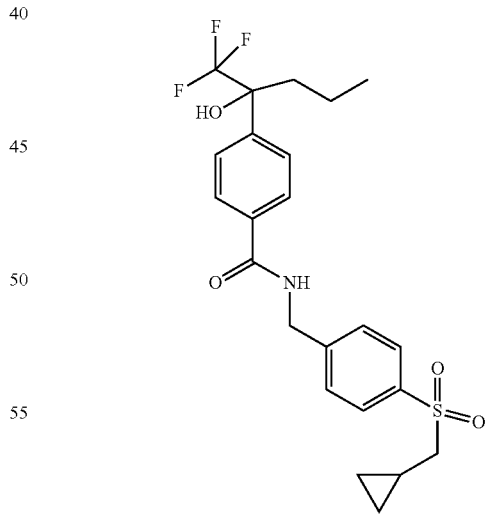

MS(ES+) m/z 470.1 [M+H]+.

1H NMR (400 MHz, DMSO-d6) δ ppm 9.16 (t, J=5.90 Hz, 1H) 7.83-7.93 (m, 4H) 7.65 (d, J=8.53 Hz, 2H) 7.57 (d, J=8.28 Hz, 2H) 6.52 (s, 1H) 4.59 (d, J=5.77 Hz, 2H) 3.22 (d, J=7.28 Hz, 2H) 2.13-2.22 (m, 1H) 1.90-1.99 (m, 1H) 1.26-1.38 (m, 1H) 0.77-0.89 (m, 5H) 0.41-0.46 (m, 2H) 0.09-0.13 (m, 2H).

7: N-[[4-(cyclopropylmethylsulfonyl)phenyl]methyl]-4-[1-hydroxy-1-(trifluoromethyl)pentyl]benzamide

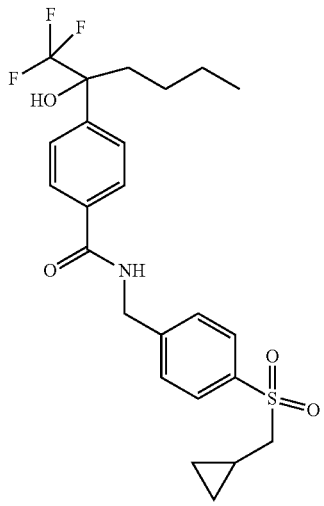 [SMILES: CCCCC(O)(c1ccc(C(=O)NCc2ccc(S(=O)(=O)CC3CC3)cc2)cc1)C(F)(F)F]

MS(ES+) m/z 484.1 [M+H]+.

1H NMR (400 MHz, DMSO-d6) δ ppm 9.16 (t, J=6.02 Hz, 1H) 7.91 (d, J=8.53 Hz, 2H) 7.85 (d, J=8.28 Hz, 2H) 7.65 (d, J=8.28 Hz, 2H) 7.58 (d, J=8.28 Hz, 2H) 6.51 (br s, 1H) 4.59 (d, J=6.02 Hz, 2H) 3.22 (d, J=7.03 Hz, 2H) 2.13-2.25 (m, 1H) 1.90-2.03 (m, 1H) 1.19-1.34 (m, 3H) 0.75-0.85 (m, 5H) 0.40-0.48 (m, 2H) 0.08-0.15 (m, 2H).

8: N-[[4-(cyclopropylmethylsulfonyl)phenyl]methyl]-4-[1-hydroxy-3-methyl-1-(trifluoromethyl)butyl]benzamide

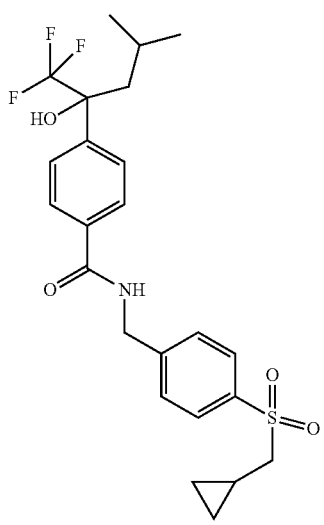 [SMILES: CC(C)CC(O)(c1ccc(C(=O)NCc2ccc(S(=O)(=O)CC3CC3)cc2)cc1)C(F)(F)F]

MS(ES+) m/z 484.1 [M+H]+.

1H NMR (400 MHz, DMSO-d6) δ ppm 9.17 (t, J=6.02 Hz, 1H) 7.83-7.93 (m, 4H) 7.67 (d, J=8.53 Hz, 2H) 7.58 (d, J=8.53 Hz, 2H) 6.51 (s, 1H) 4.59 (d, J=6.02 Hz, 2H) 3.18-3.28 (m, 2H) 2.16 (dd, J=14.18, 5.65 Hz, 1H) 1.86 (dd, J=14.31, 7.03 Hz, 1H) 1.52 (dquin, J=13.05, 6.53, 6.53, 6.53 Hz, 1H) 0.76-0.89 (m, 4H) 0.59 (d, J=6.53 Hz, 3H) 0.40-0.48 (m, 2H) 0.09-0.17 (m, 2H).

9: N-[[4-(cyclopropylmethylsulfonyl)phenyl]methyl]-4-[1-hydroxy-3,3-dimethyl-1-(trifluoromethyl)butyl]benzamide

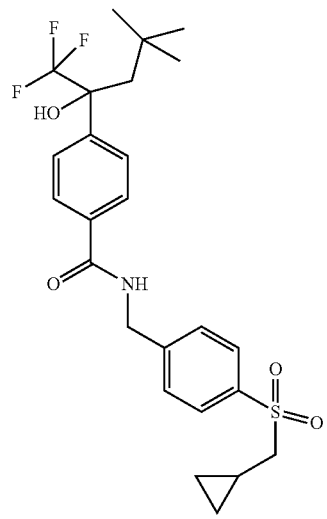 [SMILES: CC(C)(C)CC(O)(c1ccc(C(=O)NCc2ccc(S(=O)(=O)CC3CC3)cc2)cc1)C(F)(F)F]

MS(ES+) m/z 498.2 [M+H]+.

1H NMR (400 MHz, DMSO-d6) δ ppm 9.17 (t, J=6.02 Hz, 1H) 7.83-7.92 (m, 4H) 7.72 (d, J=8.28 Hz, 2H) 7.58 (d, J=8.28 Hz, 2H) 6.41 (s, 1H) 4.59 (d, J=6.02 Hz, 2H) 3.22 (d, J=7.03 Hz, 2H) 2.24 (d, J=14.31 Hz, 1H) 1.97 (d, J=14.56 Hz, 1H) 0.77-0.89 (m, 1H) 0.70-0.75 (m, 9H) 0.41-0.47 (m, 2H) 0.09-0.14 (m, 2H).

10: N-[[4-(cyclopropylmethylsulfonyl)phenyl]methyl]-4-[1-hydroxy-2-methyl-1-(trifluoromethyl)propyl]benzamide

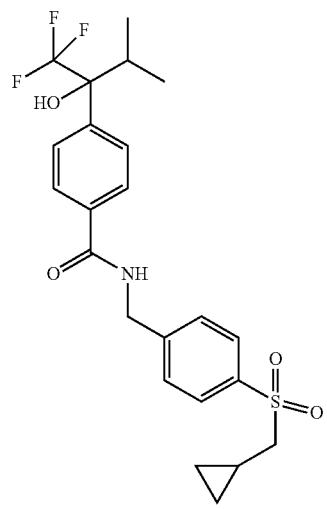 [SMILES: CC(C)C(O)(c1ccc(C(=O)NCc2ccc(S(=O)(=O)CC3CC3)cc2)cc1)C(F)(F)F]

MS(ES+) m/z 470.1 [M+H]+.

1H NMR (400 MHz, DMSO-d6) δ ppm 9.16 (t, J=5.90 Hz, 1H) 7.83-7.94 (m, 4H) 7.56-7.67 (m, 4H) 6.36 (br s, 1H)

4.59 (d, J=6.02 Hz, 2H) 3.20-3.25 (m, 2H) 2.47-2.51 (m, 1H) 1.07 (br d, J=6.27 Hz, 3H) 0.77-0.88 (m, 1H) 0.63 (d, J=6.78 Hz, 3H) 0.40-0.48 (m, 2H) 0.09-0.17 (m, 2H).

11: N-[[4-(cyclopropylmethylsulfonyl)phenyl]methyl]-4-(1-cyclopropyl-2,2,2-trifluoro-1-hydroxy-ethyl)benzamide

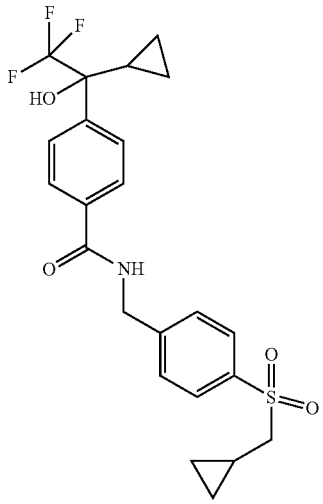 [SMILES: O=C(NCc1ccc(S(=O)(=O)CC2CC2)cc1)c1ccc(C(O)(C2CC2)C(F)(F)F)cc1]

MS(ES⁺) m/z 468.0 [M+H]⁺.

1H NMR (400 MHz, DMSO-d6) δ ppm 9.17 (t, J=6.02 Hz, 1H) 7.83-7.94 (m, 4H) 7.74 (d, J=8.53 Hz, 2H) 7.57 (d, J=8.28 Hz, 2H) 6.19 (s, 1H) 4.60 (d, J=6.02 Hz, 2H) 3.22 (d, J=7.28 Hz, 2H) 1.69 (tt, J=8.34, 5.21 Hz, 1H) 0.75-0.87 (m, 2H) 0.51-0.60 (m, 1H) 0.41-0.48 (m, 2H) 0.31-0.40 (m, 1H) 0.20-0.30 (m, 1H) 0.09-0.17 (m, 2H).

12: 4-(1-cyclopentyl-2,2,2-trifluoro-1-hydroxy-ethyl)-N-[[4-(cyclopropylmethylsulfonyl)phenyl]methyl]benzamide

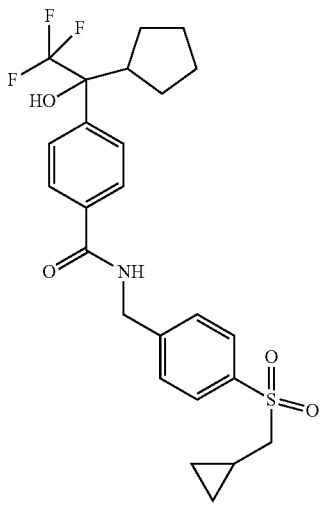 [SMILES: O=C(NCc1ccc(S(=O)(=O)CC2CC2)cc1)c1ccc(C(O)(C2CCCC2)C(F)(F)F)cc1]

MS(ES⁺) m/z 496.2 [M+H]⁺.

1H NMR (400 MHz, DMSO-d6) δ ppm 9.16 (t, J=6.00 Hz, 1H) 7.91 (m, J=8.53 Hz, 2H) 7.85 (m, J=8.28 Hz, 2H) 7.67 (m, J=8.53 Hz, 2H) 7.58 (m, J=8.28 Hz, 2H) 6.34 (s, 1H) 4.59 (d, J=6.02 Hz, 2H) 3.22 (d, J=7.03 Hz, 2H) 2.75 (quin, J=8.97 Hz, 1H) 1.33-1.89 (m, 6H) 1.04-1.27 (m, 2H) 0.72-0.94 (m, 1H) 0.41-0.46 (m, 2H) 0.09-0.13 (m, 2H).

13: N-[[4-(cyclopropylmethylsulfonyl)phenyl]methyl]-4-(2,2,2-trifluoro-1-hydroxy-1-phenyl-ethyl)benzamide

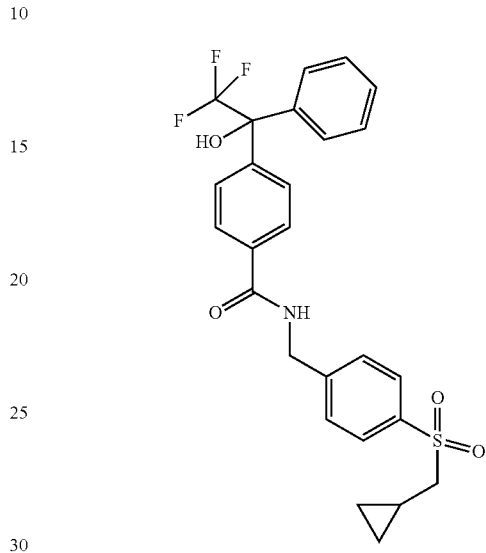

MS(ES⁺) m/z 504.0 [M+H]⁺.

1H NMR (400 MHz, DMSO-d6) δ ppm 9.17 (t, J=5.90 Hz, 1H) 7.83-7.93 (m, 4H) 7.34-7.58 (m, 10H) 4.59 (d, J=6.02 Hz, 2H) 3.19-3.28 (m, 2H) 0.76-0.88 (m, 1H) 0.41-0.46 (m, 2H) 0.08-0.13 (m, 2H).

14: 4-(1-benzyl-2,2,2-trifluoro-1-hydroxy-ethyl)-N-[[4-(cyclopropylmethylsulfonyl)phenyl]methyl]benzamide

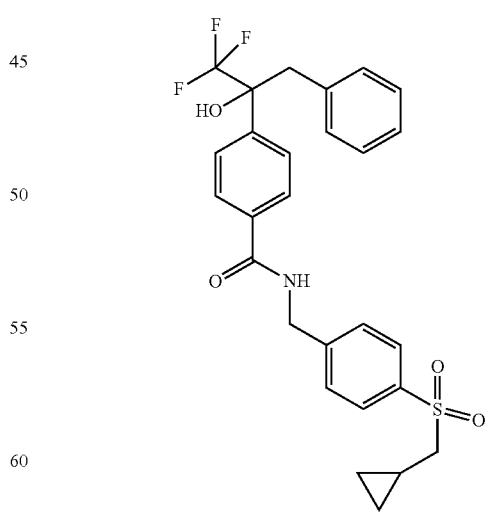

MS(ES⁺) m/z 518.1 [M+H]⁺.

1H NMR (400 MHz, DMSO-d6) δ ppm 9.12 (t, J=5.90 Hz, 1H) 7.83 (t, J=8.53 Hz, 4H) 7.63 (d, J=8.28 Hz, 2H) 7.56 (d, J=8.53 Hz, 2H) 7.03-7.14 (m, 5H) 6.87 (s, 1H) 4.56 (d, J=5.77 Hz, 2H) 3.55 (d, J=14.05 Hz, 1H) 3.31-3.39 (m, 1H) 3.19-3.28 (m, 2H) 0.76-0.86 (m, 1H) 0.40-0.47 (m, 2H) 0.08-0.15 (m, 2H)

15: N-[[4-(cyclopropylmethylsulfonyl)phenyl]methyl]-3-methyl-4-[2,2,2-trifluoro-1-hydroxy-1-(trifluoromethyl)ethyl]benzamide

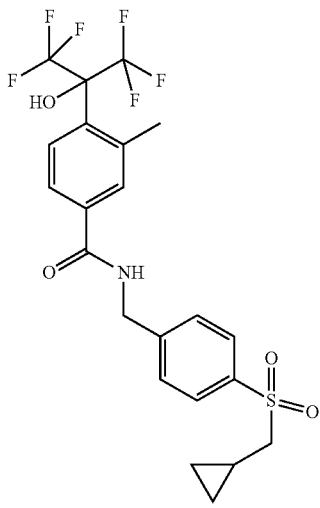 [SMILES: Cc1cc(C(=O)NCc2ccc(S(=O)(=O)CC3CC3)cc2)ccc1C(O)(C(F)(F)F)C(F)(F)F]

MS(ES+) m/z 510.1 [M+H]+.

1H NMR (400 MHz, DMSO-d6) δ ppm 9.21 (t, J=5.90 Hz, 1H) 8.67 (br s, 1H) 7.76-7.87 (m, 4H) 7.55-7.61 (m, 3H) 4.59 (d, J=6.02 Hz, 2H) 3.22 (d, J=7.03 Hz, 2H) 2.64 (s, 3H) 0.77-0.87 (m, 1H) 0.40-0.48 (m, 2H) 0.09-0.17 (m, 2H).

16: N-[[4-(cyclopropylmethylsulfonyl)phenyl]methyl]-5-[2,2,2-trifluoro-1-hydroxy-1-(trifluoromethyl)ethyl]pyridine-2-carboxamide

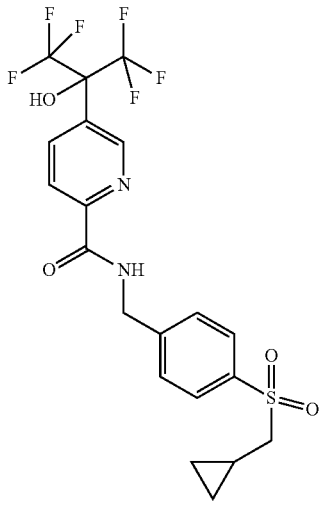 [SMILES: O=C(NCc1ccc(S(=O)(=O)CC2CC2)cc1)c1ccc(C(O)(C(F)(F)F)C(F)(F)F)cn1]

MS(ES+) m/z 497.0 [M+H]+.

17: N-[(4-ethylsulfonylphenyl)methyl]-4-[1-hydroxy-1-(trifluoromethyl)propyl]benzamide

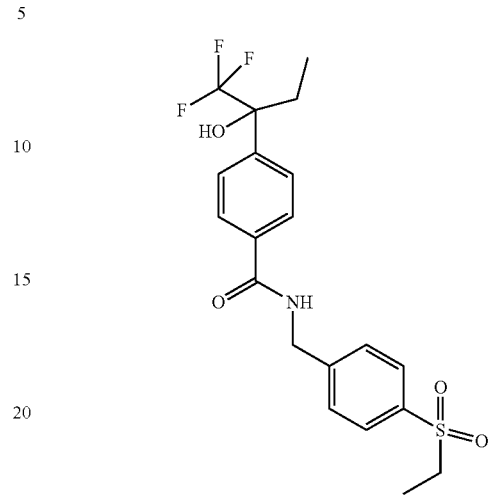

MS(ES+) m/z 430.1 [M+H]+.

1H NMR (400 MHz, DMSO-d6) δ ppm 9.17 (t, J=5.90 Hz, 1H) 7.92 (d, J=8.53 Hz, 2H) 7.81-7.87 (m, 2H) 7.65 (d, J=8.53 Hz, 2H) 7.59 (d, J=8.53 Hz, 2H) 6.49 (s, 1H) 4.59 (d, J=6.02 Hz, 2H) 3.25 (q, J=7.36 Hz, 2H) 2.23 (dq, J=14.31, 7.36 Hz, 1H) 1.97-2.08 (m, 1H) 1.09 (t, J=7.28 Hz, 3H) 0.67 (t, J=7.28 Hz, 3H).

18: N-[(4-ethylsulfonylphenyl)methyl]-4-[1-hydroxy-3,3-dimethyl-1-(trifluoromethyl)butyl]benzamide

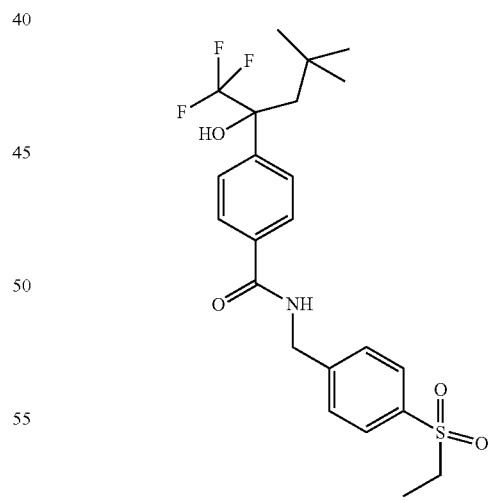

MS(ES+) m/z 472.1 [M+H]+.

1H NMR (400 MHz, DMSO-d6) δ ppm 9.17 (t, J=5.90 Hz, 1H) 7.90 (d, J=8.78 Hz, 2H) 7.82-7.87 (m, 2H) 7.72 (d, J=8.28 Hz, 2H) 7.59 (d, J=8.53 Hz, 2H) 6.40 (s, 1H) 4.58 (d, J=5.77 Hz, 2H) 3.25 (q, J=7.36 Hz, 2H) 2.24 (d, J=14.56 Hz, 1H) 1.97 (d, J=14.56 Hz, 1H) 1.09 (t, J=7.40 Hz, 3H) 0.72 (s, 9H).

19: N-[(4-ethylsulfonylphenyl)methyl]-4-[2,2,2-trifluoro-1-hydroxy-1-(trifluoromethyl)ethyl]benzamide

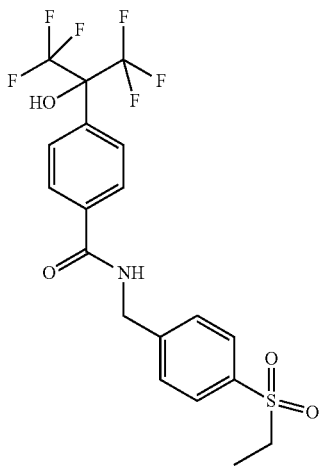 [SMILES: CCS(=O)(=O)c1ccc(CNC(=O)c2ccc(C(O)(C(F)(F)F)C(F)(F)F)cc2)cc1]

21: N-[[4-(cyclopropylsulfamoyl)phenyl]methyl]-4-[2,2,2-trifluoro-1-hydroxy-1-(trifluoromethyl)ethyl]benzamide

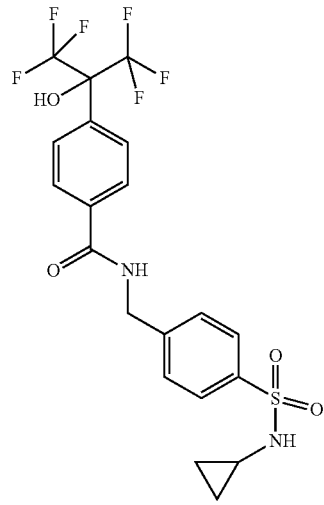

MS(ES+) m/z 497.2 [M+H]+.

20: N-[[4-(cyclopropylsulfamoyl)phenyl]methyl]-4-[1-hydroxy-1-(trifluoromethyl)pentyl]benzamide 22: N-[[4-(cyclopropylmethylsulfonyl)phenyl]methyl]-4-[2,2,2-trifluoro-1-methoxy-1-(trifluoromethyl)ethyl]benzamide

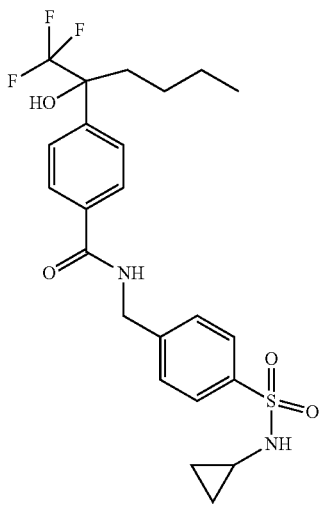 [SMILES: CCCCC(O)(c1ccc(C(=O)NCc2ccc(S(=O)(=O)NC3CC3)cc2)cc1)C(F)(F)F]

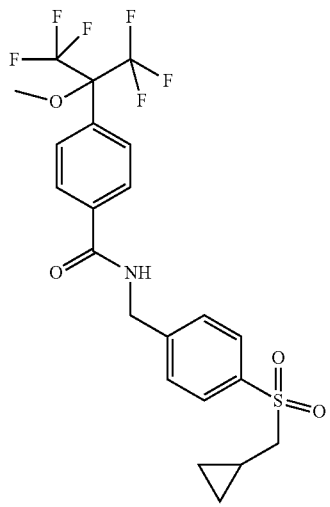 [SMILES: COC(c1ccc(C(=O)NCc2ccc(S(=O)(=O)CC3CC3)cc2)cc1)(C(F)(F)F)C(F)(F)F]

MS(ES+) m/z 485.1 [M+H]+.

1H NMR (400 MHz, DMSO-d6) δ ppm 9.14 (t, J=5.90 Hz, 1H) 7.91 (d, J=8.53 Hz, 2H) 7.85 (br s, 1H) 7.77 (m, J=8.28 Hz, 2H) 7.65 (m, J=8.28 Hz, 2H) 7.53 (d, J=8.28 Hz, 2H) 6.51 (s, 1H) 4.57 (d, J=6.02 Hz, 2H) 2.15-2.24 (m, 1H) 2.07 (tt, J=6.87, 3.54 Hz, 1H) 1.92-2.01 (m, 1H) 1.19-1.33 (m, 3H) 0.75-0.83 (m, 4H) 0.35-0.49 (m, 4H).

MS(ES+) m/z 510.1 [M+H]+.

1H NMR (400 MHz, DMSO-d6) δ ppm 9.33 (s, 1H) 8.07-8.10 (m, 2H) 7.84-7.87 (m, 2H) 7.71 (d, J=8.28 Hz, 2H) 7.59 (d, J=8.53 Hz, 2H) 4.61 (d, J=6.02 Hz, 2H) 3.48 (s, 3H) 3.23 (d, J=7.28 Hz, 2H) 0.77-0.88 (m, 1H) 0.42-0.46 (m, 2H) 0.08-0.15 (m, 2H).

23: N-[[4-(cyclopropylmethylsulfonyl)phenyl]methyl]-4-[1-ethoxy-2,2,2-trifluoro-1-(trifluoromethyl)ethyl]benzamide

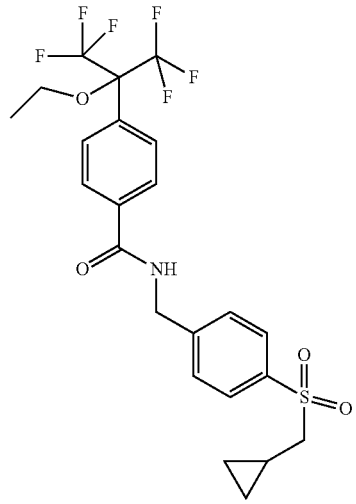 [SMILES: CCOC(c1ccc(C(=O)NCc2ccc(S(=O)(=O)CC3CC3)cc2)cc1)(C(F)(F)F)C(F)(F)F]

MS(ES⁺) m/z 524.1 [M+H]⁺.
1H NMR (400 MHz, DMSO-d6) δ ppm 9.32 (t, J=5.90 Hz, 1H) 8.08 (d, J=8.78 Hz, 2H) 7.86 (d, J=8.53 Hz, 2H) 7.70 (d, J=8.28 Hz, 2H) 7.58 (d, J=8.28 Hz, 2H) 4.61 (d, J=6.02 Hz, 2H) 3.61 (q, J=7.03 Hz, 2H) 3.20-3.28 (m, 2H) 1.31 (t, J=7.03 Hz, 3H) 0.77-0.87 (m, 1H) 0.41-0.47 (m, 2H) 0.09-0.14 (m, 2H).

24: N-[[4-(cyclopropylmethylsulfonyl)phenyl]methyl]-4-[2,2,2-trifluoro-1-propoxy-1-(trifluoromethyl)ethyl]benzamide

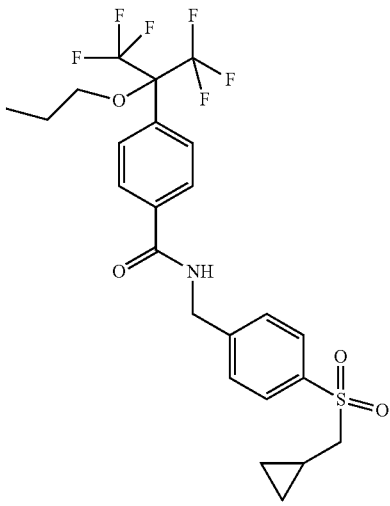 [SMILES: CCCOC(c1ccc(C(=O)NCc2ccc(S(=O)(=O)CC3CC3)cc2)cc1)(C(F)(F)F)C(F)(F)F]

MS(ES⁺) m/z 538.1 [M+H]⁺.
1H NMR (400 MHz, DMSO-d6) δ ppm 9.31 (t, J=5.90 Hz, 1H) 8.06-8.10 (m, 2H) 7.84-7.87 (m, 2H) 7.69 (m, J=8.28 Hz, 2H) 7.58 (m, J=8.53 Hz, 2H) 4.61 (d, J=6.02 Hz, 2H) 3.51 (t, J=6.40 Hz, 2H) 3.20-3.29 (m, 2H) 1.72 (sxt, J=7.08 Hz, 2H) 0.94 (t, J=7.40 Hz, 3H) 0.77-0.87 (m, 1H) 0.41-0.46 (m, 2H) 0.09-0.13 (m, 2H).

25: 4-[1-butoxy-2,2,2-trifluoro-1-(trifluoromethyl)ethyl]-N-[[4-(cyclopropylmethylsulfonyl)phenyl]methyl]benzamide

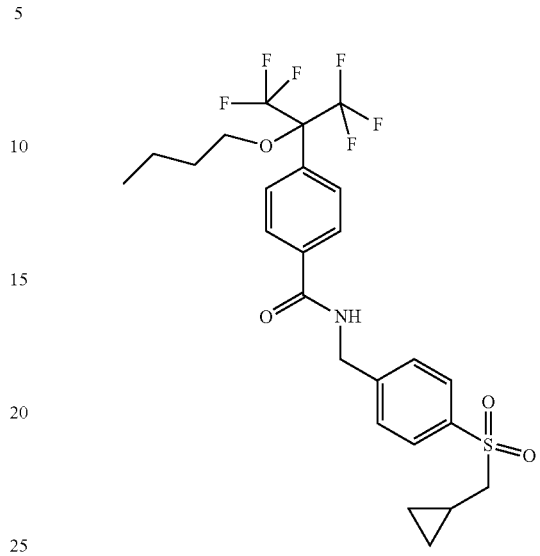

MS(ES⁺) m/z 552.1 [M+H]⁺.
1H NMR (400 MHz, DMSO-d6) δ ppm 9.31 (t, J=6.02 Hz, 1H) 8.07 (d, J=7.96 Hz, 2H) 7.84-7.88 (m, 2H) 7.69 (m, J=8.28 Hz, 2H) 7.59 (d, J=8.53 Hz, 2H) 4.61 (d, J=6.02 Hz, 2H) 3.55 (t, J=6.53 Hz, 2H) 3.23 (d, J=7.03 Hz, 2H) 1.64-1.72 (m, 2H) 1.40 (dq, J=15.00, 7.38 Hz, 2H) 0.91 (t, J=7.40 Hz, 3H) 0.77-0.87 (m, 1H) 0.41-0.47 (m, 2H) 0.09-0.14 (m, 2H).

26: N-[[4-(cyclopropylmethylsulfonyl)phenyl]methyl]-4-[2,2,2-trifluoro-1-isopropoxy-1-(trifluoromethyl)ethyl]benzamide

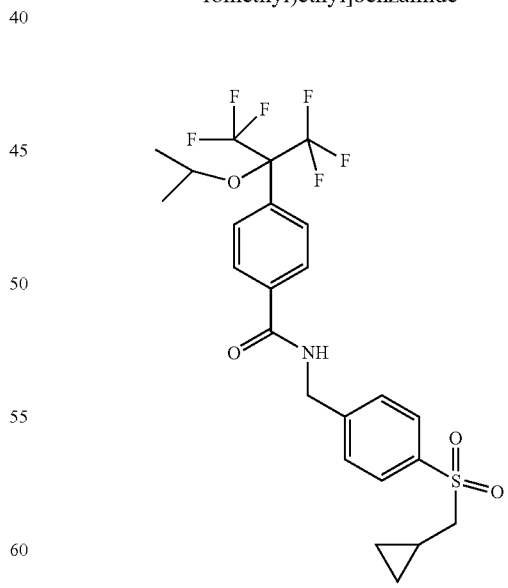

MS(ES⁺) m/z 538.1 [M+H]⁺.
1H NMR (400 MHz, DMSO-d6) δ ppm 9.31 (t, J=5.90 Hz, 1H) 8.06 (d, J=7.89 Hz, 2H) 7.86 (d, J=7.77 Hz, 2H) 7.77 (d, J=8.28 Hz, 2H) 7.59 (d, J=8.28 Hz, 2H) 4.61 (d, J=6.02 Hz, 2H) 3.98 (dt, J=12.05, 6.02 Hz, 1H) 3.21-3.28 (m, 2H) 1.25 (d, J=6.02 Hz, 6H) 0.77-0.87 (m, 1H) 0.41-0.47 (m, 2H) 0.09-0.15 (m, 2H).

27: 4-[1-benzyloxy-2,2,2-trifluoro-1-(trifluoromethyl)ethyl]-N-[[4-(cyclopropylmethylsulfonyl)phenyl]methyl]benzamide

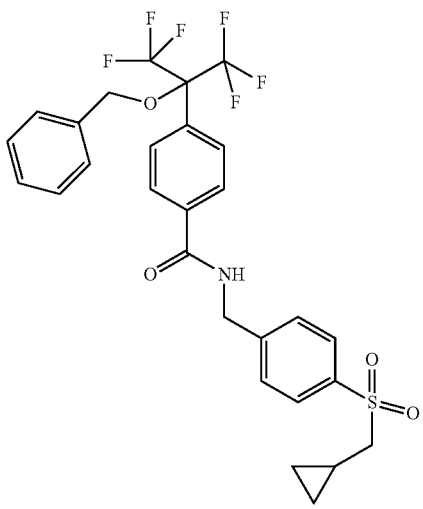 [SMILES: O=C(NCc1ccc(S(=O)(=O)CC2CC2)cc1)c1ccc(C(OCc2ccccc2)(C(F)(F)F)C(F)(F)F)cc1]

MS(ES⁺) m/z 586.1 [M+H]⁺.

1H NMR (400 MHz, DMSO-d6) δ ppm 9.33 (t, J=6.02 Hz, 1H) 8.11 (d, J=8.78 Hz, 2H) 7.85 (d, J=7.93 Hz, 2H) 7.75 (d, J=8.28 Hz, 2H) 7.59 (d, J=8.28 Hz, 2H) 7.37-7.47 (m, 5H) 4.60-4.67 (m, 4H) 3.20-3.27 (m, 2H) 0.77-0.87 (m, 1H) 0.40-0.46 (m, 2H) 0.09-0.14 (m, 2H).

28: N-[[4-(cyclopropylmethylsulfonyl)-2-methylphenyl]methyl]-4-[2,2,2-trifluoro-1-methoxy-1-(trifluoromethyl)ethyl]benzamide

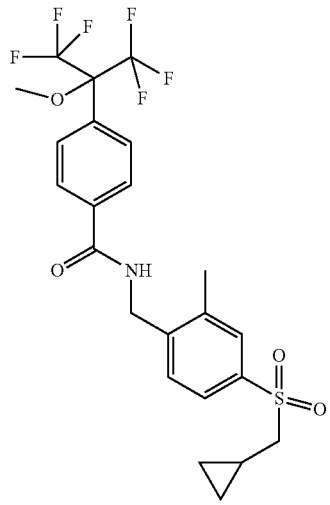 [SMILES: COC(c1ccc(C(=O)NCc2ccc(S(=O)(=O)CC3CC3)cc2C)cc1)(C(F)(F)F)C(F)(F)F]

MS(ES⁺) m/z 524.1 [M+H]⁺.

1H NMR (400 MHz, DMSO-d6) δ ppm 9.22 (t, J=5.77 Hz, 1H) 8.09 (d, J=7.27 Hz, 2H) 7.67-7.74 (m, 4H) 7.49 (d, J=8.03 Hz, 1H) 4.56 (d, J=5.77 Hz, 2H) 3.48 (s, 3H) 3.20-3.25 (m, 2H) 2.44 (s, 3H) 0.78-0.87 (m, 1H) 0.42-0.48 (m, 2H) 0.11-0.16 (m, 2H).

29: N-[[4-(cyclopropylmethylsulfonyl)-2-methylphenyl]methyl]-4-[1-ethoxy-2,2,2-trifluoro-1-(trifluoromethyl)ethyl]benzamide

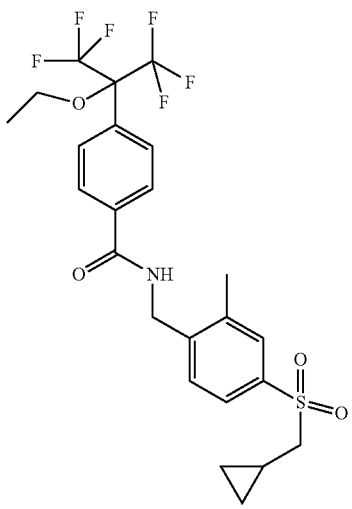 [SMILES: CCOC(c1ccc(C(=O)NCc2ccc(S(=O)(=O)CC3CC3)cc2C)cc1)(C(F)(F)F)C(F)(F)F]

MS(ES⁺) m/z 538.2 [M+H]⁺.

1H NMR (400 MHz, DMSO-d6) δ ppm 9.21 (t, J=5.77 Hz, 1H) 8.08 (d, J=8.53 Hz, 2H) 7.67-7.73 (m, 4H) 7.49 (d, J=8.03 Hz, 1H) 4.56 (d, J=5.77 Hz, 2H) 3.61 (q, J=6.78 Hz, 2H) 3.19-3.25 (m, 2H) 2.44 (s, 3H) 1.31 (t, J=6.90 Hz, 3H) 0.77-0.87 (m, 1H) 0.42-0.47 (m, 2H) 0.11-0.15 (m, 2H).

30: N-[[4-(cyclopropylsulfamoyl)phenyl]methyl]-4-[2,2,2-trifluoro-1-methoxy-1-(trifluoromethyl)ethyl]benzamide

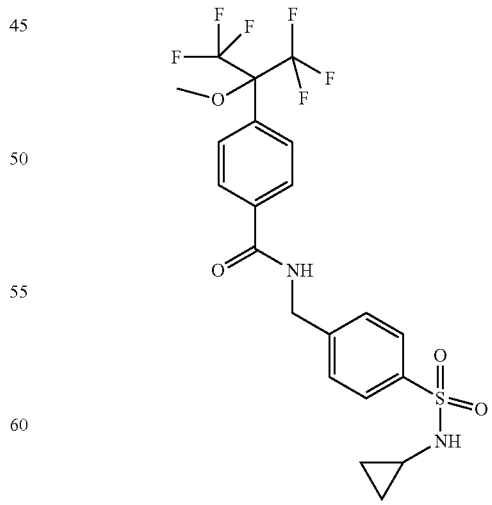

MS(ES⁺) m/z 511.0 [M+H]+.

1H NMR (500 MHz, DMSO-d6) δ ppm 9.31 (t, J=5.87 Hz, 1H) 8.09 (d, J=8.56 Hz, 2H) 7.86 (br s, 1H) 7.77 (m, J=8.31 Hz, 2H) 7.71 (m, J=8.31 Hz, 2H) 7.54 (d, J=8.31 Hz, 2H) 4.59 (d, J=5.87 Hz, 2H) 3.48 (s, 3H) 2.05-2.10 (m, 1H) 0.36-0.48 (m, 4H).

31: N-[[4-(cyclopropylsulfamoyl)phenyl]methyl]-4-[1-ethoxy-2,2,2-trifluoro-1-(trifluoromethyl)ethyl]benzamide

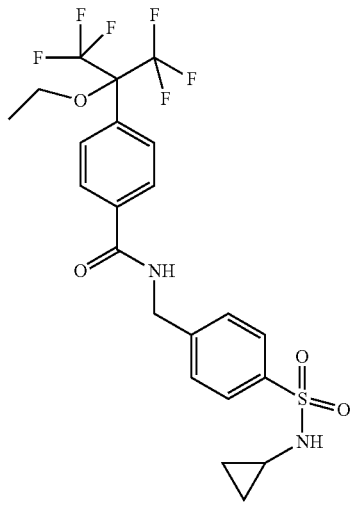 [SMILES: CCOC(c1ccc(C(=O)NCc2ccc(S(=O)(=O)NC3CC3)cc2)cc1)(C(F)(F)F)C(F)(F)F]

MS(ES+) m/z 525.1 [M+H]+.

1H NMR (500 MHz, DMSO-d6) δ ppm 9.30 (br s, 1H) 8.08 (br d, J=8.31 Hz, 2H) 7.86 (br s, 1H) 7.77 (m, J=7.82 Hz, 2H) 7.70 (m, J=7.82 Hz, 2H) 7.54 (br d, J=7.82 Hz, 2H) 4.59 (br d, J=4.89 Hz, 2H) 3.61 (br d, J=6.60 Hz, 2H) 2.07 (br s, 1H) 1.31 (br t, J=6.72 Hz, 3H) 0.46 (br d, J=5.14 Hz, 2H) 0.37 (br s, 2H).

32: N-[[4-(cyclopropylsulfamoyl)phenyl]methyl]-4-[2,2,2-trifluoro-1-propoxy-1-(trifluoromethyl)ethyl]benzamide

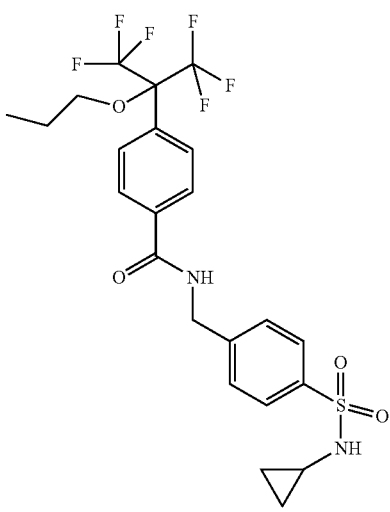 [SMILES: CCCOC(c1ccc(C(=O)NCc2ccc(S(=O)(=O)NC3CC3)cc2)cc1)(C(F)(F)F)C(F)(F)F]

MS(ES+) m/z 539.1 [M+H]+.

1H NMR (400 MHz, DMSO-d6) δ ppm 9.29 (br t, J=5.90 Hz, 1H) 8.08 (br d, J=8.53 Hz, 2H) 7.85 (br s, 1H) 7.77 (br d, J=8.28 Hz, 2H) 7.69 (br d, J=8.03 Hz, 2H) 7.54 (br d, J=8.28 Hz, 2H) 4.59 (br d, J=5.77 Hz, 2H) 3.51 (br t, J=6.27 Hz, 2H) 2.07 (br s, 1H) 1.67-1.76 (m, 2H) 0.94 (t, J=7.40 Hz, 3H) 0.35-0.50 (m, 4H).

33: N-[[4-(cyclopropylmethylsulfonyl)phenyl]methyl]-4-[1-methoxy-3,3-dimethyl-1-(trifluoromethyl)butyl]benzamide

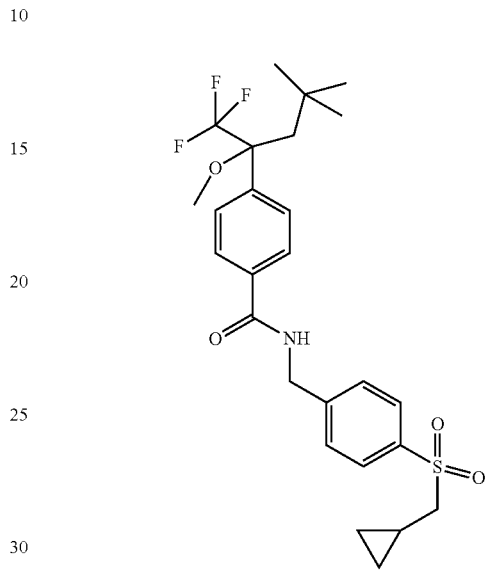

MS(ES+) m/z 512.2 [M+H]+.

1H NMR (400 MHz, DMSO-d6) δ ppm 9.09 (t, J=5.90 Hz, 1H) 7.73-7.83 (m, 4H) 7.62 (d, J=8.28 Hz, 2H) 7.47 (d, J=8.28 Hz, 2H) 4.48 (d, J=5.77 Hz, 2H) 3.42 (d, J=2.01 Hz, 3H) 3.12 (d, J=7.03 Hz, 2H) 2.14-2.23 (m, 1H) 2.00-2.06 (m, 1H) 0.67-0.77 (m, 1H) 0.64 (s, 9H) 0.29-0.37 (m, 2H) −0.01-0.03 (m, 2H).

34: N-[(1R)-1-[4-(cyclopropylmethylsulfonyl)phenyl]ethyl]-4-[2,2,2-trifluoro-1-hydroxy-1-(trifluoromethyl)ethyl]benzamide

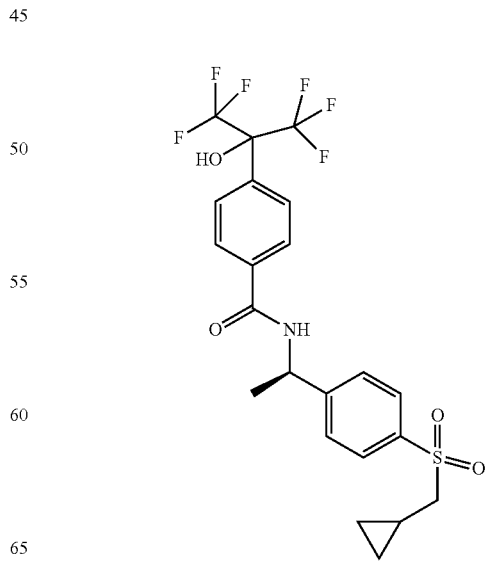

i) To a solution of N-[(1R)-1-(4-bromophenyl)ethyl]-4-[2,2,2-trifluoro-1-hydroxy-1-(trifluoromethyl)ethyl]benzamide (250 mg) in dimethyl sulfoxide (3 mL) were added sodium sulfinatomethylcyclopropane (110 mg), (+/−)-trans-cyclohexane-1,2-diamine (26 µl), copper(I) trifluoromethanesulfonate benzene complex (45 mg). The resulting mixture was heated to 12500 under microwave irradiation for 1 hour. The reaction mixture was poured into water/ether and extracted three times with ether. The combined extracts were concentrated under reduced pressure, taken up in DCM/water, filtered on a water repellent filter cartridge and concentrated under reduced pressure. The residue was purified by column chromatography on silica gel, using 10% to 30% EtOAc in heptane as the eluent, followed by trituration with ether/pentane to obtain 75 mg of the expected product. MS(ES+) m/z 510.1 [M+H]+.

1H NMR (400 MHz, DMSO-d6) δ ppm 9.03 (d, J=7.78 Hz, 1H) 8.89 (br s, 1H) 7.97-8.03 (m, 2H) 7.83-7.88 (m, 2H) 7.79 (d, J=8.28 Hz, 2H) 7.65 (d, J=8.28 Hz, 2H) 5.24 (quin, J=7.22 Hz, 1H) 3.22 (d, J=7.28 Hz, 2H) 1.51 (d, J=7.03 Hz, 3H) 0.76-0.89 (m, 1H) 0.40-0.49 (m, 2H) 0.09-0.16 (m, 2H).

35: N-[(1S)-1-[4-(cyclopropylmethylsulfonyl)phenyl]ethyl]-4-[2,2,2-trifluoro-1-hydroxy-1-(trifluoromethyl)ethyl]benzamide

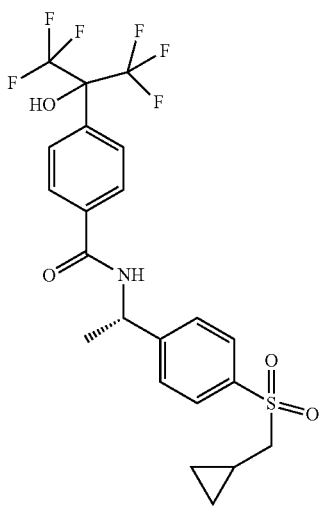 [SMILES: C[C@H](NC(=O)c1ccc(C(O)(C(F)(F)F)C(F)(F)F)cc1)c1ccc(S(=O)(=O)CC2CC2)cc1]

MS(ES+) m/z 510.1 [M+H]+.

1H NMR (400 MHz, DMSO-d6) δ ppm 9.03 (d, J=7.78 Hz, 1H) 8.88 (br s, 1H) 7.99 (d, J=7.96 Hz, 2H) 7.85 (d, J=7.84 Hz, 2H) 7.79 (d, J=8.28 Hz, 2H) 7.65 (d, J=8.28 Hz, 2H) 5.24 (t, J=7.15 Hz, 1H) 3.22 (d, J=7.03 Hz, 2H) 1.51 (d, J=7.03 Hz, 3H) 0.75-0.89 (m, 1H) 0.42-0.47 (m, 2H) 0.10-0.14 (m, 2H).

Examples 36-38

36: N-[[4-(cyclopropylmethylsulfonyl)phenyl]methyl]-4-[1-hydroxy-2-methyl-1-(5-methylisoxazol-3-yl) propyl]benzamide

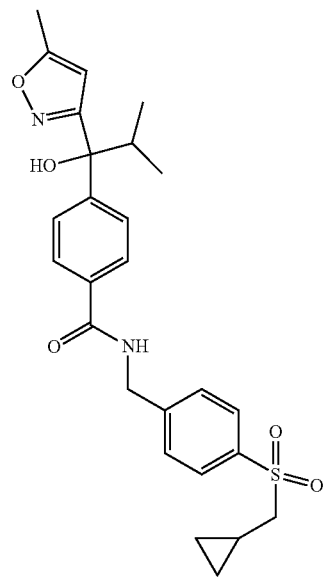 [SMILES: Cc1cc(C(O)(c2ccc(C(=O)NCc3ccc(S(=O)(=O)CC4CC4)cc3)cc2)C(C)C)no1]

i) To a solution of methyl-4-chlorocarbonylbenzoate (1.2 g) in anhydrous acetonitrile (10 mL) was added portionwise 1H-imidazole (747 mg). The reaction mixture was stirred for 1 hour at RT. The reaction mixture was then poured into water (60 mL) and extracted with EtOAc (3×100 mL). The combined extracts were washed with brine (50 mL), dried over MgSO4 and concentrated under reduced pressure to obtain 1.25 g of methyl 4-(1H-imidazole-1-carbonyl)benzoate. MS(ES+) m/z 231 [M+H]+.

ii) To a solution of potassium tert-butoxide (1.21 mg) in anhydrous THF (25 mL) was added dropwise nitromethane (662 mg) under nitrogen atmosphere. The reaction mixture was stirred for 20 min at RT. Then, methyl 4-(1H-imidazole-1-carbonyl)benzoate (1.25 g) was added dropwise. The reaction mixture was stirred overnight at reflux. The nitronate salt was filtered off, washed with dichloromethane (2×50 mL) and dissolved in cold water (100 mL). The aqueous solution was acidified slowly with 2M HCl to pH 3 and extracted with AcOEt (3×50 mL). The combined extracts were washed with brine (50 mL), dried over MgSO4 and concentrated under reduced pressure to give 338 mg of methyl 4-(2-nitroacetyl)benzoate. MS(ES+) m/z 224 [M+H]+.

iii) A solution of methyl 4-(2-nitroacetyl)benzoate (670 mg) and PTSA (34.6 mg) in isopropenyl acetate (5 ml) was refluxed in an atmosphere of dry nitrogen for 5 hours. The clear, dark-brown reaction mixture was then poured into water (10 mL) and extracted with EtOAc (3×30 mL). The combined extracts were washed with brine (50 mL), dried over MgSO4 and concentrated under reduced pressure. The residue was purified by column chromatography on silica gel, using 0% to 20% EtOAc in heptane as the eluent to obtain 490 mg of methyl 4-(5-methylisoxazole-3-carbonyl) benzoate. MS(ES$^+$) m/z 246 [M+H]$^+$.

iv) To a solution of the compound obtained in the preceding step (345 mg) in THF (10 mL) was added water (10 ml) and LiOH (40 mg). After stirring for 2 hours at RT, the reaction was not complete. Additional LiOH (40 mg) was added. The resulting mixture was stirred vigorously for an additional 3 hours at RT. The reaction mixture was concentrated under reduced pressure and then, the crude residue was poured into water (10 mL). The aqueous solution was acidified slowly with 2M HCl to pH 2 and the precipitate obtained was filtered off, washed with water (15 mL) and dried under reduced pressure to give 307 mg of 4-(5-methylisoxazole-3-carbonyl)benzoic acid. MS(ES$^+$) m/z 232 [M+H]$^+$.

V) To a solution of 4-(5-methylisoxazole-3-carbonyl) benzoic acid (307 mg) in DMF (15 mL) was added TEA (407 µL) and HBTU (679 mg). The reaction mixture was stirred at RT for 15 minutes. Amine II-1 (382 mg) was added and the reaction mixture was stirred for 6 hour at RT. DMF was removed by rotary evaporation under reduced pressure and crude residue was then poured into water (25 mL) and extracted with EtOAc (3×30 mL). The combined extracts were washed with brine (2×20 mL), dried over MgSO$_4$ and concentrated under reduced pressure. The residue was purified by column chromatography on silica gel, using 0% to 20% EtOAc in heptane as the eluent to obtain 465 mg of N-[4-((cyclopropylmethyl)sulfonyl)benzyl]-4-(5-methyl-isoxazole-3-carbonyl)benzamide. MS(ES$^+$) m/z 439 [M+H]$^+$.

vi) To a solution of N-[4-((cyclopropylmethyl)sulfonyl) benzyl]-4-(5-methylisoxazole-3-carbonyl)benzamide (100 mg) in anhydrous THF (5 mL) at 0° C., under nitrogen atmosphere, was added dropwise isopropyl magnesium bromide (197 µL, 2.9 M in methyltetrahydrofurane). The reaction mixture was stirred for 3 hours at RT. The reaction mixture was then poured into water (15 mL) and extracted with EtOAc (3×20 mL). The combined extracts were washed with brine (50 mL), dried over MgSO$_4$ and concentrated under reduced pressure. The residue was purified by column chromatography on silica gel, using 0% to 20% EtOAc in dichloromethane as the eluent to obtain 59 mg of N-[(4-(cyclopropylmethylsulfonyl)phenyl)methyl]-4-[1-hydroxy-2-methyl-1-(5-methylisoxazol-3-yl) propyl]benzamide. MS(ES$^+$) m/z 483 [M+H]$^+$.

1H NMR (400 MHz, DMSO-d6) δ ppm 9.12 (t, J=6.14 Hz, 1H) 7.82-7.84 (m, 4H) 7.53-7.57 (m, 4H) 6.16 (s, 1H) 5.82 (s, 1H) 4.57 (d, J=5.34 Hz, 2H) 3.23 (d, J=7.20 Hz, 2H) 2.60-2.64 (m, 1H) 2.32 (s, 3H) 0.92 (d, J=6.66 Hz, 3H) 0.76-0.83 (m, 1H) 0.67 (d, J=6.66 Hz, 3H) 0.41-0.43 (m, 2H) 0.08-0.10 (m, 2H).

Following a procedure analogous to that described for Example 36, using the appropriate building blocks II or any commercially available ones, the following compounds were prepared.

37: 4-[cyclopropyl-hydroxy-(5-methylisoxazol-3-yl) methyl]-N-[[4-(cyclopropylmethylsulfonyl)phenyl] methyl]benzamide

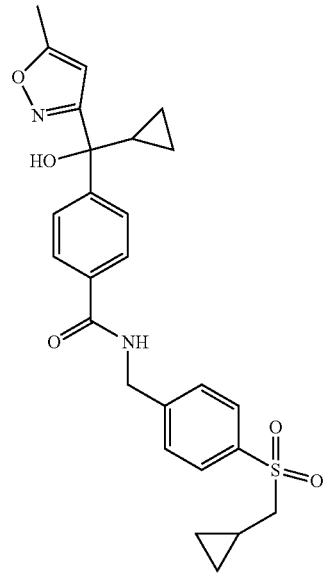 [SMILES: Cc1cc(C(O)(c2ccc(C(=O)NCc3ccc(S(=O)(=O)CC4CC4)cc3)cc2)C2CC2)no1]

MS(ES$^+$) m/z 481 [M+H]$^+$.
1H NMR (400 MHz, DMSO-d6) δ ppm 9.12 (t, J=6.05 Hz, 1H) 7.83-7.85 (m, 4H) 7.53-7.56 (m, 4H) 6.14 (s, 1H) 5.80 (s, 1H) 4.57 (d, J=5.87 Hz, 2H) 3.22 (d, J=7.20 Hz, 2H) 2.35 (s, 3H) 1.66-1.72 (m, 1H) 0.77-0.85 (m, 1H) 0.58-0.61 (m, 1H) 0.40-0.43 (m, 3H) 0.32-0.38 (m, 2H) 0.09-0.16 (m, 2H)

38: N-[(4-(cyclopropylmethylsulfonyl)phenyl) methyl]-4-[1-hydroxy-2,2-dimethyl-1-(5-methyl-isoxazol-3-yl)propyl]benzamide

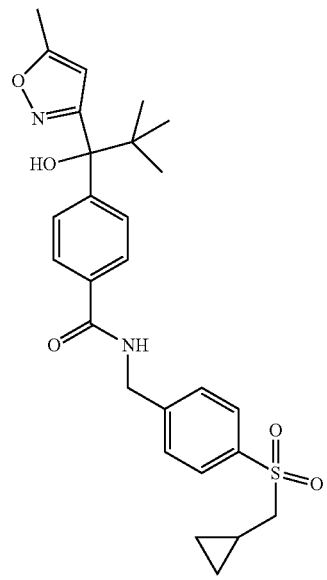 [SMILES: Cc1cc(C(O)(c2ccc(C(=O)NCc3ccc(S(=O)(=O)CC4CC4)cc3)cc2)C(C)(C)C)no1]

MS(ES$^+$) m/z 497 [M+H]$^+$.

1H NMR (400 MHz, DMSO-d6) δ ppm 9.12 (t, J=6.14 Hz, 1H) 7.82-7.85 (m, 4H) 7.66-7.68 (d J=8.09 Hz, 2H) 7.54-7.56 (d, J=8.09 Hz, 2H) 6.15 (s, 1H) 5.99 (s, 1H) 4.57 (d, J=5.39 Hz, 2H) 3.24 (d, J=7.15 Hz, 2H) 2.37 (s, 3H) 0.95 (s, 9H) 0.78-0.85 (m, 1H) 0.40-0.48 (m, 2H) 0.08-0.14 (m, 2H)

Example 39

RORγ GAL4 Reporter Gene Assay

Example inhibitors 1-38 were tested for their ability to inhibit RORγ activity in a RORγ GAL4 reporter gene assay. The assay procedure and results are described below.

RORγ GAL4 Reporter Gene Assay Description

A GAL4 one-hybrid reporter system employing luciferase readout was established to determine inhibition of RORγ in 293FT cells. The RORγ ligand-binding domain (LBD) was fused to the yeast GAL4 DNA binding domain (DBD) and placed under the control of the human cytomegalovirus (CMV) immediate early promoter, using expression vector pFN26A (Promega) and standard recombinant DNA cloning methods. To serve as a control in the assay, a similar vector was generated in which the GAL4-DBD was fused to Herpes simplex virus protein 16 (VP16), a constitutive transcriptional activator.

To monitor the inhibitory effect of compounds on RORγ, a transcriptional reporter construct was used. The pGL4.35 vector (Promega) contains nine copies of the GAL4 Upstream Activator Sequence (UAS). This sequence drives the transcription of the luciferase reporter gene luc2P in response to binding of a fusion protein containing the GAL4 DNA binding domain, as for example expressed by the GAL4-RORγ-LBD and GAL4-VP16 expression vectors described above. To allow a GAL4 fusion protein to drive the expression of the luciferase reporter, the pGL4.35 expression vector and the appropriate GAL4 fusion protein expression vector were bulk transfected in the 293FT cells using standard transfection techniques.

The day after transfection, cells were plated into 96 well plates, test compound was added and the plates were incubated overnight. Subsequently, the firefly luciferase activity was quantified using luciferase detection reagent and luminescence readout.

Detailed Assay Description

293FT cells (Invitrogen) were transfected with a GAL4 fusion protein expression vector (as described above) and the transcriptional reporter construct (pGL4.35, Promega). 60 μL of TransIT-293 transfection reagent (Mirus Bio) was added drop wise to 1500 μl Opti-MEM I Reduced Serum Medium (Invitrogen) and incubated at RT (RT) for 5 to 20 minutes. 1500 μL of this reagent mixture was added to 5 μg of GAL4 fusion protein expression vector and 5 μg of the transcriptional reporter construct, and incubated at RT for 20 minutes.

To harvest 293FT cells from a T75 flask, first the culture medium was taken off the cells. Subsequently, the cells were washed with Phosphate Buffered Saline (PBS) (Lonza), after which the PBS was removed. To dissociate the cells, 1 ml of TrypLE Express (Invitrogen) was added to the flask, followed by incubation at RT until the cells visually started to detach. Cells were collected in 5 mL of assay medium (DMEM culture medium (Lonza), 10% dialyzed FBS (Invitrogen) and Pen/Strep (Lonza)) to achieve a single cell suspension. $10 \times 10^6$ cells were spun down and re-suspended in 10 mL of assay medium. Subsequently, the cell suspension was added to the transfection mix tube, and then transferred as a whole to a T75 flask (Greiner), followed by overnight (16-24 hours) incubation at 37° C. and 5% $CO_2$.

For compound screening, the cells were harvested (as described above) and counted. $13 \times 10^6$ cells were spun down, the supernatant was aspirated and the cells were re-suspended in 17.3 mL of assay medium obtaining a cell suspension of $0.75 \times 10^6$ cells/mL. 80 μL of cell suspension (60,000 cells) was plated per well into a white, flat bottom, tissue culture treated, 96 well screening plates (Greiner).

Test compounds were diluted, starting from a 10 mM dimethylsulfoxide (DMSO) stock solution, to serial dilutions in DMSO at 500× the final test concentration. Subsequently, these solutions were diluted to 5× the final test concentration in two 10-fold-dilution steps in assay medium. The final DMSO concentration of the 5× test compound solution was 1%. 20 μL of the 5× test compound solution was added to each test well of the 96 well plate previously plated with 80 μl cell suspension, resulting in the final test concentration with 0.2% DMSO.

The plates were incubated overnight (16-24 hours) at 37° C. and 5% $CO_2$.

For the luciferase readout, the luciferase reagent (Britelite Plus, Perkin Elmer) was brought to RT. To each test well of the screening plates, 100 μL of 2.5-fold diluted Britelite Plus reagent was added, followed by incubation at RT for 10 minutes. The luciferase luminescence signal was measured using a Wallac Victor Microplate Reader (Perkin Elmer).

The half maximum inhibitory concentration ($IC_{50}$) values for the test compounds were calculated from the luciferase signal using GraphPad Prism software (GraphPad Software).

Examples 1, (−)-1, (+)-1, 2, 4, 5, 6, 7, 8, 9, 10, 11, 12, 13, 14, 15, 17, 18, 19, 20, 21, 22, 23, 24, 25, 26, 27, 28, 29, 30, 31, 32, 33, 34, 35, 36, 37 and 38 were found to have mean $pIC_{50}$ values above 5.

Examples 1, (−)-1, (+)-1, 2, 4, 5, 6, 7, 8, 9, 10, 11, 12, 13, 14, 15, 18, 20, 21, 22, 23, 24, 25, 26, 27, 28, 29, 30, 31, 32, 33, 35, 36, 37 and 38 were found to have mean $pIC_{50}$ values above or equal to 6.

Examples 1, (+)-1, 4, 6, 7, 8, 9, 10, 11, 12, 14, 15, 22, 23, 24, 25, 26, 28, 29, 33, 36 and 38 were found to have mean $pIC_{50}$ values above or equal to 7.

Unexpectedly, example 3 as a pIC50 below 5.

Example 40

Peripheral Blood Mononuclear Cell (PBMC) IL-17 Assay

Example inhibitor 5 was tested for its ability to inhibit the IL-17A production in anti-CD3/anti-CD28 stimulated peripheral blood mononuclear cells (PBMCs) isolated from human blood. The assay procedure and results are described below.

PBMC IL-17 Assay Description

This assay is designed to measure the levels of IL-17A secreted from anti-CD3/anti-CD28 stimulated PBMCs with the aim of measuring RORγ mediated inhibition of IL-17A production.

The assay medium consists of 90% RPMI 1640 (Lonza), 10% heat inactivated fetal bovin serum (FBS, Lonza) and 100 U/mL penicillin/streptomycin solution.

Assay Description

Anti-CD3 antibody (BD Pharmingen) was diluted to 10 μg/ml in PBS (Lonza). 30 μL of 10 μg/ml anti-CD3 solution was added to the inner 60 wells, excluding any negative control wells, of a 96-well cell culture treated U-bottom plate (Greiner). Plates were incubated overnight (16-24 hours) at 37° C. and 5% $CO_2$.

Peripheral blood mononuclear cells were separated from buffy coats (Sanquin) using Ficoll-Paque PREMIUM separation medium (GE Healthcare Life Sciences) according to manufacturer's protocol and re-suspended in assay medium at 37° C.

Test compounds were diluted, starting from a 10 mM dimethylsulfoxide (DMSO) stock solution, to serial dilutions in DMSO at 200× the final test concentration. Subsequently, these solutions were diluted in two dilution steps in assay medium to 10× the final test concentration. The DMSO concentration of the 10× test compound solution was 5%.

Anti-CD28 antibody (BD Pharmingen) was diluted to 20 µg/mL in PBS. The PBMCs were diluted to a concentration of $2.5 \times 10^6$ cells/mL in assay medium at 37° C.

For compound screening, the anti-CD3 coated plates were washed three times with PBS, the wells were subsequently aspirated using vacuum. To each screening well 80 µL of the PBMC suspension, 10 µL of the anti-CD28 solution and 10 µL of the 10× test compound solution was added, resulting in the final test concentration with 0.5% DMSO. All outer wells were filled with assay medium to prevent evaporation. Plates were incubated for 5 days at 37° C. and 5% $CO_2$.

After incubation the plates were spun down at 1500 rpm for 4 minutes and the supernatant was collected. Subsequently, the IL-17A levels in the supernatants was determined using an IL-17 ELISA kit (human IL-17 DuoSet, R&D systems) according to manufacturer's protocol.

The half maximum inhibitory concentration ($IC_{50}$) values for the test compounds were calculated from the IL-17A signal using GraphPad Prism software (GraphPad Software).

The tested example 5 was found to have a mean $pIC_{50}$ value equal to 7.

The invention claimed is:

1. A compound of Formula (I)

or a pharmaceutically acceptable salt thereof, wherein:
$A_{11}$ is N or $CR_{11}$;
$A_{12}$ is N or $CR_{12}$;
$A_{13}$ is N or $CR_{13}$;
$A_{14}$ is N or $CR_{14}$;
with the proviso that no more than two of the four positions $A_{11}$, $A_{12}$, $A_{13}$, and $A_{14}$ are simultaneously N;

$R_1$ is C(2-6)alkyl, C(3-6)cycloalkyl, C(3-6)cycloalkylC(1-3)alkyl, (di)C(3-6)cycloalkylamino or (di)(C(3-6)cycloalkylC(1-3)alkyl)amino, wherein each carbon atom of said alkyl groups is optionally substituted with one or more F, and each carbon atom of said cycloalkyl groups is optionally substituted with one or more F or methyl;

$R_2$ and $R_3$ are independently H, F, methyl, ethyl, hydroxy, or methoxy, or $R_2$ and $R_3$ are taken together with the carbon atom to which they are attached to form a carbonyl, wherein each alkyl group, if present, is optionally substituted with one or more F;

$R_4$ is H or C(1-6)alkyl;

$R_5$ is H, hydroxyethyl, methoxyethyl, C(1-6)alkyl, C(6-10)aryl, C(6-10)arylC(1-3)alkyl, C(1-9)heteroaryl, C(1-9)heteroarylC(1-3)alkyl, C(3-6)cycloalkyl, C(3-6)cycloalkylC(1-3)alkyl, C(2-5)heterocycloalkyl or C(2-5)heterocycloalkyl-C(1-3)alkyl, each of which is optionally substituted with one or more F, Cl, C(1-2)alkyl, C(1-2)alkoxy or cyano;

the sulfonyl group containing $R_1$ is in the meta or para position and is represented by one of $R_7$, $R_8$ or $R_9$;

the remaining $R_6$-$R_{14}$ are independently H, halogen, amino, C(1-3)alkoxy, (di)C(1-3)alkylamino or C(1-6)alkyl, wherein each alkyl group is optionally substituted with one or more F;

$R_{15}$ is H, C(1-6)alkyl, C(3-6)cycloalkyl, C(3-6)cycloalkylC(1-3)alkyl, C(6-10)aryl, C(6-10)arylC(1-3)alkyl, C(1-9)heteroaryl, C(1-9)heteroarylC(1-3)alkyl, C(2-5)heterocycloalkyl or C(2-5)heterocycloalkylC(1-3)alkyl, each of which is optionally substituted with one or more F, Cl, C(1-2)alkyl, C(1-2)alkoxy or cyano; and $R_{16}$ is C(1-6)alkyl, C(3-6)cycloalkyl, C(3-6)cycloalkylC(1-3)alkyl, C(6-10)aryl, C(6-10)arylC(1-3)alkyl, C(1-9)heteroaryl, C(1-9)heteroarylC(1-3)alkyl, C(2-5)heterocycloalkyl or C(2-5)heterocycloalkylC(1-3)alkyl, each of which is optionally substituted with one or more F, Cl, C(1-2)alkyl, C(1-2)alkoxy or cyano, and wherein:
(i) "C(1-9)heteroaryl" is a mono- or bicyclic aromatic group having 1-9 carbon atoms and 1-4 heteroatoms selected from the group consisting of nitrogen, sulfur and oxygen, and which can be attached via a nitrogen atom if feasible, or a carbon atom, and wherein each carbon atom is optionally substituted with one or more halogen or methyl; and (ii) "C(2-5)heterocycloalkyl" is a saturated cyclic hydrocarbon group having 2-5 carbon atoms and 1-3 heteroatoms selected from the group consisting of nitrogen, sulfur and oxygen, and which can be attached via a nitrogen atom if feasible, or a carbon atom, and wherein each carbon atom is optionally substituted with one or more halogen or methyl.

2. The compound according to claim 1, or a pharmaceutically acceptable salt thereof wherein:
$A_{11}$ is N or $CR_{11}$;
$A_{12}$ is N or $CR_{12}$;
$A_{13}$ is N or $CR_{13}$;
$A_{14}$ is N or $CR_{14}$;
with the proviso that no more than two of the four positions $A_{11}$, $A_{12}$, $A_{13}$, and $A_{14}$ are simultaneously N;
$R_1$ is C(2-6)alkyl, C(3-6)cycloalkylC(1-3)alkyl or (di)C(3-6)cycloalkylamino, wherein each carbon atom of said alkyl groups is optionally substituted with one or more F, and each carbon atom of said cycloalkyl groups is optionally substituted with one or more F or methyl;

$R_2$ and $R_3$ are independently H or methyl, or $R_2$ and $R_3$ are taken together with the carbon atom to which they are attached to form a carbonyl, wherein the methyl group, if present, is optionally substituted with one or more F;

$R_4$ is H;

$R_5$ is H, hydroxyethyl, methoxyethyl, C(1-6)alkyl, C(6-10)arylC(1-3)alkyl, C(2-5)heterocycloalkyl or C(2-5)heterocycloalkyl-C(1-3)alkyl, each of which is optionally substituted with one or more F, C(1-2)alkyl, C(1-2)alkoxy or cyano;

the sulfonyl group containing $R_1$ is represented by $R_8$;

the remaining $R_6$-$R_{14}$ are independently H, halogen, C(1-3)alkoxy or C(1-6)alkyl, wherein each alkyl group is optionally being substituted with one or more F;

$R_{15}$ is C(1-6)alkyl optionally substituted with one or more F, or C(1-9)heteroaryl substituted with one C(1-2)alkyl; and $R_{16}$ is C(1-6)alkyl, C(3-6)cycloalkyl, C(3-6)cycloalkylC(1-3)alkyl, C(6-10)aryl, C(6-10)arylC(1-3)alkyl, C(2-5)heterocycloalkyl or C(2-5)heterocycloalkyl-C(1-3)alkyl, each of which is optionally substituted with one or more F.

3. The compound according to claim 1, or a pharmaceutically acceptable salt thereof, wherein:

$A_{11}$-$A_{14}$ are $CR_{11}$, $CR_{12}$, $CR_{13}$, and $CR_{14}$, respectively;

$R_1$ is C(2-6)alkyl, C(3-6)cycloalkylC(1-3)alkyl, or (di)C(3-6)cycloalkylamino;

$R_2$ and $R_3$ are independently H or methyl;

$R_4$ is H;

$R_5$ is H, C(1-6)alkyl or C(6-10)arylC(1-3)alkyl;

the sulfonyl group containing $R_1$ is represented by $R_8$;

the remaining $R_6$-$R_{14}$ are independently H or C(1-6)alkyl;

$R_{15}$ is C(1)alkyl optionally substituted with one or more F, or C(3)heteroaryl substituted with one methyl; and $R_{16}$ is C(1-6)alkyl, C(3-6)cycloalkyl, C(6-10)aryl or C(6-10)arylC(1-3)alkyl, each of which is optionally substituted with one or more F, and wherein "C(3)heteroaryl" is a monocyclic aromatic group having 3 carbon atoms and 2 heteroatoms selected from the group consisting of nitrogen, sulfur, and oxygen, and which can be attached via a nitrogen atom if feasible, or a carbon atom.

4. The compound according to claim 1, or a pharmaceutically acceptable salt thereof wherein:

one of $A_{11}$ and $A_{14}$ is N, and the other of $A_{11}$ and $A_{14}$ is $CR_{11}$ or $CR_{14}$;

$A_{12}$ and $A_{13}$ are $CR_{12}$ and $CR_{13}$, respectively;

$R_1$ is C(3-6)cycloalkylC(1-3)alkyl;

$R_2$ and $R_3$ are independently H;

$R_4$ is H;

$R_5$ is H;

the sulfonyl group containing $R_1$ is represented by $R_8$;

the remaining $R_6$-$R_{14}$ are independently H or methyl; and $R_{15}$ and $R_{16}$ are independently C(1)alkyl, the carbon atom of which is optionally substituted with one or more F.

5. The compound according to claim 1, or a pharmaceutically acceptable salt thereof, which is selected from the group consisting of:

N-[[4-(cyclopropylmethylsulfonyl)phenyl]methyl]-4-[1-hydroxy-1-(trifluoromethyl)propyl]benzamide;

(−)-N-[[4-(cyclopropylmethylsulfonyl)phenyl]methyl]-4-[1-hydroxy-1-(trifluoromethyl)propyl]benzamide;

(+)-N-[[4-(cyclopropylmethylsulfonyl)phenyl]methyl]-4-[1-hydroxy-1-(trifluoromethyl)propyl]benzamide;

N-[[4-(cyclopropylmethylsulfonyl)phenyl]methyl]-4-(2,2,2-trifluoro-1-hydroxy-1-methyl-ethyl)benzamide;

N-[[4-(cyclopropylmethylsulfonyl)phenyl]methyl]-4-(1-hydroxy-1-methyl-ethyl)benzamide;

N-[[4-(cyclopropylmethylsulfonyl)phenyl]methyl]-4-[2,2,2-trifluoro-1-hydroxy-1-(trifluoromethyl)ethyl]benzamide;

N-[[4-(cyclopropylmethylsulfonyl)phenyl]methyl]-4-[1-(difluoromethyl)-2,2,2-trifluoro-1-hydroxy-ethyl]benzamide;

N-[[4-(cyclopropylmethylsulfonyl)phenyl]methyl]-4-[1-hydroxy-1-(trifluoromethyl)butyl]benzamide;

N-[[4-(cyclopropylmethylsulfonyl)phenyl]methyl]-4-[1-hydroxy-1-(trifluoromethyl)pentyl]benzamide;

N-[[4-(cyclopropylmethylsulfonyl)phenyl]methyl]-4-[1-hydroxy-3-methyl-1-(trifluoromethyl)butyl]benzamide;

N-[[4-(cyclopropylmethylsulfonyl)phenyl]methyl]-4-[1-hydroxy-3,3-dimethyl-1-(trifluoromethyl)butyl]benzamide;

N-[[4-(cyclopropylmethylsulfonyl)phenyl]methyl]-4-[1-hydroxy-2-methyl-1-(trifluoromethyl)propyl]benzamide;

N-[[4-(cyclopropylmethylsulfonyl)phenyl]methyl]-4-(1-cyclopropyl-2,2,2-trifluoro-1-hydroxy-ethyl)benzamide;

4-(1-cyclopentyl-2,2,2-trifluoro-1-hydroxy-ethyl)-N-[[4-(cyclopropylmethylsulfonyl)phenyl]methyl]benzamide;

N-[[4-(cyclopropylmethylsulfonyl)phenyl]methyl]-4-(2,2,2-trifluoro-1-hydroxy-1-phenyl-ethyl)benzamide;

4-(1-benzyl-2,2,2-trifluoro-1-hydroxy-ethyl)-N-[[4-(cyclopropylmethylsulfonyl)phenyl]methyl]benzamide;

N-[[4-(cyclopropylmethylsulfonyl)phenyl]methyl]-3-methyl-4-[2,2,2-trifluoro-1-hydroxy-1-(trifluoromethyl)ethyl]benzamide;

N-[[4-(cyclopropylmethylsulfonyl)phenyl]methyl]-5-[2,2,2-trifluoro-1-hydroxy-1-(trifluoromethyl)ethyl]pyridine-2-carboxamide;

N-[(4-ethyl sulfonylphenyl)methyl]-4-[1-hydroxy-1-(trifluoromethyl)propyl]benzamide;

N-[(4-ethylsulfonylphenyl)methyl]-4-[1-hydroxy-3,3-dimethyl-1-(trifluoromethyl)butyl]benzamide;

N-[(4-ethylsulfonylphenyl)methyl]-4-[2,2,2-trifluoro-1-hydroxy-1-(trifluoromethyl)ethyl]benzamide;

N-[[4-(cyclopropylsulfamoyl)phenyl]methyl]-4-[1-hydroxy-1-(trifluoromethyl)pentyl]benzamide;

N-[[4-(cyclopropylsulfamoyl)phenyl]methyl]-4-[2,2,2-trifluoro-1-hydroxy-1-(trifluoromethyl)ethyl]benzamide;

N-[[4-(cyclopropylmethylsulfonyl)phenyl]methyl]-4-[2,2,2-trifluoro-1-methoxy-1-(trifluoromethyl)ethyl]benzamide;

N-[[4-(cyclopropylmethyl sulfonyl)phenyl]methyl]-4-[1-ethoxy-2,2,2-trifluoro-1-(trifluoromethyl)ethyl]benzamide;

N-[[4-(cyclopropylmethyl sulfonyl)phenyl]methyl]-4-[2,2,2-trifluoro-1-propoxy-1-(trifluoromethyl)ethyl]benzamide;

4-[1-butoxy-2,2,2-trifluoro-1-(trifluoromethyl)ethyl]-N-[[4-(cyclopropylmethyl sulfonyl)phenyl]methyl]benzamide;

N-[[4-(cyclopropylmethyl sulfonyl)phenyl]methyl]-4-[2,2,2-trifluoro-1-isopropoxy-1-(trifluoromethyl)ethyl]benzamide;

4-[1-benzyloxy-2,2,2-trifluoro-1-(trifluoromethyl)ethyl]-N-[[4-(cyclopropylmethyl sulfonyl)phenyl]methyl]benzamide;

N-[[4-(cyclopropylmethyl sulfonyl)-2-methyl-phenyl]methyl]-4-[2,2,2-trifluoro-1-methoxy-1-(trifluoromethyl)ethyl]benzamide;

N-[[4-(cyclopropylmethyl sulfonyl)-2-methyl-phenyl]methyl]-4-[1-ethoxy-2,2,2-trifluoro-1-(trifluoromethyl)ethyl]benzamide;

N-[[4-(cyclopropyl sulfamoyl)phenyl]methyl]-4-[2,2,2-trifluoro-1-methoxy-1-(trifluoromethyl)ethyl]benzamide;

N-[[4-(cyclopropyl sulfamoyl)phenyl]methyl]-4-[1-ethoxy-2,2,2-trifluoro-1-(trifluoromethyl)ethyl]benzamide;

N-[[4-(cyclopropyl sulfamoyl)phenyl]methyl]-4-[2,2,2-trifluoro-1-propoxy-1-(trifluoromethyl)ethyl]benzamide;

N-[[4-(cyclopropylmethyl sulfonyl)phenyl]methyl]-4-[1-methoxy-3,3-dimethyl-1-(trifluoromethyl)butyl]benzamide;

N-[(1R)-1-[4-(cyclopropylmethyl sulfonyl)phenyl]ethyl]-4-[2,2,2-trifluoro-1-hydroxy-1-(trifluoromethyl)ethyl]benzamide;

N-[(1S)-1-[4-(cyclopropylmethylsulfonyl)phenyl]ethyl]-4-[2,2,2-trifluoro-1-hydroxy-1-(trifluoromethyl)ethyl]benzamide;

N-[[4-(cyclopropylmethyl sulfonyl)phenyl]methyl]-4-[1-hydroxy-2-methyl-1-(5-methylisoxazol-3-yl) propyl]benzamide;

4-[cyclopropyl-hydroxy-(5-methylisoxazol-3-yl)methyl]-N-[[4-(cyclopropylmethylsulfonyl)phenyl]methyl]benzamide; and N-[(4-(cyclopropylmethyl sulfonyl)phenyl)methyl]-4-[1-hydroxy-2,2-dimethyl-1-(5-methylisoxazol-3-yl)propyl]benzamide.

6. A pharmaceutical composition comprising the compound of Formula (I) according to claim 1, or a pharmaceutically acceptable salt thereof, and one or more pharmaceutically acceptable excipients.

\* \* \* \* \*